United States Patent

Ditrich et al.

Patent Number: 5,256,633
Date of Patent: * Oct. 26, 1993

[54] OXAZOLE- AND THIAZOLECARBOXAMIDES AS HERBICIDES

[75] Inventors: Klaus Ditrich, Bad Duerkheim; Volker Maywald, Ludwigshafen; Gerhard Hamprecht, Weinheim; Albrecht Harreus, Ludwigshafen; Bruno Wuerzer, Otterstadt; Karl-Otto Westphalen, Speyer, all of Fed. Rep. of Germany

[73] Assignee: BASF Aktiengesellschaft, Ludwigshafen, Fed. Rep. of Germany

[*] Notice: The portion of the term of this patent subsequent to Sep. 14, 2010 has been disclaimed.

[21] Appl. No.: 870,386

[22] Filed: Apr. 17, 1992

Related U.S. Application Data

[60] Division of Ser. No. 830,326, Dec. 26, 1991, which is a continuation of Ser. No. 587,853, Sep. 25, 1990, abandoned.

[51] Int. Cl.$^5$ .............................. A01N 43/78
[52] U.S. Cl. ...................... 504/266; 504/233; 504/235; 504/244; 504/261
[58] Field of Search ............ 71/88, 90; 504/266, 504/233, 235, 244, 261

Primary Examiner—Richard L. Raymond
Assistant Examiner—B. Bembenick
Attorney, Agent, or Firm—Keil & Weinkauf

[57] ABSTRACT

Oxazole- and thiazolecarboxamides of the formulae Ia and Ib

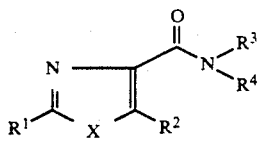

Ia

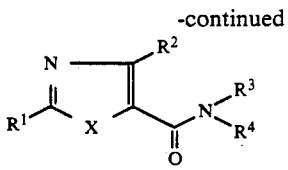

Ib where the substituents have the following meanings:
oxygen or sulfur;
hydrogen; halogen; substituted or unsubstituted $C_1$-$C_6$-alkyl, benzyl, cycloalkyl, alkenyl, alkynyl, phenyl, phenoxy or phenylthio; alkoxy; alkylthio; haloalkoxy; haloalkylthio; or a substituted or unsubstituted 5- or 6-membered heterocyclic radical;
formyl, 4,5-dihydrooxazol-2-yl or —COYR$^5$;
oxygen or sulfur;
hydrogen; cycloalkyl; substituted or unsubstituted alkyl, phenyl, benzyl, alkenyl, cycloalkenyl or alkynyl; a substituted or unsubstituted 5- or 6-membered heterocyclic radical; phthalimido; tetrahydrophthalimido; succinimido; maleiimido; one equivalent of a cation; or

—N=CR$^6$R$^7$;

R$^6$, R$^7$ hydrogen; alkyl; cycloalkyl; phenyl; furyl or together a methylene chain or 4 to 7 members;
hydrogen or substituted or unsubstituted alkyl or cycloalkyl;
R$^4$ hydroxy; alkoxy; substituted or unsubstituted alkyl, cycloalkyl, alkenyl, alkynyl, phenyl or naphthyl; a substituted or unsubstituted 5- or 6-membered heterocyclic radical; or R$^3$ and R$^4$ together are —(CH$_2$)$_n$—Y$_p$—(CH$_2$)$_q$—, where n and q are 1, 2 or 3, p is 0 or 1 and Y is oxygen, sulfur or N-methyl, or form a radical of the formula —(CH$_2$)$_3$—CO—, and their environmentally tolerated salts, X is formula Ib not being sulfur when R$^1$ is 3-pyridyl, R$^2$ is CO$_2$CH$_2$CH$_3$ or R$^3$ is hydrogen, and X in formula Ia X not being sulfur and R$^1$ not being thien-2-yl when YR$^5$ is OH, R$^3$ is hydrogen and R$^4$ is methyl, processes for manufacturing such compounds and herbicidal agents containing compounds of the formula Ia or Ib as active ingredients.

3 Claims, No Drawings

OXAZOLE-AND THIAZOLECARBOXAMIDES AS HERBICIDES

This is a divisional of application Ser. No. 07/830,326, filed Dec. 26, 1991, which is a continuation of Ser. No. 07/587,853, filed Sep. 25, 1990 (abandoned).

The present invention relates to oxazole- and thiazolecarboxamides of the formulae Ia and Ib

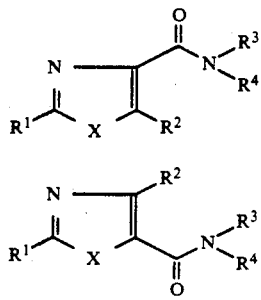

where

X is oxygen or sulfur;

$R^1$ is hydrogen; halogen; $C_1$–$C_6$-alkyl which can carry from one to five halogen atoms and/or one or two of the following: $C_3$–$C_6$-cycloalkyl, $C_1$–$C_4$-alkoxy, $C_1$–$C_4$-haloalkoxy, $C_1$–$C_4$-alkylthio, $C_1$–$C_4$-haloalkylthio or cyano; benzyl which can carry from one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro; $C_3$–$C_8$ cycloalkyl which can carry from one to three of the following: $C_1$–$C_4$-alkyl or halogen; $C_2$–$C_6$-alkenyl which can carry from one to three of the following: halogen, $C_1$–$C_3$-alkoxy and/or one phenyl which in turn can carry from one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro; $C_2$–$C_6$-alkynyl which can carry from one to three of the following: halogen, $C_1$–$C_3$-alkoxy and/or one phenyl which in turn can carry from one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro; $C_1$–$C_4$-alkoxy; $C_1$–$C_4$-alkylthio; $C_1$–$C_4$-haloalkoxy; $C_1$–$C_4$-haloalkylthio; phenoxy or phenylthio, which can carry from one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro; a 5- to 6-membered heterocyclic radical containing one or two hetero atoms selected from the group comprising oxygen, sulfur and nitrogen, it being possible for the ring to carry one or two of the following: $C_1$–$C_3$-alkyl, halogen, $C_1$–$C_3$-alkoxy or $C_1$–$C_3$-alkoxycarbonyl; phenyl which can carry from one to three of the following: $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, halogen, nitro and cyano;

$R^2$ is formyl, 4,5-dihydro-2-oxazolyl or —$COYR^5$;

Y is oxygen or sulfur;

$R^5$ is hydrogen; $C_1$–$C_6$-alkyl which can carry from one to five halogen atoms or hydroxyl groups and/or one of the following: $C_1$–$C_4$-alkoxy, $C_2$–$C_4$-alkoxy-$C_1$–$C_4$-alkoxy, cyano, trimethylsilyl, $C_1$–$C_3$-alkylthio, $C_1$–$C_3$-alkylamino, di-$C_1$–$C_3$-alkylamino, $C_3$–$C_7$-cycloalkylamino, $C_1$–$C_3$-alkylsulfinyl, $C_1$–$C_3$-alkylsulfonyl, carboxyl, $C_1$–$C_3$-alkoxycarbonyl, di-$C_1$–$C_3$-alkylaminocarbonyl, di-$C_1$–$C_3$-alkoxyphosphoryl, alkaneiminoxy, thienyl, furyl, tetrahydrofuryl, phthalimido, pyridyl, benzyloxy or benzoyl, it being possible for the cyclic radicals in turn to carry from one to three of the following: $C_1$–$C_3$-alkyl, $C_1$–$C_3$-alkoxy or halogen; benzyl which can carry from one to three of the following: $C_1$–$C_3$-alkyl, $C_1$–$C_3$-alkoxy, $C_1$–$C_3$-haloalkyl, halogen, nitro and cyano; $C_3$–$C_8$-cycloalkyl; phenyl, which can carry from one to three of the following: $C_1$–$C_4$-alkyl, $C_1$–$C_4$-alkoxy, $C_1$–$C_4$-haloalkyl, $C_1$–$C_4$-haloalkoxy, $C_1$–$C_4$-alkoxycarbonyl, halogen, nitro and cyano; $C_3$–$C_8$-alkenyl, $C_5$–$C_6$-cycloalkenyl or $C_3$–$C_8$-alkynyl, it being possible for these radicals to carry one of the following: hydroxyl, $C_1$–$C_4$-alkoxy, halogen or a phenyl ring which in turn can carry from one to three of the following: $C_1$–$C_4$-alkyl, $C_1$–$C_4$-alkoxy, $C_1$–$C_4$-haloalkyl, halogen, nitro and cyano; a 5- to 6-membered heterocyclic radical containing one or two hetero atoms selected from the group comprising oxygen, sulfur and nitrogen or a benzotriazolyl radical; phthalimido; tetrahydrophthalimido; succinimido; maleimido; one equivalent of a cation from the group comprising the alkali metals or alkaline earth metals, manganese, copper, iron, ammonium and substituted ammonium;

$R^6$ and $R^7$ are hydrogen; $C_1$–$C_4$-alkyl; $C_3$–$C_6$-cycloalkyl; phenyl or furyl, or together form a methylene chain —$(CH_2)_m$— with m=4 to 7;

$R^3$ is hydrogen; $C_1$–$C_6$-alkyl which can carry from one to three of the following: hyroxyl; halogen, $C_1$–$C_4$-alkoxy, $C_1$–$C_4$-alkylthio or di-$C_1$–$C_3$-alkylamino; $C_3$–$C_8$-cycloalkyl which can carry from one to three of the following: $C_1$–$C_4$-alkyl, halogen and $C_1$–$C_4$-haloalkyl;

$R^4$ is hydroxyl; $C_1$–$C_4$-alkoxy; $C_1$–$C_6$-alkyl which can carry from one to three of the following: $C_1$–$C_4$-alkoxy, $C_1$–$C_4$-haloalkoxy, $C_1$–$C_4$-alkylthio, $C_1$–$C_4$-haloalkylthio, di-$C_1$–$C_4$-alkylamino, halogen, $C_3$–$C_8$-cycloalkyl or phenyl which in turn can carry from one to three of the following: halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio; $C_3$–$C_8$-cycloalkyl which can carry from one to three of the following: $C_1$–$C_6$-alkyl, $C_1$–$C_6$-haloalkyl, $C_1$–$C_4$-alkoxy, $C_1$–$C_4$-haloalkoxy, halogen, nitro or cyano; $C_3$–$C_6$-alkenyl or $C_3$–$C_6$-alkynyl, which can be substituted from once to three times by halogen and/or once by phenyl which in turn can carry from one to three of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro; a 5- to 6-membered heterocyclic radical which contains one or two hetero atoms selected from the group comprising oxygen, sulfur or nitrogen, and which can carry from one to three of the following: $C_1$–$C_4$-alkyl or halogen; phenyl which can carry from one to four of the following: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, $C_1$–$C_4$-alkanoyl, $C_1$–$C_4$-haloalkanoyl or $C_1$–$C_4$-alkoxycarbonyl; naphthyl which can be substituted from once to three times by $C_1$–$C_4$-alkyl or halogen, or $R^3$ and $R^4$ together form —$(CH_2)_n$—$Y_p$—$(CH_2)_q$— where n and q are each 1, 2 or 3, p is 0 or 1 and Y is oxygen sulfur or N-methyl, or —$(CH_2)_3$—CO—, and the environmentally compatible salts thereof, where X in the formula Ib is not sulfur when $R^1$ is 3-pyridyl, $R^2$ is $CO_2CH_2CH_3$ or $R^3$ is hydrogen, and where X in the formula Ia is not sulfur and $R^1$ is not 2-thienyl when $YR^5$ is OH and $R^3$ is hydrogen and $R^4$ is methyl.

The invention also relates to processes for preparing these compounds, and to herbicides which contain at least one compound Ia' or Ib' in which the substituents have the abovementioned meanings and X can be sulfur when $R^1$ is 3-pyridyl, $R^2$ is $CO_2CH_2CH_3$ and $R^2$ is hydrogen, or when $R^1$ is 2-thienyl, $YR^5$ is hydroxyl, $R^3$ is hydrogen and $R^4$ is methyl.

Oxazole- and thiazolecarboxylic acids and derivatives thereof are known (DE-A 2,254,944, Bull. Soc. Chim. Fr., 1969, 2152 and DE-A 2,221,647). Possible uses of these substances as herbicides have not been described.

It is an object of the present invention to find and synthesize novel herbicidal compounds.

We have found that this object is achieved by the oxazole- and thiazolecarboxamides Ia and Ib defined in the first paragraph.

We have also found processes for preparing them and herbicides which contain oxazole- and thiazolecarboxamides Ia' and Ib' in which the substituents have the abovementioned meanings.

The oxazole- and thiazolecarboxamides Ia and Ib according to the invention can be prepared in a variety of ways. They are obtained, for example, by the following processes:

1. Process for preparing compounds Ia and Ib where $R^2$ is $CO_2R^5$ and $R^5$ is $C_1$-$C_6$-alkyl

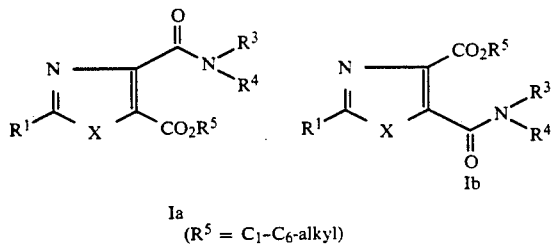

Ia
Ib
($R^5 = C_1$-$C_6$-alkyl)

These oxazole- and thiazolecarboxamides Ia and Ib are obtained by hydrolyzing a diester of the formula II in a conventional manner with one equivalent of an aqueous base to give the monoesters IIIa and IIIb and then separating IIIa and IIIb or initially converting the mixture to the halide or another active form to the carboxylic acid and subsequently amidating these derivatives with an amine IV.

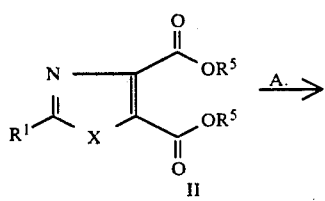

II

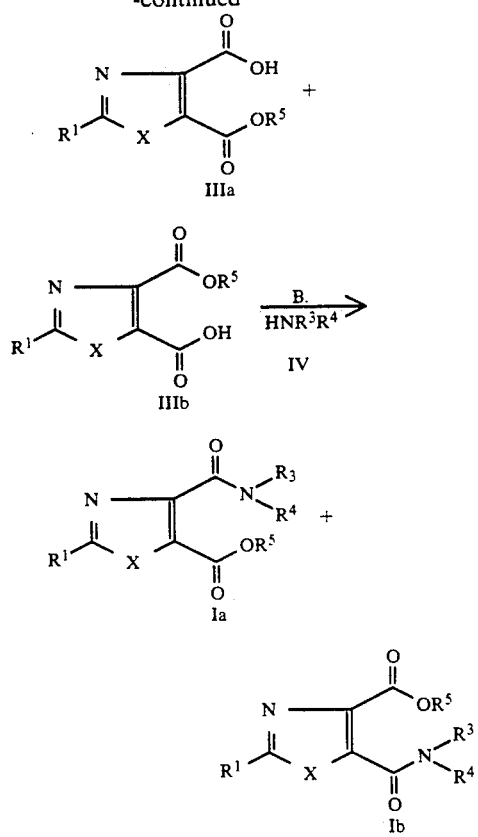

The individual steps A and B in this reaction sequence can be carried out as follows:

Step A:

The partial hydrolysis of the diester II to the monoesters IIIa and IIb is normally carried out at from $-20°$ to $60°$ C., preferably $-10°$ to $30°$ C., in an inert organic solvent which is miscible with water, in the presence of from 1.0 to 1.2 mole equivalents of a base.

Particularly suitable bases are alkali metal hydroxides. The base is generally added as an aqueous solution which is from 5 to 20% strength.

Examples of preferred solvents for this reaction are dioxane or the alcohol corresponding to the ester component in the formula II.

The reaction mixture is normally worked up by acidification, when the desired product separates out as a solid or oil. Isolation is carried out in a conventional manner by filtration or extraction.

The mixture of the two isomeric monoesters IIIa and IIIb can be separated by fractional crystallization or chromatography, or it can be reacted further without separation.

Step B:

The compounds Ia and Ib are obtained from the monoesters IIIa and IIIb by initially converting the latter in a conventional manner into the halide or another active form of the carboxyl group and subsequently amidating these derivatives with an amine IV.

Examples of active forms of carboxylic acids are, besides the halides such as, in particular, the chlorides and bromides, also the imidazolides. The halides are generally preferred.

They are obtained by reacting the carboxylic acids IIIa and IIIb with a halogenating agent such as thionyl chloride or bromide, phosphorus oxychloride or oxybromide, trichloride or tribromide or pentachloride or pentabromide, phosgene and elemental chlorine and bromine.

From 1 to 5 mole equivalents, preferably from 1 to 2 mole equivalents, of halogenating agent are used.

The reaction is carried out at from 0° C. to the boiling point of the halogenating agent or, if an inert organic solvent is used, the boiling point thereof, preferably at from 20° to 120° C.

Examples of suitable solvents are hydrocarbons and halohydrocarbons such as tetrachloroethane, methylene chloride, chloroform, dichloroethane, chlorobenzene, 1,2-dichlorobenzene, benzene, toluene and xylene.

The active carboxylic acid derivatives are normally isolated, for example by removing the halogenating agent and, where present, the solvent by distillation and only then reacting them with the amines IV.

In this case, the amidation is carried out from −20° to 100° C., preferably at −10° to 20° C., in an inert aprotic polar organic solvent.

Particularly suitable solvents for this reaction are halohydrocarbons such as dichloromethane, and ethers such as diethyl ether and tert-butyl methyl ether.

Since hydrogen halide is formed in the amidation of acid halides, it is advisable to add the amine IV in an excess of from 2 to 5 mole equivalents, preferably 2 to 3 mole equivalents. If the amine is used in equimolar amount (from 1 to 1.2 mole equivalents), a base should be added, especially a tertiary amine such as triethylamine or pyridine, to bind the hydrogen halide.

When a mixture of the monoesters IIIa and IIIb is used as starting material, the reaction results in a mixture of the isomeric carboxamides Ia and Ib. This mixture can be fractionated into the individual components in a conventional manner, for example by fractional crystallization or chromatography.

The precursors II required for this synthesis are known (Bull. Soc. Chim. Fr. 1974, 2079) or can be obtained by known methods (Bull. Soc. Chim. Fr. 1969, 1762; J. Chem. Soc., 1953, 93).

2. Process for preparing compounds Ia and Ib where X is sulfur and $R^2$ is $CO_2H$

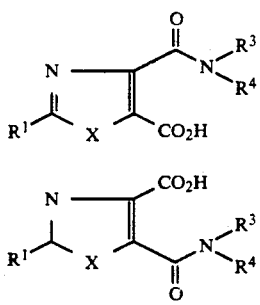

These thiazolecarboxamides Ia and Ib are obtained particularly advantageously by reacting a dicarboxylic anhydride of the formula V in a conventional manner with an amine of the formula IV to give the isomers Ia and Ib and subsequently fractionating the mixture to give the isomers

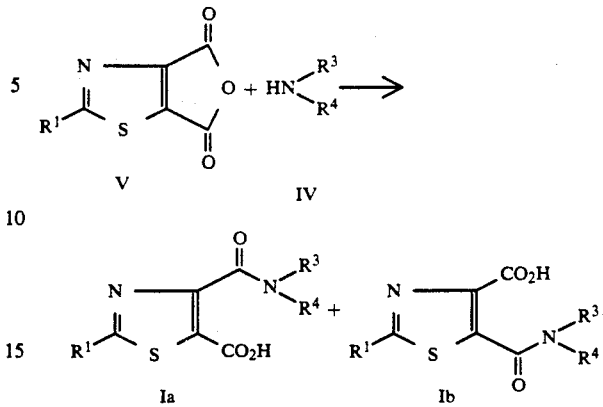

The reaction is normally carried out at from −10° to 150° C., preferably 20° to 120° C., in an inert aprotic polar organic solvent.

Particularly suitable solvents are halohydrocarbons, e.g. tetrachloroethane, methylene chloride, chloroform, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxan; dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one; aromatic compounds, e.g. benzene, toluene, xylene, pyridine and quinoline; ketones, e.g. acetone, methyl ethyl ketone or mixtures thereof.

The amine IV is generally used in equimolar amounts or in an excess, preferably in amounts of from 1.0 to 5.0 mole equivalents based on V.

The dicarboxylic anhydrides rqeuired for this process as known or can be prepared by known methods (Bull. Soc. Chim. Fr. 1969, 1762; CS-A-195,369; CS-A-195,370).

3. Process for preparing compounds Ia and Ib where $R^1$ is not halogen and $R^2$ is carboxyl or formyl

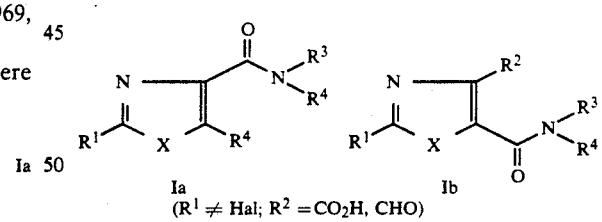

($R^1 \neq$ Hal; $R^2 = CO_2H$, CHO)

These isomeric oxazole- and thiazolecarboxamides are obtained by activating and amidating a carboxylic acid IIIc or IIId under the conditions described in 1B, and then reacting the resulting amides VIa and VIb in a conventional manner in the presence of a carboxylating or formylating reagent.

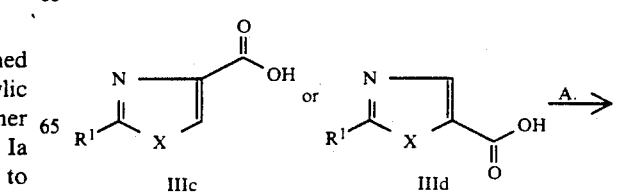

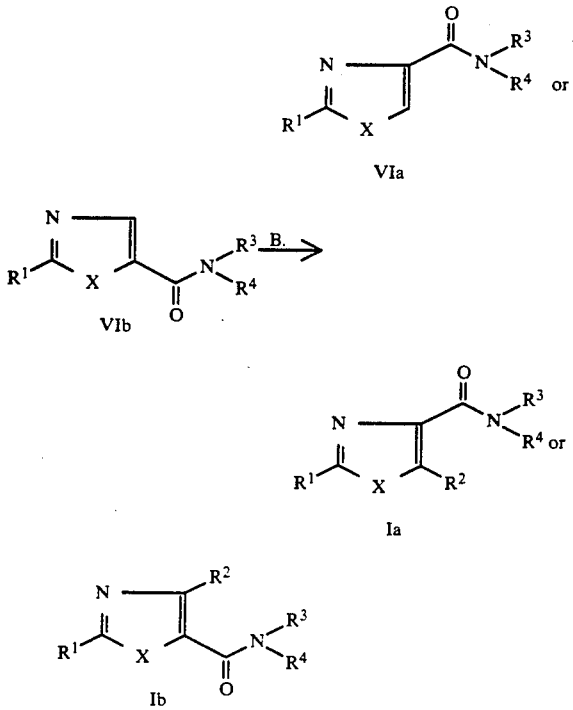

Step A in this reaction sequence is generally carried out under the conditions described in Section B in Process 1.

Step B.

The carboxylation or formylation of the oxazole- and thiazolecarboxamides VIa and VIb is usually carried out at from 0 to $-100°$ C., preferably $-50°$ to $-80°$ C., in an inert aprotic polar organic solvent in the presence of a base with exclusion of moisture.

The preferred carboxylating agent is gaseous or solid carbon dioxide, and dimethylformamide or N-formyl-morpholine is used, in particular, as formylating reagent.

Suitable solvents are, in particular, ethers, e.g. diethyl ether, methyl tert-butyl ether, dimethoxyethane, diethylene glycol dimethyl ether, tetrahydrofuran and dioxan.

The bases which are preferably used are organometallic compounds, e.g. methyllithium, n-butyllithium, s-butyllithium, t-butyllithium or phenyllithium.

The reaction is normally carried out by first adding up to 3 mole equivalents of the dissolved base to a solution of the oxazole- or thiazolecarboxamide VIa or VIb, resulting in a derivative which is metalated on the heterocycle and is then converted into the desired product Ia or Ib by addition of the electrophilic carboxylating or formylating reagent.

Where $R^3$ is hydrogen, correspondingly more mole equivalents of the base are rqeuired because, in this case, the amide nitrogen is initially deprotonated. Hence, from 2 to 2.5 mole equivalents of the base are preferably used for the reaction of carboxamides VIa or VIb where $R^3$ is hydrogen.

Compounds VIa and VIb where $R^1$ is hydrogen react with the base initially to metalate the 2-position of the heterocycle ring.

In order to introduce the carboxyl or formyl radical adjacent to the carbamoyl group in this case, it is necessary to start from oxazole- or thiazolecarboxamides VIa or VIb where $R^3$ is hydrogen.

Oxazole- and thiazolecarboxamides Ia and Ib where $R^1$ is hydrogen and $R^3$ is not hydrogen are obtained from the compounds which can be obtained by the abovementioned process and in which $R^1$ and $R^3$ are hydrogen in a conventional manner by subsequent alkylation or cycloalkylation.

The carboxylic acids IIIc and IIId required for the abovementioned process are known form the literature (Beilstein, Volume 27, Supplements 1–5) or can be prepared by conventional methods, for example by oxidation of the corresponding alcohols or aldehydes or by hydrolysis of the corresponding nitriles (J. V. Metzger in "The Chemistry of Heterocyclic Compounds, Vol. 34, Part 1, Thiazole and its Derivatives", Arnold Weissberger and Edward C. Taylor (Editors), John Wiley and Sons, pages 519 et sec., I. J. Turchi in "The Chemistry of Heterocyclic Compounds, Vol. 45, Oxazoles", Arnold Weissberger and Edward C. Taylor (Editors), John Wiley and Sons).

4. Process for preparing compounds Ia and Ib where $R^2$ is carboxyl

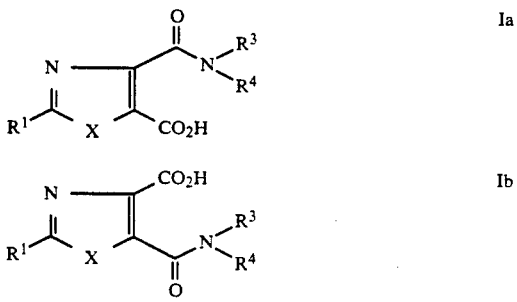

These oxazole- and thiazolecarboxamides Ia and Ib are obtained, for example, by hydrolyzing an appropriate carboxamide Ia or Ib where $R^2$ is $CO_2R^5$ and $R^5$ is $C_1$–$C_6$-alkyl in a conventional manner with one equivalent of an aqueous base. The reaction is shown in the following diagram only for the carboxamides Ia. It takes place similarly with the corresponding carboxamides Ib.

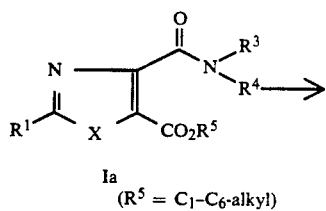

Ia
($R^5 = C_1$–$C_6$-alkyl)

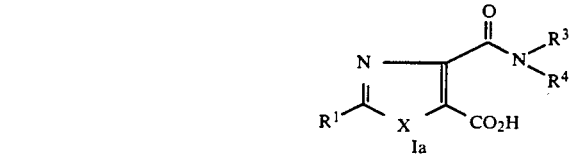

Ia

This synthesis is generally carried out under the conditions described in Section A in Process 1.

5. Process for preparing compounds Ia and Ib where $R^2$ is $COYR^5$

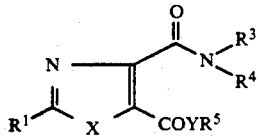

Ia

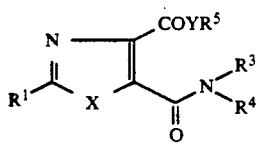

Ib

These carboxamides Ia and Ib are obtained by activating a corresponding carboxylic acid Ia or Ib ($R^2$=$CO_2H$) and subsequent reaction in a conventional manner with a compound VII.

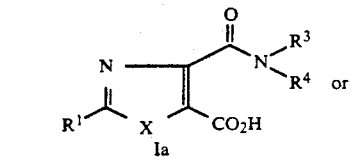

Ia

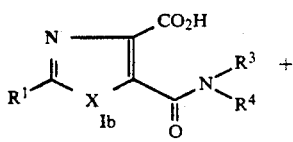

Ib

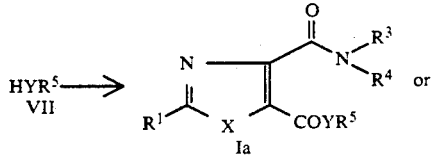

The reaction can be carried out at from $-20°$ C. to the reflux temperature of the solvent or mixture thereof, preferably at from $0°$ to $60°$ C.

Solvents expediently used for these reactions are halohydrocarbons, e.g. tetrachloroethane, methylene chloride, chloroform, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxan; aromatic compounds, e.g. benzene, toluene or xylene; or mixtures thereof.

Suitable condensing agents are dicyclohexylcarbodiimide or propanephosphonic anhydride.

The molar ratios of the starting compounds in the reaction are generally from 0.5:1 to 2:1 for the ratio of carboxylic acid VIa to alcohol or thiol and from 1:1 to 1:3 for the ratio of carboxylic acid IVa to condensing agent.

The concentration of the precursors in the solvent is generally from 0.1 to 5 mol/l, preferably 0.2 to 2 mol/l.

It is particularly preferred to use ethers such as diethyl ether, tetrahydrofuran or dioxan with propanephosphinic anhydride as condensing agent at from $20°$ to $60°$ C.

6. Process for preparing compounds Ia and Ib where $R^2$ is 4,5-dihydro-2-oxazolyl

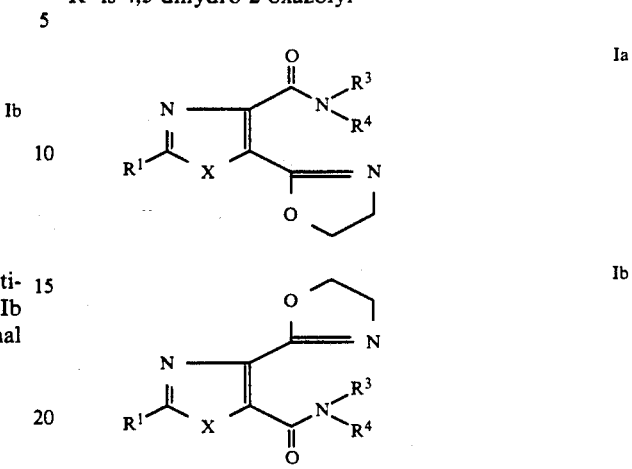

These compounds are obtained by reacting an appropriate carboxylic acid derivative Ia or Ib where $R^2$ is $CO_2R'$ or COOH and R' is $C_1$-$C_4$-alkyl in a conventional manner with an amino alcohol of the formula VIII.

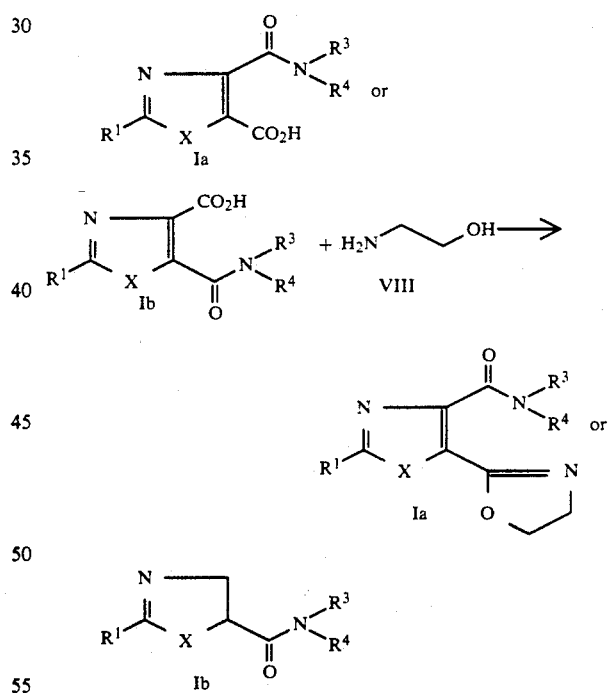

The reaction is carried out at from $0°$ to $180°$ C., preferably at the reflux temperature of the mixture with an amino alcohol VIII, in the presence or absence of an inert solvent. The ratio of ester or carboxylic acid Ia or Ib to amino alcohol VIII in this reaction is from 1:1 to 1:2.5, preferably 1:1 to 1:1.5.

The solvents expediently used are halohydrocarbons such as chlorobenzene and 1,2-dichlorobenzene, ethers, e.g. methyl tert-butyl ether, 1,2-dimethoxyethane, diethylene glycol dimethyl ether, tetrahydrofuran and dioxan; alcohols such as methanol, ethanol, propanol or ethylene glycol, dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolin-2-one, or aromatic compounds, e.g. benzene, toluene and xylene. The concentration of the precursors in these solvents is generally from 0.1 to 5.0 mol/l, preferably 0.2 to 2.0 mol/l.

The reaction is generally complete after 14 hours; the carboxamides Ia and Ib are then precipitated, where appropriate by adding water, filtered off with suction or extracted with an organic solvent, and purified by conventional methods such as recrystallization or chromatography.

Compounds of the formula VIa where $R^1$ is $-ZR^8$ are obtained in a conventional manner (Helv. Chim. Acta, 37 (1954) 2059) by reacting a 2-halothiazole-4-carboxamide VIa (DE 2,241,035) with an alcohol or thiol $H-ZR^8$ in the presence of a base in an inert organic solvent.

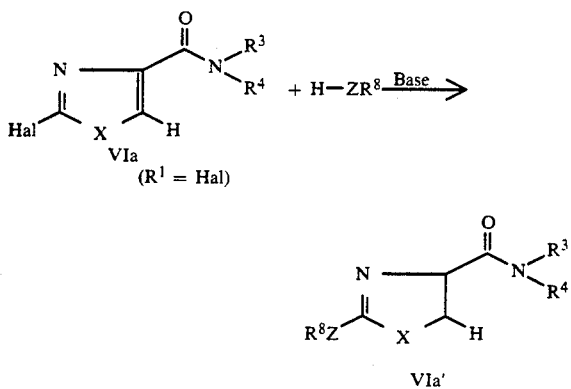

Hal in formula VIa is a halogen such as fluorine, chlorine, bromine or iodine; particularly suitable compounds VIa are those where Hal is chlorine or bromine.

$R^8Z$ in formula VIa' is $C_1-C_4$-alkoxy, $C_1-C_4$-alkylthio, each of which can be substituted up to three times by halogen, in particular methoxy, ethoxy, 1-methylethoxy, 1,1-dimethylethoxy, trifluoromethoxy, methylthio, ethylthio, difluoromethylthio; or phenoxy or phenylthio, each of which can be substituted up to three times by $C_1-C_4$-alkyl, $C_1-C_4$-haloalkyl, $C_1-C_4$-alkylthio, $C_1-C_4$-haloalkylthio, halogen, cyano or nitro, in particular 2,4-dichlorophenoxy, 2,4-difluorophenoxy, 2,4,6-trifluorophenoxy, p-trifluoromethylphenoxy, 2-chloro-4-trifluorophenoxy, 3-cyanophenoxy, 4-cyano-2-methoxyphenoxy, 4-nitrophenoxy, 2-fluorophenylthio, 4-trifluoromethylphenylthio and 3-cyanophenylthio.

The solvents expediently used for these reactions are halohydrocarbons, e.g. tetrachloroethane, methylene chloride, chloroform, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxan; dipolar aprotic solvents, e.g. acetonitrile, dimethylformamide, dimethylacetamide, dimethyl sulfoxide, N-methylpyrrolidone, 1,3-dimethyltetrahydro-2(1H)-pyrimidinone and 1,3-dimethylimidazolidin-2-one; aromatic compounds, e.g. benzene, toluene, xylene, pyridine and quinoline; ketones, e.g. acetone, methyl ethyl ketone; alcohols, e.g. methanol, ethanol, iso-propanol and tert-butanol or mixtures thereof.

The reaction can be carried out at from $-100°$ C. to the reflux temperature of the solvent or mixture thereof, preferably at from $-60°$ C. to $150°$ C.

The bases used are hydrides and alkoxides of alkali metals and alkaline earth metals, in particular NaH, KH, $CaH_2$, LiH and KO-tBu. It is also beneficial on occasion to use combinations of the bases listed.

The molar ratios of the starting compounds in the reaction are generally from 3:1 to 1:1 for the ratio of alcohol or thiol to 2-halothiazole-4-carboxamide VIa and from 1:1 to 1:3 for the ratio of alcohol or thiol to the base.

The concentration of the precursors in the solvent is generally from 0.1 to 5 mol/l, preferably 0.2 to 2 mol/l.

It is particularly preferable to use aprotic dipolar solvents such as acetonitrile, dimethylformamide, dimethyl sulfoxide, N-methylpyrrolidone, 1,3-dimethyltetrahydro-2(1H)-pyrimidinone and 1,3-dimethylimidazolidin-2-one or ethers such as 1,2-dimethoxyethane, diethylene glycol dimethyl ether, tetrahydrofuran or dioxan at from $50°$ C. to $150°$ C. with NaH or KO-tBu as base.

The 2-halothiazole-4-carboxamides of the formula VIa required for the reaction can be obtained by methods known from the literature from the corresponding carbonyl halides by reaction with amines (DE-A 2,241,035).

The alcohols or thiols which are used are commercially available in many cases or they can be prepared in a conventional manner.

Furthermore, the compounds of the formula VIb are obtained in a conventional manner (Helv. Chim. Acta, 37, (1954) 2059) by reacting a 2-halothiazole-5-carboxamide VIb with an alcohol or thiol in an inert organic solvent in the presence of a base as shown in the scheme:

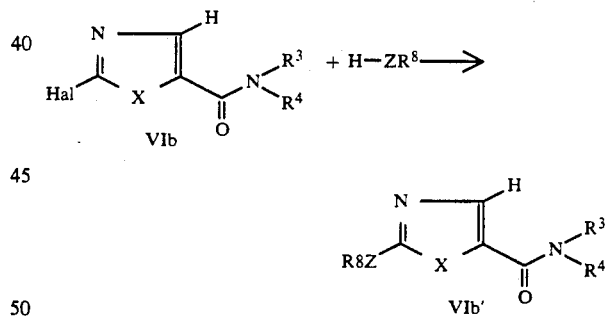

Hal in VIb is a halogen such as fluorine, chlorine, bromine or iodine; particularly suitable compounds Vib are those where Hal is chlorine or bromine.

$R^8Z$ in formula Vib' is $C_1-C_4$-alkoxy, $C_1-C_4$-alkylthio, each of which can be substituted up to three times by halogen, in particular methoxy, ethoxy, 1-methylethoxy, 1,1-dimethylethoxy, trifluoromethoxy, methylthio, ethylthio, difluoromethylthio; or phenoxy or phenylthio, each of which can be substituted up to three times by $C_1-C_4$-alkyl, $C_1-C_4$-haloalkyl, $C_1-C_4$-alkylthio, $C_1-C_4$-halo-alkylthio, halogen, cyano or nitro, in particular 2,4-dichlorophenoxy, 2,4-difluorophenoxy, 2,4,6-trifluorophenoxy, p-trifluoromethylphenoxy, 2-chloro-4-trifluorophenoxy, 3-cyanophenoxy, 4-cyano-2-methoxyphenoxy, 4-nitrophenoxy, 2-fluorophenylthio, 4-tirfluoromethylphenylthio and 3-cyanophenylthio.

The solvents expediently used for these reactions are halohydrocarbons, e.g. tetrachloroethane, methylene chloride, chloroform, dichloroethane, chlorobenzene and 1,2-dichlorobenzene; ethers, e.g. diethyl ether, methyl tert-butyl ether, dimethoxyethane, diethylene glycol dimethyl ether, tetrahydrofuran and dioxan; dipolar aprotic solvents, e.g. acetonitrile, dimethylformamide, dimethylacetamide, dimethyl sulfoxide, N-methylpyrolidone, 1,3-dimethyltetrahydro-2(1H)-pyrimidinone and 1,3-dimethylimidazolidin-2-one; aromatic compounds, e.g. benzene, toluene, xylene, pyridine and quinoline; ketones, e.g. acetone, methyl ethyl ketone; alcohols, e.g. methanol, ethanol, iso-propanol and tert-butanol or mixtures thereof.

The reaction can be carried out at from −100° C. to the reflux temperature of the solvent or mixture thereof, preferably at from −60° C. to 150° C.

The bases used are hydrides and alkoxides of alkali metals and alkaline earth metals, in particular NaH, KH, $CaH_2$, LiH and KO-tBu. It is also beneficial on occasion to use combinations of the bases listed.

The molar ratios of the starting compounds in the reaction are generally from 3:1 to 1:1 for the ratio of alcohol or thiol to 2-halothiazole-5-carboxamide Vib and from 1:1 to 1:3 for the ratio of alcohol or thiol to the base.

The concentration of the precursors in the solvent is generally from 0.1 to 5 mol/l, preferably 0.2 to 2 mol/l.

It is particularly preferable to use aprotic dipolar solvents such as acetonitrile, dimethylformamide, dimethyl sulfoxide, N-methylpyrrolidone, 1,3-dimethyltetrahydro-2(1H)-pyrimidinone and 1,3-dimethylimidazolidin-2-one or ethers such as 1,2-dimethoxyethane, diethylene glycol dimethyl ether, tetrahydrofuran or dioxan at from 50° to 150° C. with NaH or KO-tBu as base.

The 2-halothiazole-5-carboxamides of the formula Vib required for the reaction can be obtained by methods known from the literature from the corresponding carbonyl halides by reaction with amines (U.S. Pat. No. 4,001,421)

Compounds of the formula Ib can be obtained by reacting dicarboxylic esters of the formula II with amines in a conventional manner, and hydrolyzing the resulting amides Ib as shown in the scheme:

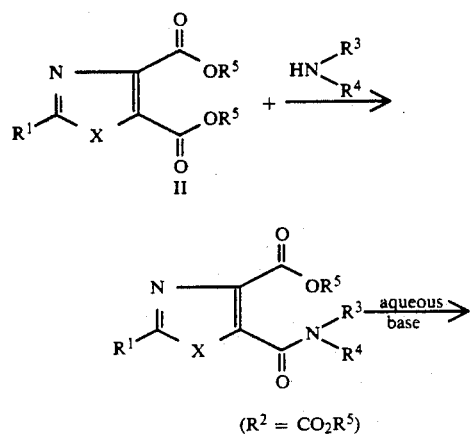

($R^2 = CO_2R^5$)

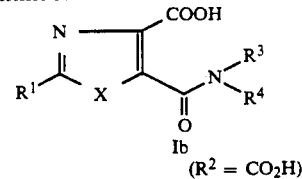

($R^2 = CO_2H$)

The procedure for this is expediently to dissolve the diester II in an inert organic solvent and react with an amine.

The solvents used for these reactions are ethers, e.g. diethyl ether, methyl tert-butyl ether, dimethoxyethane, diethylene glycol dimethyl ether, tetrahydrofuran and dioxan; aromatic compounds, e.g. benzene, toluene, xylene or mesitylene; alcohols, e.g. methanol, ethanol, iso-propanol and tert-butanol, or mixtures thereof.

The reaction can be carried out at from −100° C. to the reflux temperature of the solvent or mixture thereof, preferably at from −60° C. to 150° C.

The molar ratio of diester II to amine is from 1:1 to 1:2, preferably from 1:1 to 1:1.2.

The concentration of the precursors in the solvent is generally from 0.1 to 5 mol/l, preferably 0.2 to 2.0 mol/l.

It is particularly preferable to use alcohols such as ethanol in the presence of one equivalent of amine at from 50° to 100° C. The diesters II required for the reaction are known from the literature or can be prepared by conventional methods (Bull. Soc. Chim. Fr., 1969, 1762; J. Chem. Soc., 1953, 93).

Besides Processes 1-6 which have been described above for preparing compounds Ia and Ib, there are further possible syntheses which can be found in the following references:

Beilstein, main series and supplements 1-5, volume 27; R. W. Wiley, The Chemistry of Heterocyclic Compounds, Five- and Six-Membered Compounds with Nitrogen and Oxygen, Interscience Publishers, New York, London (1962), Heterocyclic Chemistry, Vol. 6, Five-Membered Rings with Two or More Oxygen, Sulfur or Nitrogen Atoms, Pergamon Press, 1984, J. March, Advanced Organic Chemistry, third edition, John Wiley and Sons, 1985, Houben-Weyl, Methoden der organischen Chemie, 4th edition, Thieme Verlag, volumes IV, VI, VII, VIII and X.

With a view to the intended use of the compounds Ia' and Ib', the following substituents are preferred:

X is oxygen or sulfur $R^1$ is hydrogen; halogen such as fluorine, chlorine, bromine and iodine, especially fluorine and chlorine; $C_1$-$C_6$-alkyl, such as methyl, ethyl, n-propyl, iso-propyl, n-butyl, sec-butyl, iso-butyl and tert-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, especially methyl, ethyl, propyl and iso-propyl, which can carry from one to five halogen atoms, in particular fluorine and/or chlorine or one or two of the following: cycloalkyl such as cyclopropyl, cyclobutyl, cyclopentyl and cyclohexyl, especially cyclopropyl;

alkoxy such as methoxy, ethoxy, n-propoxy, 2-methylethoxy, n-butoxy, 1-methylpropoxy, 2-methylpropoxy and 1,1-dimethylethoxy, especially methoxy, ethoxy, 1-methylethoxy and 1,1-dimethylethoxy; haloalkoxy such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, especially trifluoromethoxy and pentafluoroethoxy; alkylthio such as methylthio, ethylthio, propylthio, 1-methylethylthio, butylthio, 1-methylpropylthio, 2-methylpropylthio and 1,1-dimethylethylthio, especially methylthio and ethylthio; haloalkylthio such as difluoromethylthio, trifluoromethylthio, chlorodifluoromethylthio, 1-fluoroethylthio, 2-fluoroethylthio, 2,2-difluoroethylthio, 2,2,2-trifluoroethylthio, 2-chloro-2,2-difluoroethylthio, 2,2-dichloro-2-fluoroethylthio, 2,2,2-trichloroethylthio and pentafluoroethylthio, especially difluromethylthio and pentafluoroethylthio or cyano; benzyl which can carry from one to three of the following: alkyl as mentioned above, especially methyl, ethyl and iso-propyl; haloalkyl as mentioned above, especially trifluoromethyl and chlorodifluoromethyl; alkoxy as mentioned above, especially methoxy and ethoxy; haloalkoxy as mentioned above, especially trifluoromethoxy, pentafluoroethoxy and trichloromethoxy; alkylthio as mentioned above, especially methylthio and ethylthio; haloalkylthio as mentioned above, especially difluoromethylthio, pentafluoroethylthio and trifluoromethylthio; halogen as mentioned above, especially fluorine and chlorine; cyano or nitro; cycloalkyl such as cyclopropyl, cyclobutyl, cyclopentyl, cyclohexyl, cycloheptyl and cyclooctyl, especially cyclopropyl, cyclopentyl and cyclohexyl, which can carry from one to three of the following: alkyl as mentioned above, especially methyl, or halogen as mentioned above, especially chlorine and fluorine; alkenyl such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, especially allyl which can carry from one to three of the following: halogen as mentioned above, especially fluorine and chlorine; alkoxy as mentioned above, especially methoxy and ethoxy, and/or one phenyl which in turn can carry from one to three of the following: alkyl as mentioned above, especially methyl, ethyl and iso-propyl; haloalkyl as mentioned above, especially trifluoromethyl and chlorodifluoromethyl; alkoxy as mentioned above, especially methoxy and ethoxy; haloalkoxy as mentioned above, especially trifluoromethoxy, pentafluoroethoxy and trichloromethoxy; alkylthio as mentioned above, especially ethylthio and ethylthio; haloalkylthio as mentioned above, especially difluoromethylthio, pentafluoroethylthio and trifluoromethylthio; halogen as mentioned above, especially fluorine and chlorine; cyano or nitro; alkynyl such as ethynyl, 1-propynyl, propargyl, 1-butynyl, 2-butynyl, 3-butynyl, 1-methyl-2-propynyl, 1-pentynyl, 2-pentynyl, 3-pentynyl, 4-pentynyl, 1-methyl-3-butynyl, 2-methyl-3-butynyl, 1-methyl-2-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-4-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, especially propargyl, which can carry from one to three of the following: halogen as mentioned above, especially iodine; alkoxy as mentioned above, especially methoxy and ethoxy, and/or one phenyl which in turn can carry from one to three of the following: alkyl as mentioned above, especially methyl, ethyl and iso-propyl; haloalkyl as mentioned above, especially trifluoromethyl and chlorodifluoromethyl; alkoxy as mentioned above, especially methoxy and ethoxy; haloalkoxy as mentioned above, especially trifluoromethoxy, pentafluoroethoxy and trichloromethoxy; alkylthio as mentioned above, especially methylthio and ethylthio; haloalkylthio as mentioned above, especially difluoromethylthio, pentafluoroethylthio and trifluoromethylthio; halogen as mentioned above, especially fluorine and chlorine; cyano or nitro; $C_1$–$C_4$-alkoxy as mentioned above, especially methoxy and ethoxy; $C_1$–$C_4$-haloalkoxy as mentioned above, especially trifluoromethoxy, pentafluoroethoxy and trichloromethoxy; $C_1$–$C_4$-alkylthio as mentioned above, especially methylthio and ethylthio; $C_1$–$C_4$-haloalkylthio as mentioned above, especially difluoromethylthio, pentafluoroethylthio and trifluoromethylthio; phenoxy or phenylthio, each of which can carry from one to three of the following: alkyl as mentioned above, especially methyl, ethyl and iso-propyl; haloalkyl as mentioned above, especially trifluoromethyl and chlorodifluoromethyl; alkoxy as mentioned above, especially methoxy and ethoxy; haloalkoxy as mentioned above, especially trifluoromethoxy, pentafluoroethoxy and trichloromethoxy; alkylthio as mentioned above, especially methylthio and ethylthio; haloalkylthio as mentioned above, especially difluoromethylthio, pentafluoroethylthio and trifluoromethylthio; halogen as mentioned above, especially fluorine and chlorine; cyano or nitro; a 5- to 6-membered heterocyclic radical containing one or two hetero atoms selected from the group comprising oxygen, sulfur and nitrogen, such as 2-tetrahydrofuryl, 3-tetrahydrofuryl, 4-tetrahydropyranyl, 2-tetrahydropyranyl, 3-tetrahydropyranyl, 3-furyl, 2-thienyl, 3-thienyl, 2-furyl, 3-tetrahydrothienyl, 2-tetrahydropyranyl, 5-isoxazoyl, 3-isoxazolyl, 4-isoxazolyl, 5-isothiazolyl, 4-isothiazolyl, 3-isothiazolyl, 2-oxazolyl, 4-thiazolyl, 4-oxazolyl, 2-thiazolyl, 5-oxazolyl, 5-thiazolyl, 2-imidazolyl, 4-imidazolyl, 5-imidazolyl, 3-pyrrolyl, 2-pyrrolyl, 3-pyrazolyl, 4-pyrazolyl, 5-pyrazolyl, 4-pyridyl, 3-pyridyl and 2-pyridyl, it being possible for this ring to carry one or two of the following: alkyl as mentioned above, especially methyl; halogen as mentioned above, especially fluorine and chlorine; alkoxy as mentioned above, especially methoxy and ethoxy, or alkoxycarbonyl such as methoxycarbonyl and ethoxycarbonyl, especially methoxycarbonyl; phenyl which can carry from one to three of the following: alkyl as mentioned for $R^1$, especially methyl, ethyl and iso-propyl; haloalkyl as mentioned above, especially trifluoromethyl and chlorodifluoromethyl; alkoxy as mentioned above, especially methoxy and ethoxy; haloalkoxy as mentioned above, especially trifluoromethoxy, pentafluoroethoxy and trichloromethoxy; alkylthio as mentioned above, especially methylthio and ethylthio; haloalkylthio as mentioned above, especially difluoromethylthio, pentafluoroethylthio and trifluoromethylthio; halogen as mentioned above, especially fluorine and chlorine; cyano or nitro;

$R^2$ is formyl, 4,5-dihydro-2-oxazolyl or —$COYR^5$ and Y is oxygen or sulfur;

$R^5$ is hydrogen; alkyl as mentioned for $R^1$, especially methyl, ethyl, n-propyl, iso-propyl, and n-hexyl, which can carry from one to five halogen atoms as mentioned for $R^1$, especially fluorine and chlorine, or hydroxyl groups and/or one of the following: alkoxy as mentioned for $R^1$, especially methoxy and ethoxy; alkoxyalkoxy such as methoxyethoxy, ethoxyethoxy, propoxyethoxy, especially methoxyethoxy; cyano; trimethylsilyl; alkylthio as mentioned for $R^1$, especially methylthio and ethylthio; alkylamino such as methylamino, ethylamino, propylamino, iso-propylamino, especially methylamino and ethylamino; dialkylamino such as dimethylamino, diethylamino, dipropylamino, diisopropylamino, methylethylamino, especially dimethylamino and methylethylamino; cycloalkylamino such as cyclopropylamino, cyclobutylamino, cyclopentylamino, cyclohexylamino and cycloheptylamino, especially cyclopropylamino; alkylsulfinyl such as methylsulfinyl, ethylsulfinyl, propylsulfinyl, iso-propylsulfinyl, especially methylsulfinyl and ethylsulfinyl; alkylsulfonyl such as methylsulfonyl, ethylsulfonyl, propylsulfonyl, iso-propylsulfonyl, especially methylsulfonyl and ethylsulfonyl; carboxy; alkoxycarbonyl as mentioned for $R^1$, especially methoxycarbonyl; dialkylaminocarbonyl such as dimethylaminocarbonyl, diethylaminocarbonyl, dipropylaminocarbonyl, diisopropylaminocarbonyl, dicyclopropylaminocarbonyl, methylethylaminocarbonyl, especially dimethylaminocarbonyl and diethylaminocarbonyl; dialkoxyphosphoryl such as dimethoxyphosphoryl, diethoxyphosphoryl, dipropoxyphosphoryl, diisopropoxyphosphoryl, especially dimethoxyphosphoryl and diethoxyphosphoryl; alkaneiminoxy such as, in particular, 2-propaneiminoxy; thienyl, furyl, tetrahydrofuryl, phthalimido, pyridyl, benzyloxy; benzoyl, it being possible for the cyclic radicals in turn to carry from one to three of the following: alkyl as mentioned for $R^1$, especially methyl and ethyl; alkoxy as mentioned for $R^1$, especially methoxy and ethoxy, or halogen as mentioned for $R^1$, especially fluorine and chlorine; benzyl which can carry from one to three of the following: alkyl as mentioned for $R^1$, especially methyl and ethyl; alkoxy as mentioned for $R^1$, especially methoxy and ethoxy; haloalkyl as mentioned for $R^1$, especially trifluoromethyl; halogen as mentioned for $R^1$, especially fluorine and chlorine, nitro and cyano; $C_3$-$C_8$-cycloalkyl as mentioned for $R^1$, especially cyclopentyl and cyclohexyl; phenyl which can carry from one to three of the following: alkyl as mentioned for $R^1$, especially methyl and ethyl; alkoxy as mentioned for $R^1$, especially methoxy and ethoxy; haloalkyl as mentioned for $R^1$, especially trifluoromethyl; haloalkoxy as mentioned for $R^1$, especially trifluoromethoxy; alkoxycarbonyl as mentioned above, especially methoxycarbonyl; halogen as mentioned for $R^1$, especially fluorine and chlorine and bromine, nitro and cyano; $C_3$-$C_6$-alkenyl as mentioned for $R^1$, especially allyl and methallyl, $C_5$-$C_6$-cycloalkenyl such as 2-cyclopentenyl and 2-cyclohexenyl, especially 2-cyclohexenyl, or $C_3$-$C_6$-alkynyl as mentioned for $R^1$, especially propargyl, it being possible for these radicals to carry one of the following: hydroxy; alkoxy as mentioned for $R^1$, especially methoxy and ethoxy; halogen as mentioned for $R^1$, especially iodine, or phenyl which in turn can carry from one to three of the following: alkyl as mentioned for $R^1$, especially methyl and ethyl; alkoxy as mentioned for $R^1$, especially methoxy and ethoxy; haloalkyl as mentioned for $R^1$, especially trifluoromethyl; halogen as mentioned for $R^1$, especially fluorine and chlorine, nitro or cyano; a five- to six-membered heterocyclic radical containing one or two hetero atoms selected from the group comprising oxygen, sulfur and nitrogen as mentioned for $R^1$, especially tetrahydrofuryl and tetrahydropyranyl or a benzotriazolyl radical; phthalimido; tetrahydrophthalimido; succinimido; maleimido; one equivalent of a cation of an alkali metal or alkaline earth metal, manganese, copper, iron, ammonium or substituted ammonium, or —$N{=}CR^6R^7$ where $R^6$ and $R^7$ are, independently of one another, hydrogen, alkyl as mentioned for $R^1$, especially methyl, ethyl and iso-propyl; cycloalkyl as mentioned for $R^1$, especially cyclopropyl; phenyl or furyl, or together form a methylene chain —$(CH_2)_m$— with m=4 to 7, $R^3$ is hydrogen, $C_1$-$C_6$-alkyl as mentioned for $R^1$, especially methyl, ethyl or iso-propyl, which can carry from one to three of the following: hydroxyl; halogen as mentioned for $R^1$, especially fluorine and chlorine; alkoxy as mentioned for $R^1$, especially methoxy and ethoxy; alkylthio as mentioned for $R^1$, especially methylthio and ethylthio, or dialkylamino as mentioned for $R^5$, especially dimethylamino; cycloalkyl as mentioned for $R^1$, especially cyclopropyl, cyclobutyl, cyclopentyl and cyclohexyl, which can carry from one to three of the following: alkyl as mentioned for $R^1$, especially methyl, ethyl and isopropyl; halogen as mentioned for $R^1$, especially fluorine and chlorine, or haloalkyl as mentioned for $R^1$, especially trifluoromethyl;

$R^4$ is hydroxyl; alkoxy as mentioned for $R^1$, especially methoxy and ethoxy; alkyl as mentioned for $R^1$, especially methyl, ethyl, n-propyl, iso-propyl, n-butyl, sec-butyl, iso-butyl and tert-butyl, which can carry from one to three of the following: alkoxy as mentioned for $R^1$, especially methoxy and ethoxy; haloalkoxy as mentioned for $R^1$, especially trifluoromethoxy; alkylthio as mentioned for $R^1$, especially methylthio and ethylthio; haloalkylthio as mentioned for $R^1$, especially trifluoromethylthio; dialkylamino as mentioned for $R^1$, especially dimethylamino and diethylamino; halogen as mentioned for $R^1$, especially fluorine and chlorine; cycloalkyl as mentioned for $R^1$, especially cyclopropyl, cyclopentyl and cyclohexyl, or phenyl which in turn can carry from one to three of the following: halogen as mentioned for $R^1$, especially fluorine and chlorine; cyano; nitro; alkyl as mentioned for $R^1$, especially methyl and ethyl; haloalkyl as mentioned for $R^1$, especially trifluoromethyl, alkoxy as mentioned for $R^1$, especially methoxy and ethoxy; haloalkoxy as mentioned for $R^1$, especially trifluoromethoxy; alkylthio as mentioned for $R^1$, especially methylthio and ethylthio, or haloalkylthio as mentioned for $R^1$, especially trifluoromethylthio; cycloalkyl as mentioned for $R^1$, especially cyclopropyl, cyclobutyl, cyclopentyl and cyclohexyl, which can carry from one to three of the following: alkyl as mentioned for $R^1$, especially methyl, ethyl and isopropyl; haloalkyl as mentioned for $R^1$, especially trifluoromethyl; alkoxy as mentioned for $R^1$, especially methoxy and ethoxy; haloalkoxy as mentioned for $R^1$, especially trifluoromethoxy; halogen as mentioned for $R^1$, especially fluorine and chlorine, nitro or cyano; alkenyl or $C_3$-$C_6$-alkynyl as mentioned for $R^1$, especially allyl, methallyl, propargyl and 1,1-dimethyl-2-propynyl, which can be substituted from once to three times by halogen as mentioned for $R^1$, especially fluorine and chlorine, and/or once by phenyl which in turn can carry from one to three of the following: alkyl as mentioned for $R^1$, especially methyl and ethyl; haloalkyl as mentioned for $R^1$, especially trifluoromethyl; alkoxy as mentioned for $R^1$, especially methoxy and ethoxy, haloalkoxy as mentioned for $R^1$, especially trifluormethoxy; alkylthio as mentioned for $R^1$, especially methylthio and ethylthio; haloalkylthio as mentioned for $R^1$, especially trifluoromethylthio; halogen as mentioned for $R^1$, especially fluorine and chlorine, cyano or nitro; a 5- to 6-membered heterocyclic radical which contains one or two hetero atoms selected from the group comprising oxygen, sulfur or nitrogen as mentioned for $R^1$ and which can carry from one to three of the following: alkyl as mentioned for $R^1$, especially methyl, ethyl and iso-propyl, or halogen as mentioned for $R^1$, especially fluorine and chlorine; phenyl which can carry from one to four of the following: alkyl as mentioned for $R^1$, especially methyl, ethyl and iso-propyl; haloalkyl as mentioned for $R^1$, especially trifluoromethyl; alkoxy as mentioned for $R^1$, especially methoxy and ethoxy; haloalkoxy as mentioned for $R^1$, especially trifluoromethoxy; alkylthio as mentioned for $R^1$, especially methylthio and ethylthio; haloalkylthio as mentioned for $R^1$, especially trifluoromethylthio; halogen as mentioned for $R^1$, especially fluorine and chlorine; nitro; cyano; formyl; alkanoyl such as acetyl, propionyl, butyryl, especially acetyl; haloalkanoyl such as trifluoroacetyl, trichloroacetyl, pentafluoropropionyl, especially trifluoroacetyl, or alkoxycarbonyl as mentioned for $R^1$, especially methoxycarbonyl; naphthyl which can be substituted from once to three times by alkyl as mentioned for $R^1$, especially methyl and ethyl, or halogen as mentioned for $R^1$, especially fluorine and chlorine, or $R^3$ and $R^4$ can together form $-(CH_2)_n-Y_p-(CH_2)_q-$, where n and q are each 1, 2 or 3, p is 0 or 1 and Y is oxygen, sulfur or N-methyl, such as $-(CH_2)_3-$, $-(CH_2)_4-$, $-(CH_2)_5-$, $-(CH_2)_6-$ $-CH_2-O-CH_2-$, $-CH_2-CH_2-O-CH_2-CH_2-$, $-CH_2-S-CH_2-$, $-CH_2-CH_2-S-CH_2-CH_2-$, $-CH_2-CH_2-N(CH_3)-CH_2-CH_2-$, especially $-(CH_2)_5-$ and $-CH_2-CH_2-O-CH_2-CH_2-$, or $-(CH_2)_3-CO-$; and the environmentally compatible salts thereof.

Particularly preferred compounds Ia' and Ib' are those in which $R^3$ is hydrogen and those in which:

$R^1$ is hydrogen; methyl, ethyl, propyl, 1-methylethyl, butyl, 1-methylpropyl, 2-methylpropyl and 1,1-dimethylethyl; methoxy, ethoxy, propyloxy, 1-methylethoxy, butyloxy, 1-methylpropyloxy, 2-methylpropyloxy and 1,1-dimethylethoxy; difluoromethoxy and trifluoromethoxy; methylthio, ethylthio, propylthio, 1-methylethylthio, butylthio, 1-methylpropylthio, 2-methylpropylthio and 1,1-dimethylethylthio; difluoromethylthio and trifluoromethylthio;

$R^2$ is $-COYR^5$; $R^5$ is hydrogen; phthalimido; succinimido; maleimido or $-N=CR^6R^7$; $R^6$ and $R^7$ are each hydrogen; methyl, ethyl, propyl, 1-methylethyl, butyl, 1-methylpropyl, 2-methylpropyl and 1,1-dimethylethyl; cyclopropyl, cyclopentyl, cyclohexyl and cycloheptyl; or together form a 4- to 7-membered alkylene chain such as $-CH_2CH_2CH_2CH_2-$, $-CH_2CH_2CH_2CH_2CH_2-$, $-CH_2CH_2CH_2CH_2CH_2CH_2-$ and $-CH_2CH_2CH_2CH_2CH_2CH_2CH_2-$;

$R^3$ and $R^4$ are each methyl, ethyl, propyl, 1-methylethyl, butyl, 1-methylpropyl, 2-methylpropyl and 1,1-dimethylethyl; cyclopropyl, cyclopentyl, cyclohexyl and cycloheptyl; or together form a 4- to 7-membered alkylene chain such as $-CH_2CH_2CH_2CH_2-$, $-CH_2CH_2CH_2CH_2CH_2-$, $-CH_2CH_2CH_2CH_2CH_2CH_2-$ and $-CH_2CH_2CH_2CH_2CH_2CH_2CH_2-$;

Examples of very active compounds of the formulae Ia and Ib are listed in the Tables which follow:

TABLE A

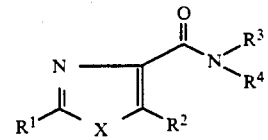

(X = O or S)

| $R^1$ | $R^2$ | $R^3$ | $R^4$ |
|---|---|---|---|
| H | COOH | H | tert.-butyl |
| F | COOH | H | tert.-butyl |
| Cl | COOH | H | tert.-butyl |
| methyl | COOH | H | tert.-butyl |
| ethyl | COOH | H | tert.-butyl |
| n-propyl | COOH | H | tert.-butyl |
| iso-propyl | COOH | H | tert.-butyl |
| n-butyl | COOH | H | tert.-butyl |
| iso-butyl | COOH | H | tert.-butyl |
| sec.-butyl | COOH | H | tert.-butyl |
| tert.-butyl | COOH | H | tert.-butyl |
| cyclo-propyl | COOH | H | tert.-butyl |
| cyclo-butyl | COOH | H | tert.-butyl |
| cyclo-pentyl | COOH | H | tert.-butyl |
| cyclo-hexyl | COOH | H | tert.-butyl |
| cyclo-heptyl | COOH | H | tert.-butyl |
| cyclo-octyl | COOH | H | tert.-butyl |
| 1-methylcyclopropyl | COOH | H | tert.-butyl |
| trifluoromethyl | COOH | H | tert.-butyl |
| chlorodifluoromethyl | COOH | H | tert.-butyl |
| pentafluoroethyl | COOH | H | tert.-butyl |
| methoxymethyl | COOH | H | tert.-butyl |
| 1-methylmethoxymethyl | COOH | H | tert.-butyl |
| 1-methylmethoxyethyl | COOH | H | tert.-butyl |
| ethoxymethyl | COOH | H | tert.-butyl |
| vinyl | COOH | H | tert.-butyl |
| allyl | COOH | H | tert.-butyl |
| methallyl | COOH | H | tert.-butyl |
| crotyl | COOH | H | tert.-butyl |
| ethynyl | COOH | H | tert.-butyl |
| propargyl | COOH | H | tert.-butyl |
| phenylethynyl | COOH | H | tert.-butyl |
| methoxy | COOH | H | tert.-butyl |

TABLE A-continued

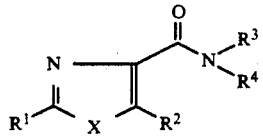

(X = O or S)

| R¹ | R² | R³ | R⁴ |
|---|---|---|---|
| ethoxy | COOH | H | tert.-butyl |
| trifluoromethoxy | COOH | H | tert.-butyl |
| methylthio | COOH | H | tert.-butyl |
| trifluoromethylthio | COOH | H | tert.-butyl |
| phenoxy | COOH | H | tert.-butyl |
| 4-Cl-phenoxy | COOH | H | tert.-butyl |
| 2,4-(Cl,Cl)-phenoxy | COOH | H | tert.-butyl |
| 4-CF₃-phenoxy | COOH | H | tert.-butyl |
| phenyl | COOH | H | tert.-butyl |
| 2-F-phenylthio | COOH | H | tert.-butyl |
| 3-F-phenyl | COOH | H | tert.-butyl |
| 2,4-(F,F)-phenyl | COOH | H | tert.-butyl |
| 2-Cl-phenyl | COOH | H | tert.-butyl |
| 3-Cl-phenyl | COOH | H | tert.-butyl |
| 2,4-(Cl,Cl)-phenyl | COOH | H | tert.-butyl |
| 2-CH₃-phenyl | COOH | H | tert.-butyl |
| 3-CH₃-phenyl | COOH | H | tert.-butyl |
| 4-CH₃-phenyl | COOH | H | tert.-butyl |
| 2,4-(CH₃,CH₃)-phenyl | COOH | H | tert.-butyl |
| 2,4,6-(CH₃,CH₃,CH₃)-phenyl | COOH | H | tert.-butyl |
| 2-CF₃-phenyl | COOH | H | tert.-butyl |
| 2-OCH₃-phenyl | COOH | H | tert.-butyl |
| 2,4-(OCH₃,OCH₃)-phenyl | COOH | H | tert.-butyl |
| 4-OCF₃-phenyl | COOH | H | tert.-butyl |
| 4-SCH₃-phenyl | COOH | H | tert.-butyl |
| 3-SCF₃-phenyl | COOH | H | tert.-butyl |
| 2,4-(NO₂,NO₂)-phenyl | COOH | H | tert.-butyl |
| 4-NO₂-phenyl | COOH | H | tert.-butyl |
| 2-thienyl | COOH | H | tert.-butyl |
| 3-thienyl | COOH | H | tert.-butyl |
| 2-furanyl | COOH | H | tert.-butyl |
| 3-furanyl | COOH | H | tert.-butyl |
| 2-tetrahydrofuranyl | COOH | H | tert.-butyl |
| 3-tetrahydrofuranyl | COOH | H | tert.-butyl |
| 2-pyridyl | COOH | H | tert.-butyl |
| 3-pyridyl | COOH | H | tert.-butyl |
| 4-pyridyl | COOH | H | tert.-butyl |
| 2-tetrahydropyranyl | COOH | H | tert.-butyl |
| 3-tetrahydropyranyl | COOH | H | tert.-butyl |
| 4-tetrahydropyranyl | COOH | H | tert.-butyl |
| iso-propoxy | COOH | H | tert.-butyl |
| H | COOH | H | cyclo-propyl |
| F | COOH | H | cyclo-propyl |
| Cl | COOH | H | cyclo-propyl |
| methyl | COOH | H | cyclo-propyl |
| ethyl | COOH | H | cyclo-propyl |
| n-propyl | COOH | H | cyclo-propyl |
| iso-propyl | COOH | H | cyclo-propyl |
| n-butyl | COOH | H | cyclo-propyl |
| iso-butyl | COOH | H | cyclo-propyl |
| sec.-butyl | COOH | H | cyclo-propyl |
| tert.-butyl | COOH | H | cyclo-propyl |
| cyclo-propyl | COOH | H | cyclo-propyl |
| cyclo-butyl | COOH | H | cyclo-propyl |
| cyclo-pentyl | COOH | H | cyclo-propyl |
| cyclo-hexyl | COOH | H | cyclo-propyl |
| cyclo-heptyl | COOH | H | cyclo-propyl |
| cyclo-octyl | COOH | H | cyclo-propyl |
| 1-methylcyclopropyl | COOH | H | cyclo-propyl |
| trifluoromethyl | COOH | H | cyclo-propyl |
| chlorodifluoromethyl | COOH | H | cyclo-propyl |
| pentafluoroethyl | COOH | H | cyclo-propyl |
| methoxymethyl | COOH | H | cyclo-propyl |
| 1-methylmethoxymethyl | COOH | H | cyclo-propyl |
| 1-methylmethoxyethyl | COOH | H | cyclo-propyl |
| ethoxymethyl | COOH | H | cyclo-propyl |
| vinyl | COOH | H | cyclo-propyl |
| allyl | COOH | H | cyclo-propyl |
| methallyl | COOH | H | cyclo-propyl |
| crotyl | COOH | H | cyclo-propyl |
| ethynyl | COOH | H | cyclo-propyl |

TABLE A-continued

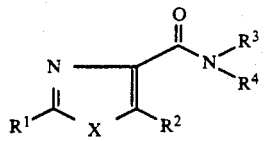

(X = O or S)

| R¹ | R² | R³ | R⁴ |
|---|---|---|---|
| propargyl | COOH | H | cyclo-propyl |
| phenylethynyl | COOH | H | cyclo-propyl |
| methoxy | COOH | H | cyclo-propyl |
| ethoxy | COOH | H | cyclo-propyl |
| trifluoromethoxy | COOH | H | cyclo-propyl |
| methylthio | COOH | H | cyclo-propyl |
| trifluoromethylthio | COOH | H | cyclo-propyl |
| phenoxy | COOH | H | cyclo-propyl |
| 4-Cl-phenoxy | COOH | H | cyclo-propyl |
| 2,4-(Cl,Cl)-phenoxy | COOH | H | cyclo-propyl |
| 4-CF₃-phenoxy | COOH | H | cyclo-propyl |
| phenyl | COOH | H | cyclo-propyl |
| 2-F-phenylthio | COOH | H | cyclo-propyl |
| 3-F-phenyl | COOH | H | cyclo-propyl |
| 2,4-(F,F)-phenyl | COOH | H | cyclo-propyl |
| 2-Cl-phenyl | COOH | H | cyclo-propyl |
| 3-Cl-phenyl | COOH | H | cyclo-propyl |
| 2,4-(Cl,Cl)-phenyl | COOH | H | cyclo-propyl |
| 2-CH₃-phenyl | COOH | H | cyclo-propyl |
| 3-CH₃-phenyl | COOH | H | cyclo-propyl |
| 4-CH₃-phenyl | COOH | H | cyclo-propyl |
| 2,4-(CH₃,CH₃)-phenyl | COOH | H | cyclo-propyl |
| 2,4,6-(CH₃,CH₃,CH₃)-phenyl | COOH | H | cyclo-propyl |
| 2-CF₃-phenyl | COOH | H | cyclo-propyl |
| 2-OCH₃-phenyl | COOH | H | cyclo-propyl |
| 2,4-(OCH₃,OCH₃)-phenyl | COOH | H | cyclo-propyl |
| 4-OCF₃-phenyl | COOH | H | cyclo-propyl |
| 4-SCH₃-phenyl | COOH | H | cyclo-propyl |
| 3-SCF₃-phenyl | COOH | H | cyclo-propyl |
| 2,4-(NO₂,NO₂)-phenyl | COOH | H | cyclo-propyl |
| 4-NO₂-phenyl | COOH | H | cyclo-propyl |
| 2-thienyl | COOH | H | cyclo-propyl |
| 3-thienyl | COOH | H | cyclo-propyl |
| 2-furanyl | COOH | H | cyclo-propyl |
| 3-furanyl | COOH | H | cyclo-propyl |
| 2-tetrahydrofuranyl | COOH | H | cyclo-propyl |
| 3-tetrahydrofuranyl | COOH | H | cyclo-propyl |
| 2-pyridyl | COOH | H | cyclo-propyl |
| 3-pyridyl | COOH | H | cyclo-propyl |
| 4-pyridyl | COOH | H | cyclo-propyl |
| 2-tetrahydropyranyl | COOH | H | cyclo-propyl |
| 3-tetrahydropyranyl | COOH | H | cyclo-propyl |
| 4-tetrahydropyranyl | COOH | H | cyclo-propyl |
| iso-propoxy | COOH | H | cyclo-propyl |
| H | COOH | methyl | tert.-butyl |
| F | COOH | methyl | tert.-butyl |
| Cl | COOH | methyl | tert.-butyl |
| methyl | COOH | methyl | tert.-butyl |
| ethyl | COOH | methyl | tert.-butyl |
| n-propyl | COOH | methyl | tert.-butyl |
| iso-propyl | COOH | methyl | tert.-butyl |
| n-butyl | COOH | methyl | tert.-butyl |
| iso-butyl | COOH | methyl | tert.-butyl |
| sec.-butyl | COOH | methyl | tert.-butyl |
| tert.-butyl | COOH | methyl | tert.-butyl |
| cyclo-propyl | COOH | methyl | tert.-butyl |
| cyclo-butyl | COOH | methyl | tert.-butyl |
| cyclo-pentyl | COOH | methyl | tert.-butyl |
| cyclo-hexyl | COOH | iso-propyl | tert.-butyl |
| cyclo-heptyl | COOH | iso-propyl | tert.-butyl |
| cyclo-octyl | COOH | iso-propyl | tert.-butyl |
| 1-methylcyclopropyl | COOH | iso-propyl | tert.-butyl |
| trifluoromethyl | COOH | iso-propyl | tert.-butyl |
| chlorodifluoromethyl | COOH | iso-propyl | tert.-butyl |
| pentafluoroethyl | COOH | iso-propyl | tert.-butyl |
| methoxymethyl | COOH | iso-propyl | tert.-butyl |
| 1-methylmethoxymethyl | COOH | iso-propyl | tert.-butyl |
| 1-methylmethoxyethyl | COOH | iso-propyl | tert.-butyl |
| ethoxymethyl | COOH | iso-propyl | tert.-butyl |
| vinyl | COOH | iso-propyl | tert.-butyl |
| allyl | COOH | iso-propyl | tert.-butyl |

TABLE A-continued

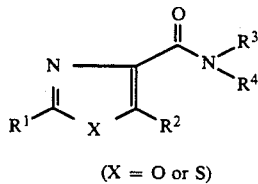

(X = O or S)

| R¹ | R² | R³ | R⁴ |
|---|---|---|---|
| methallyl | COOH | iso-propyl | tert.-butyl |
| crotyl | COOH | iso-propyl | tert.-butyl |
| ethynyl | COOH | iso-propyl | tert.-butyl |
| propargyl | COOH | iso-propyl | tert.-butyl |
| phenylethynyl | COOH | iso-propyl | tert.-butyl |
| methoxy | COOH | iso-propyl | tert.-butyl |
| ethoxy | COOH | iso-propyl | tert.-butyl |
| trifluoromethoxy | COOH | iso-propyl | tert.-butyl |
| H | COOH | methyl | cyclo-propyl |
| F | COOH | methyl | cyclo-propyl |
| Cl | COOH | methyl | cyclo-propyl |
| methyl | COOH | methyl | cyclo-propyl |
| ethyl | COOH | methyl | cyclo-propyl |
| n-propyl | COOH | methyl | cyclo-propyl |
| iso-propyl | COOH | methyl | cyclo-propyl |
| n-butyl | COOH | methyl | cyclo-propyl |
| iso-butyl | COOH | iso-propyl | cyclo-propyl |
| sec.-butyl | COOH | iso-propyl | cyclo-propyl |
| tert.-butyl | COOH | iso-propyl | tert.-butyl |
| cyclo-propyl | COOH | iso-propyl | cyclo-propyl |
| cyclo-butyl | COOH | iso-propyl | cyclo-propyl |
| cyclo-pentyl | COOH | iso-propyl | cyclo-propyl |
| cyclo-hexyl | COOH | methyl | cyclo-propyl |
| cyclo-heptyl | COOH | methyl | cyclo-propyl |
| cyclo-octyl | COOH | methyl | cyclo-propyl |
| 1-methylcyclopropyl | COOH | methyl | cyclo-propyl |
| trifluoromethyl | COOH | methyl | cyclo-propyl |
| chlorodifluoromethyl | COOH | methyl | cyclo-propyl |
| pentafluoroethyl | COOH | methyl | cyclo-propyl |
| methoxymethyl | COOH | iso-propyl | cyclo-propyl |
| 1-methylmethoxymethyl | COOH | iso-propyl | cyclo-propyl |
| 1-methylmethoxyethyl | COOH | iso-propyl | cyclo-propyl |
| ethoxymethyl | COOH | iso-propyl | cyclo-propyl |
| vinyl | COOH | iso-propyl | cyclo-propyl |
| allyl | COOH | iso-propyl | cyclo-propyl |
| methallyl | COOH | iso-propyl | cyclo-propyl |
| crotyl | COOH | methyl | cyclo-propyl |
| ethynyl | COOH | methyl | cyclo-propyl |
| propargyl | COOH | methyl | cyclo-propyl |
| phenylethynyl | COOH | methyl | cyclo-propyl |
| methoxy | COOH | methyl | cyclo-propyl |
| ethoxy | COOH | methyl | cyclo-propyl |
| trifluoromethoxy | COOH | methyl | cyclo-propyl |

TABLE B

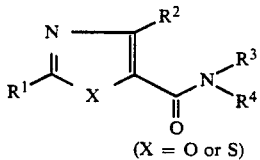

(X = O or S)

| R¹ | R² | R³ | R⁴ |
|---|---|---|---|
| H | COOH | H | tert.-butyl |
| F | COOH | H | tert.-butyl |
| Cl | COOH | H | tert.-butyl |
| methyl | COOH | H | tert.-butyl |
| ethyl | COOH | H | tert.-butyl |
| n-propyl | COOH | H | tert.-butyl |
| iso-propyl | COOH | H | tert.-butyl |
| n-butyl | COOH | H | tert.-butyl |
| iso-butyl | COOH | H | tert.-butyl |
| sec.-butyl | COOH | H | tert.-butyl |
| tert.-butyl | COOH | H | tert.-butyl |
| cyclo-propyl | COOH | H | tert.-butyl |
| cyclo-butyl | COOH | H | tert.-butyl |
| cyclo-pentyl | COOH | H | tert.-butyl |

TABLE B-continued

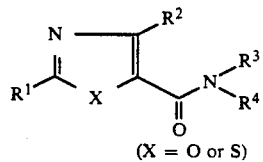

(X = O or S)

| R¹ | R² | R³ | R⁴ |
|---|---|---|---|
| cyclo-hexyl | COOH | H | tert.-butyl |
| cyclo-heptyl | COOH | H | tert.-butyl |
| cyclo-octyl | COOH | H | tert.-butyl |
| 1-methylcyclopropyl | COOH | H | tert.-butyl |
| trifluoromethyl | COOH | H | tert.-butyl |
| chlorodifluoromethyl | COOH | H | tert.-butyl |
| pentafluoroethyl | COOH | H | tert.-butyl |
| methoxymethyl | COOH | H | tert.-butyl |
| 1-methylmethoxymethyl | COOH | H | tert.-butyl |
| 1-methylmethoxyethyl | COOH | H | tert.-butyl |
| ethoxymethyl | COOH | H | tert.-butyl |
| vinyl | COOH | H | tert.-butyl |
| allyl | COOH | H | tert.-butyl |
| methallyl | COOH | H | tert.-butyl |
| crotyl | COOH | H | tert.-butyl |
| ethynyl | COOH | H | tert.-butyl |
| propargyl | COOH | H | tert.-butyl |
| phenylethynyl | COOH | H | tert.-butyl |
| methoxy | COOH | H | tert.-butyl |
| ethoxy | COOH | H | tert.-butyl |
| trifluoromethoxy | COOH | H | tert.-butyl |
| methylthio | COOH | H | tert.-butyl |
| trifluoromethylthio | COOH | H | tert.-butyl |
| phenoxy | COOH | H | tert.-butyl |
| 4-Cl-phenoxy | COOH | H | tert.-butyl |
| 2,4-(Cl,Cl)-phenoxy | COOH | H | tert.-butyl |
| 4-CF₃-phenoxy | COOH | H | tert.-butyl |
| phenyl | COOH | H | tert.-butyl |
| 2-F-phenylthio | COOH | H | tert.-butyl |
| 3-F-phenyl | COOH | H | tert.-butyl |
| 2,4-(F,F)-phenyl | COOH | H | tert.-butyl |
| 2-Cl-phenyl | COOH | H | tert.-butyl |
| 3-Cl-phenyl | COOH | H | tert.-butyl |
| 2,4-(Cl,Cl)-phenyl | COOH | H | tert.-butyl |
| 2-CH₃-phenyl | COOH | H | tert.-butyl |
| 3-CH₃-phenyl | COOH | H | tert.-butyl |
| 4-CH₃-phenyl | COOH | H | tert.-butyl |
| 2,4-(CH₃,CH₃)-phenyl | COOH | H | tert.-butyl |
| 2,4,6-(CH₃,CH₃,CH₃)-phenyl | COOH | H | tert.-butyl |
| 2-CF₃-phenyl | COOH | H | tert.-butyl |
| 2-OCH₃-phenyl | COOH | H | tert.-butyl |
| 2,4-(OCH₃,OCH₃)-phenyl | COOH | H | tert.-butyl |
| 4-OCF₃-phenyl | COOH | H | tert.-butyl |
| 4-SCH₃-phenyl | COOH | H | tert.-butyl |
| 3-SCF₃-phenyl | COOH | H | tert.-butyl |
| 2,4-(NO₂,NO₂)-phenyl | COOH | H | tert.-butyl |
| 4-NO₂-phenyl | COOH | H | tert.-butyl |
| 2-thienyl | COOH | H | tert.-butyl |
| 3-thienyl | COOH | H | tert.-butyl |
| 2-furanyl | COOH | H | tert.-butyl |
| 3-furanyl | COOH | H | tert.-butyl |
| 2-tetrahydrofuranyl | COOH | H | tert.-butyl |
| 3-tetrahydrofuranyl | COOH | H | tert.-butyl |
| 2-pyridyl | COOH | H | tert.-butyl |
| 3-pyridyl | COOH | H | tert.-butyl |
| 4-pyridyl | COOH | H | tert.-butyl |
| 2-tetrahydropyranyl | COOH | H | tert.-butyl |
| 3-tetrahydropyranyl | COOH | H | tert.-butyl |
| 4-tetrahydropyranyl | COOH | H | tert.-butyl |
| iso-propoxy | COOH | H | tert.-butyl |
| H | COOH | H | cyclo-propyl |
| F | COOH | H | cyclo-propyl |
| Cl | COOH | H | cyclo-propyl |
| methyl | COOH | H | cyclo-propyl |
| ethyl | COOH | H | cyclo-propyl |
| n-propyl | COOH | H | cyclo-propyl |
| iso-propyl | COOH | H | cyclo-propyl |
| n-butyl | COOH | H | cyclo-propyl |
| iso-butyl | COOH | H | cyclo-propyl |
| sec.-butyl | COOH | H | cyclo-propyl |
| tert.-butyl | COOH | H | cyclo-propyl |
| cyclo-propyl | COOH | H | cyclo-propyl |

TABLE B-continued

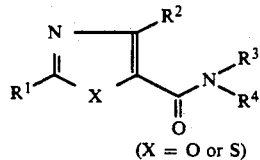

(X = O or S)

| R¹ | R² | R³ | R⁴ |
|---|---|---|---|
| cyclo-butyl | COOH | H | cyclo-propyl |
| cyclo-pentyl | COOH | H | cyclo-propyl |
| cyclo-hexyl | COOH | H | cyclo-propyl |
| cyclo-heptyl | COOH | H | cyclo-propyl |
| cyclo-octyl | COOH | H | cyclo-propyl |
| 1-methylcyclopropyl | COOH | H | cyclo-propyl |
| trifluoromethyl | COOH | H | cyclo-propyl |
| chlorodifluoromethyl | COOH | H | cyclo-propyl |
| pentafluoroethyl | COOH | H | cyclo-propyl |
| methoxymethyl | COOH | H | cyclo-propyl |
| 1-methylmethoxymethyl | COOH | H | cyclo-propyl |
| 1-methylmethoxyethyl | COOH | H | cyclo-propyl |
| ethoxymethyl | COOH | H | cyclo-propyl |
| vinyl | COOH | H | cyclo-propyl |
| allyl | COOH | H | cyclo-propyl |
| methallyl | COOH | H | cyclo-propyl |
| crotyl | COOH | H | cyclo-propyl |
| ethynyl | COOH | H | cyclo-propyl |
| propargyl | COOH | H | cyclo-propyl |
| phenylethynyl | COOH | H | cyclo-propyl |
| methoxy | COOH | H | cyclo-propyl |
| ethoxy | COOH | H | cyclo-propyl |
| trifluoromethoxy | COOH | H | cyclo-propyl |
| methylthio | COOH | H | cyclo-propyl |
| trifluoromethylthio | COOH | H | cyclo-propyl |
| phenoxy | COOH | H | cyclo-propyl |
| 4-Cl-phenoxy | COOH | H | cyclo-propyl |
| 2,4-(Cl,Cl)-phenoxy | COOH | H | cyclo-propyl |
| 4-CF₃-phenoxy | COOH | H | cyclo-propyl |
| phenyl | COOH | H | cyclo-propyl |
| 2-F-phenylthio | COOH | H | cyclo-propyl |
| 3-F-phenyl | COOH | H | cyclo-propyl |
| 2,4-(F,F)-phenyl | COOH | H | cyclo-propyl |
| 2-Cl-phenyl | COOH | H | cyclo-propyl |
| 3-Cl-phenyl | COOH | H | cyclo-propyl |
| 2,4-(Cl,Cl)-phenyl | COOH | H | cyclo-propyl |
| 2-CH₃-phenyl | COOH | H | cyclo-propyl |
| 3-CH₃-phenyl | COOH | H | cyclo-propyl |
| 4-CH₃-phenyl | COOH | H | cyclo-propyl |
| 2,4-(CH₃,CH₃)-phenyl | COOH | H | cyclo-propyl |
| 2,4,6-(CH₃,CH₃,CH₃)-phenyl | COOH | H | cyclo-propyl |
| 2-CF₃-phenyl | COOH | H | cyclo-propyl |
| 2-OCH₃-phenyl | COOH | H | cyclo-propyl |
| 2,4-(OCH₃,OCH₃)-phenyl | COOH | H | cyclo-propyl |
| 4-OCF₃-phenyl | COOH | H | cyclo-propyl |
| 4-SCH₃-phenyl | COOH | H | cyclo-propyl |
| 3-SCF₃-phenyl | COOH | H | cyclo-propyl |
| 2,4-(NO₂,NO₂)-phenyl | COOH | H | cyclo-propyl |
| 4-NO₂-phenyl | COOH | H | cyclo-propyl |
| 2-thienyl | COOH | H | cyclo-propyl |
| 3-thienyl | COOH | H | cyclo-propyl |
| 2-furanyl | COOH | H | cyclo-propyl |
| 3-furanyl | COOH | H | cyclo-propyl |
| 2-tetrahydrofuranyl | COOH | H | cyclo-propyl |
| 3-tetrahydrofuranyl | COOH | H | cyclo-propyl |
| 2-pyridyl | COOH | H | cyclo-propyl |
| 3-pyridyl | COOH | H | cyclo-propyl |
| 4-pyridyl | COOH | H | cyclo-propyl |
| 2-tetrahydropyranyl | COOH | H | cyclo-propyl |
| 3-tetrahydropyranyl | COOH | H | cyclo-propyl |
| 4-tetrahydropyranyl | COOH | H | cyclo-propyl |
| iso-propoxy | COOH | H | cyclo-propyl |
| H | COOH | methyl | tert.-butyl |
| F | COOH | methyl | tert.-butyl |
| Cl | COOH | methyl | tert.-butyl |
| methyl | COOH | methyl | tert.-butyl |

TABLE B-continued

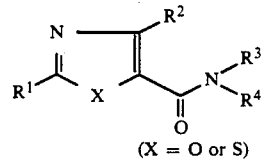

(X = O or S)

| R¹ | R² | R³ | R⁴ |
|---|---|---|---|
| ethyl | COOH | methyl | tert.-butyl |
| n-propyl | COOH | methyl | tert.-butyl |
| iso-propyl | COOH | methyl | tert.-butyl |
| n-butyl | COOH | methyl | tert.-butyl |
| iso-butyl | COOH | methyl | tert.-butyl |
| sec.-butyl | COOH | methyl | tert.-butyl |
| tert.-butyl | COOH | methyl | tert.-butyl |
| cyclo-propyl | COOH | methyl | tert.-butyl |
| cyclo-butyl | COOH | methyl | tert.-butyl |
| cyclo-pentyl | COOH | methyl | tert.-butyl |
| cyclo-hexyl | COOH | iso-propyl | tert.-butyl |
| cyclo-heptyl | COOH | iso-propyl | tert.-butyl |
| cyclo-octyl | COOH | iso-propyl | tert.-butyl |
| 1-methylcyclopropyl | COOH | iso-propyl | tert.-butyl |
| trifluoromethyl | COOH | iso-propyl | tert.-butyl |
| chlorodifluoromethyl | COOH | iso-propyl | tert.-butyl |
| pentafluoroethyl | COOH | iso-propyl | tert.-butyl |
| methoxymethyl | COOH | iso-propyl | tert.-butyl |
| 1-methylmethoxymethyl | COOH | iso-propyl | tert.-butyl |
| 1-methylmethoxyethyl | COOH | iso-propyl | tert.-butyl |
| ethoxymethyl | COOH | iso-propyl | tert.-butyl |
| vinyl | COOH | iso-propyl | tert.-butyl |
| allyl | COOH | iso-propyl | tert.-butyl |
| methallyl | COOH | iso-propyl | tert.-butyl |
| crotyl | COOH | iso-propyl | tert.-butyl |
| ethynyl | COOH | iso-propyl | tert.-butyl |
| propargyl | COOH | iso-propyl | tert.-butyl |
| phenylethynyl | COOH | iso-propyl | tert.-butyl |
| methoxy | COOH | iso-propyl | tert.-butyl |
| ethoxy | COOH | iso-propyl | tert.-butyl |
| trifluoromethoxy | COOH | iso-propyl | tert.-butyl |
| H | COOH | methyl | cyclo-propyl |
| F | COOH | methyl | cyclo-propyl |
| Cl | COOH | methyl | cyclo-propyl |
| methyl | COOH | methyl | cyclo-propyl |
| ethyl | COOH | methyl | cyclo-propyl |
| n-propyl | COOH | methyl | cyclo-propyl |
| iso-propyl | COOH | methyl | cyclo-propyl |
| n-butyl | COOH | iso-propyl | cyclo-propyl |
| iso-butyl | COOH | iso-propyl | cyclo-propyl |
| sec.-butyl | COOH | iso-propyl | cyclo-propyl |
| tert.-butyl | COOH | iso-propyl | tert.-butyl |
| cyclo-propyl | COOH | iso-propyl | cyclo-propyl |
| cyclo-butyl | COOH | iso-propyl | cyclo-propyl |
| cyclo-pentyl | COOH | iso-propyl | cyclo-propyl |
| cyclo-hexyl | COOH | methyl | cyclo-propyl |
| cyclo-heptyl | COOH | methyl | cyclo-propyl |
| cyclo-octyl | COOH | methyl | cyclo-propyl |
| 1-methylcyclopropyl | COOH | methyl | cyclo-propyl |
| trifluoromethyl | COOH | methyl | cyclo-propyl |
| chlorodifluoromethyl | COOH | methyl | cyclo-propyl |
| pentafluoroethyl | COOH | methyl | cyclo-propyl |
| methoxymethyl | COOH | iso-propyl | cyclo-propyl |
| 1-methylmethoxymethyl | COOH | iso-propyl | cyclo-propyl |
| 1-methylmethoxyethyl | COOH | iso-propyl | cyclo-propyl |
| ethoxymethyl | COOH | iso-propyl | cyclo-propyl |
| vinyl | COOH | iso-propyl | cyclo-propyl |
| allyl | COOH | iso-propyl | cyclo-propyl |
| methallyl | COOH | iso-propyl | cyclo-propyl |
| crotyl | COOH | methyl | cyclo-propyl |
| ethynyl | COOH | methyl | cyclo-propyl |
| propargyl | COOH | methyl | cyclo-propyl |
| phenylethynyl | COOH | methyl | cyclo-propyl |
| methoxy | COOH | methyl | cyclo-propyl |
| ethoxy | COOH | methyl | cyclo-propyl |
| trifluoromethoxy | COOH | methyl | cyclo-propyl |

TABLE A-1/B-1

| R¹ | R³ | R⁴ | R⁵ | X | Y |
|---|---|---|---|---|---|
| chloro | H | tert.-butyl | 4-hydroxy-2-butynyl | S | O |
| chloro | H | tert.-butyl | $N=C(C_2H_5)_2$ | S | O |
| chloro | H | tert.-butyl | $N=C(cyclo\text{-}C_3H_5)_2$ | S | O |
| chloro | H | tert.-butyl | 2-butanimino | S | O |
| chloro | H | tert.-butyl | cyclohexanimino | S | O |
| chloro | H | tert.-butyl | cyclooctanimino | S | O |
| methyl | H | tert.-butyl | $N=CH-C_6H_5$ | S | O |
| methyl | H | tert.-butyl | 2-Furyl-methanimino | S | O |
| methyl | H | tert.-butyl | $CH_2CH_2N(CH_3)_2$ | S | O |
| methyl | H | tert.-butyl | $CH_2CH_2N^+(CH_3)_3I^-$ | S | O |
| methyl | H | tert.-butyl | $CH_2CF_3$ | S | O |
| methyl | H | tert.-butyl | $CH_2CH_2Cl$ | S | O |
| methyl | H | tert.-butyl | $CH_2CH_2CN$ | S | O |
| iso-propyl | H | tert.-butyl | $CH_2CCl_3$ | S | O |
| iso-propyl | H | tert.-butyl | $CH_2CH_2Si(CH_3)_3$ | S | O |
| iso-propyl | H | tert.-butyl | $CH_2CH_2O-N=C(CH_3)_2$ | S | O |
| iso-propyl | H | tert.-butyl | $CH_2PO(OC_2H_5)_2$ | S | O |
| iso-propyl | H | tert.-butyl | $CH(CH_3)CH(OCH_3)_2$ | S | O |
| iso-propyl | H | tert.-butyl | $CH_2-CON(C_2H_5)_2$ | S | O |
| iso-propyl | H | tert.-butyl | benzyl | S | O |
| cyclo-propyl | H | tert.-butyl | 2,4-(Cl,Cl)-benzyl | S | O |
| cyclo-propyl | H | tert.-butyl | 3-pyridyl-methyl | S | O |
| cyclo-propyl | H | tert.-butyl | 2-thienyl-methyl | S | O |
| cyclo-propyl | H | tert.-butyl | 2-tetrahydrofuranyl-methyl | S | O |
| cyclo-propyl | H | tert.-butyl | 2-furanyl-methyl | S | O |
| cyclo-propyl | H | tert.-butyl | 2-pyridyl-methyl | S | O |
| cyclo-propyl | H | tert.-butyl | phenyl | S | O |
| allyl | H | tert.-butyl | 4-F-phenyl | S | O |
| allyl | H | tert.-butyl | 4-trifluoromethylphenyl | S | O |
| allyl | H | tert.-butyl | 2-$NO_2$-4-F-phenyl | S | O |
| allyl | H | tert.-butyl | 3,5-$(CF_3,CF_3)$-phenyl | S | O |
| allyl | H | tert.-butyl | 4-$OCH_3$-phenyl | S | O |
| allyl | H | tert.-butyl | 4-$OCF_3$-phenyl | S | O |
| allyl | H | tert.-butyl | 4-$NHCOCH_3$-phenyl | S | O |
| ethynyl | H | tert.-butyl | 2-tetrahydropyranyl | S | O |
| ethynyl | H | tert.-butyl | 2-tetrahydropyranyl | S | O |
| ethynyl | H | tert.-butyl | 1-benzotriazolyl | S | O |
| ethynyl | H | tert.-butyl | methyl | S | O |
| ethynyl | H | tert.-butyl | ethyl | S | O |
| ethynyl | H | tert.-butyl | n-propyl | S | O |
| ethynyl | H | tert.-butyl | iso-propyl | S | O |
| methyoxy | H | tert.-butyl | n-butyl | S | O |
| methyoxy | H | tert.-butyl | iso-butyl | S | O |
| methyoxy | H | tert.-butyl | sec.-butyl | S | O |
| methyoxy | H | tert.-butyl | tert.-butyl | S | O |
| methyoxy | H | tert.-butyl | cyclo-hexyl | S | O |
| methyoxy | H | tert.-butyl | cyclopropylmethyl | S | O |
| methyoxy | H | tert.-butyl | ethoxymethyl | S | O |
| 4-Cl-phenoxy | H | tert.-butyl | 2-methoxy-ethoxy-methyl | S | O |
| 4-Cl-phenoxy | H | tert.-butyl | benzyloxymethyl | S | O |
| 4-Cl-phenoxy | H | tert.-butyl | (4-bromobenzoyl)-methyl | S | O |
| 4-Cl-phenoxy | H | tert.-butyl | (4-methoxybenzoyl)-methyl | S | O |
| 4-Cl-phenoxy | H | tert.-butyl | phthalimidomethyl | S | O |
| 4-Cl-phenoxy | H | tert.-butyl | methylthiomethyl | S | O |
| 4-Cl-phenoxy | H | tert.-butyl | 2-thiomethyl-ethyl | S | O |
| phenylthio | H | tert.-butyl | $CH(C_6H_5)COOCH_3$ | S | O |
| phenylthio | H | tert.-butyl | phenylethyl | S | O |
| phenylthio | H | tert.-butyl | 4-F-phenylethyl | S | O |
| phenylthio | H | tert.-butyl | phthalimido | S | O |
| phenylthio | H | tert.-butyl | tetrahydrophthalimido | S | O |
| phenylthio | H | tert.-butyl | maleiimido | S | O |
| phenylthio | H | tert.-butyl | succinimido | S | O |
| 2,4-(Cl,Cl)-phenyl | H | tert.-butyl | piperidino | S | O |
| 2,4-(Cl,Cl)-phenyl | H | tert.-butyl | $Li^+$ | S | O |
| 2,4-(Cl,Cl)-phenyl | H | tert.-butyl | $Na^+$ | S | O |
| 2,4-(Cl,Cl)-phenyl | H | tert.-butyl | $K^+$ | S | O |
| 2,4-(Cl,Cl)-phenyl | H | tert.-butyl | $NH_4^+$ | S | O |
| 2,4-(Cl,Cl)-phenyl | H | tert.-butyl | diisopropylammonium | S | O |
| 2,4-(Cl,Cl)-phenyl | H | tert.-butyl | 2-hydroxyethyl-ammonium | S | O |
| 2-thienyl | H | tert.-butyl | allyl | S | O |
| 2-thienyl | H | tert.-butyl | methallyl | S | O |

TABLE A-1/B-1-continued $$\text{Ia} \quad \text{or} \quad \text{Ib}$$

| R¹ | R³ | R⁴ | R⁵ | X | Y |
|---|---|---|---|---|---|
| 2-thienyl | H | tert.-butyl | 2-chloroallyl | S | O |
| 2-thienyl | H | tert.-butyl | propargyl | S | O |
| 2-thienyl | H | tert.-butyl | 3-iodopropargyl | S | O |
| chloro | H | cyclo-propyl | 4-hydroxy-2-butynyl | S | O |
| chloro | H | cyclo-propyl | N=C(C₂H₅)₂ | S | O |
| chloro | H | cyclo-propyl | N=C(cyclo-C₃H₅)₂ | S | O |
| chloro | H | cyclo-propyl | 2-butanimino | S | O |
| chloro | H | cyclo-propyl | cyclohexanimino | S | O |
| chloro | H | cyclo-propyl | cyclooctanimino | S | O |
| methyl | H | cyclo-propyl | N=CH—C₆H₅ | S | O |
| methyl | H | cyclo-propyl | 2-furyl-methanimino | S | O |
| methyl | H | cyclo-propyl | CH₂CH₂N(CH₃)₂ | S | O |
| methyl | H | cyclo-propyl | CH₂CH₂N⁺(CH₃)₃I⁻ | S | O |
| methyl | H | cyclo-propyl | CH₂CF₃ | S | O |
| methyl | H | cyclo-propyl | CH₂CH₂Cl | S | O |
| methyl | H | cyclo-propyl | CH₂CH₂CN | S | O |
| iso-propyl | H | cyclo-propyl | CH₂CCl₃ | S | O |
| iso-propyl | H | cyclo-propyl | CH₂CH₂Si(CH₃)₃ | S | O |
| iso-propyl | H | cyclo-propyl | CH₂CH₂O—N=C(CH₃)₂ | S | O |
| iso-propyl | H | cyclo-propyl | CH₂PO(OC₂H₅)₂ | S | O |
| iso-propyl | H | cyclo-propyl | CH(CH₃)CH(OCH₃)₂ | S | O |
| iso-propyl | H | cyclo-propyl | CH₂—CON(C₂H₅)₂ | S | O |
| iso-propyl | H | cyclo-propyl | benzyl | S | O |
| cyclo-propyl | H | cyclo-propyl | 2,4-(Cl,Cl)-benzyl | S | O |
| cyclo-propyl | H | cyclo-propyl | 3-pyridyl-methyl | S | O |
| cyclo-propyl | H | cyclo-propyl | 2-thienyl-methyl | S | O |
| cyclo-propyl | H | cyclo-propyl | 2-tetrahydrofuranyl-methyl | S | O |
| cyclo-propyl | H | cyclo-propyl | 2-furanyl-methyl | S | O |
| cyclo-propyl | H | cyclo-propyl | 2-pyridyl-methyl | S | O |
| cyclo-propyl | H | cyclo-propyl | phenyl | S | O |
| allyl | H | cyclo-propyl | 4-F-phenyl | S | O |
| allyl | H | cyclo-propyl | 4-trifluoromethylphenyl | S | O |
| allyl | H | cyclo-propyl | 2-NO₂—F-phenyl | S | O |
| allyl | H | cyclo-propyl | 3,5-(CF₃,CF₃)-phenyl | S | O |
| allyl | H | cyclo-propyl | 4-OCH₃-phenyl | S | O |
| allyl | H | cyclo-propyl | 4-OCF₃-phenyl | S | O |
| allyl | H | cyclo-propyl | 4-NHCOCH₃-phenyl | S | O |
| ethynyl | H | cyclo-propyl | 2-tetrahydropyranyl | S | O |
| ethynyl | H | cyclo-propyl | 2-tetrahydrofuranyl | S | O |
| ethynyl | H | cyclo-propyl | 1-benzotriazolyl | S | O |
| ethynyl | H | cyclo-propyl | methyl | S | O |
| ethynyl | H | cyclo-propyl | ethyl | S | O |
| ethynyl | H | cyclo-propyl | n-propyl | S | O |
| ethynyl | H | cyclo-propyl | iso-propyl | S | O |
| methoxy | H | cyclo-propyl | n-butyl | S | O |
| methoxy | H | cyclo-propyl | iso-butyl | S | O |
| methoxy | H | cyclo-propyl | sec.-butyl | S | O |
| methoxy | H | cyclo-propyl | tert.-butyl | S | O |
| methoxy | H | cyclo-propyl | cyclo-hexyl | S | O |
| methoxy | H | cyclo-propyl | cyclopropylmethyl | S | O |
| methoxy | H | cyclo-propyl | ethoxymethyl | S | O |
| 4-Cl-phenoxy | H | cyclo-propyl | 2-methoxy-ethoxy-methyl | S | O |
| 4-Cl-phenoxy | H | cyclo-propyl | benzyloxymethyl | S | O |
| 4-Cl-phenoxy | H | cyclo-propyl | (4-bromobenzoyl)-methyl | S | O |
| 4-Cl-phenoxy | H | cyclo-propyl | (4-methoxybenzoyl)-methyl | S | O |
| 4-Cl-phenoxy | H | cyclo-propyl | phthalimidomethyl | S | O |
| 4-Cl-phenoxy | H | cyclo-propyl | methylthiomethyl | S | O |
| 4-Cl-phenoxy | H | cyclo-propyl | 2-thiomethyl-ethyl | S | O |
| phenylthio | H | cyclo-propyl | CH(C₆H₅)COOCH₃ | S | O |
| phenylthio | H | cyclo-propyl | phenylethyl | S | O |
| phenylthio | H | cyclo-propyl | 4-F-phenylethyl | S | O |
| phenylthio | H | cyclo-propyl | phthalimido | S | O |
| phenylthio | H | cyclo-propyl | tetrahydrophthalimido | S | O |
| phenylthio | H | cyclo-propyl | maleiimido | S | O |
| phenylthio | H | cyclo-propyl | succinimido | S | O |
| 2,4-(Cl,Cl)-phenyl | H | cyclo-propyl | piperidimo | S | O |
| 2,4-(Cl,Cl)-phenyl | H | cyclo-propyl | Li⁺ | S | O |
| 2,4-(Cl,Cl)-phenyl | H | cyclo-propyl | Na⁺ | S | O |
| 2,4-(Cl,Cl)-phenyl | H | cyclo-propyl | K⁺ | S | O |
| 2,4-(Cl,Cl)-phenyl | H | cyclo-propyl | NH₄⁺ | S | O |
| 2,4-(Cl,Cl)-phenyl | H | cyclo-propyl | diisopropylammonium | S | O |

TABLE A-1/B-1-continued

| R¹ | R³ | R⁴ | R⁵ | X | Y |
|---|---|---|---|---|---|
| 2,4-(Cl,Cl)-phenyl | H | cyclo-propyl | 2-hydroxy-ethyl-ammonium | S | O |
| 2-thienyl | H | cyclo-propyl | allyl | S | O |
| 2-thienyl | H | cyclo-propyl | methallyl | S | O |
| 2-thienyl | H | cyclo-propyl | 2-chloroallyl | S | O |
| 2-thienyl | H | cyclo-propyl | propargyl | S | O |
| 2-thienyl | H | cyclo-propyl | 3-iodopropargyl | S | O |
| H | H | tert.-butyl | $-N=C(CH_3)_2$ | S | O |
| F | H | tert.-butyl | $-N=C(CH_3)_2$ | S | O |
| Cl | H | tert.-butyl | $-N=C(CH_3)_2$ | S | O |
| methyl | H | tert.-butyl | $-N=C(CH_3)_2$ | S | O |
| ethyl | H | tert.-butyl | $-N=C(CH_3)_2$ | S | O |
| n-propyl | H | tert.-butyl | $-N=C(CH_3)_2$ | S | O |
| iso-propyl | H | tert.-butyl | $-N=C(CH_3)_2$ | S | O |
| n-butyl | H | tert.-butyl | $-N=C(CH_3)_2$ | S | O |
| iso-butyl | H | tert.-butyl | $-N=C(CH_3)_2$ | S | O |
| sec.-butyl | H | tert.-butyl | $-N=C(CH_3)_2$ | S | O |
| tert.-butyl | H | tert.-butyl | $-N=C(CH_3)_2$ | S | O |
| cyclo-propyl | H | tert.-butyl | $-N=C(CH_3)_2$ | S | O |
| cyclo-butyl | H | tert.-butyl | $-N=C(CH_3)_2$ | S | O |
| cyclo-pentyl | H | tert.-butyl | $-N=C(CH_3)_2$ | S | O |
| cyclo-hexyl | H | tert.-butyl | $-N=C(CH_3)_2$ | S | O |
| cyclo-heptyl | H | tert.-butyl | $-N=C(CH_3)_2$ | S | O |
| cyclo-octyl | H | tert.-butyl | $-N=C(CH_3)_2$ | S | O |
| 1-methylcyclopropyl | H | tert.-butyl | $-N=C(CH_3)_2$ | S | O |
| trifluoromethyl | H | tert.-butyl | $-N=C(CH_3)_2$ | S | O |
| chlorodifluoromethyl | H | tert.-butyl | $-N=C(CH_3)_2$ | S | O |
| pentafluoromethyl | H | tert.-butyl | $-N=C(CH_3)_2$ | S | O |
| iso-propoxy | H | tert.-butyl | $-N=C(CH_3)_2$ | S | O |
| methoxymethyl | H | tert.-butyl | $-N=C(CH_3)_2$ | S | O |
| 1-methylmethoxymethyl | H | tert.-butyl | $-N=C(CH_3)_2$ | S | O |
| 1-methylmethoxyethyl | H | tert.-butyl | $-N=C(CH_3)_2$ | S | O |
| ethoxymethyl | H | tert.-butyl | $-N=C(CH_3)_2$ | S | O |
| vinyl | H | tert.-butyl | $-N=C(CH_3)_2$ | S | O |
| allyl | H | tert.-butyl | $-N=C(CH_3)_2$ | S | O |
| methallyl | H | tert.-butyl | $-N=C(CH_3)_2$ | S | O |
| crotyl | H | tert.-butyl | $-N=C(CH_3)_2$ | S | O |
| ethynyl | H | tert.-butyl | $-N=C(CH_3)_2$ | S | O |
| propargyl | H | tert.-butyl | $-N=C(CH_3)_2$ | S | O |
| phenylethynyl | H | tert.-butyl | $-N=C(CH_3)_2$ | S | O |
| methoxy | H | tert.-butyl | $-N=C(CH_3)_2$ | S | O |
| ethoxy | H | tert.-butyl | $-N=C(CH_3)_2$ | S | O |
| trifluoromethoxy | H | tert.-butyl | $-N=C(CH_3)_2$ | S | O |
| methylthio | H | tert.-butyl | $-N=C(CH_3)_2$ | S | O |
| trifluoromethylthio | H | tert.-butyl | $-N=C(CH_3)_2$ | S | O |
| phenoxy | H | tert.-butyl | $-N=C(CH_3)_2$ | S | O |
| 4-Cl-phenoxy | H | tert.-butyl | $-N=C(CH_3)_2$ | S | O |
| 2,4-(Cl,Cl)-phenoxy | H | tert.-butyl | $-N=C(CH_3)_2$ | S | O |
| 4-CF₃-phenoxy | H | tert.-butyl | $-N=C(CH_3)_2$ | S | O |
| phenyl | H | tert.-butyl | $-N=C(CH_3)_2$ | S | O |
| 2-F-phenylthio | H | tert.-butyl | $-N=C(CH_3)_2$ | S | O |
| 3-F-phenyl | H | tert.-butyl | $-N=C(CH_3)_2$ | S | O |
| 2,4-(F,F)-phenyl | H | tert.-butyl | $-N=C(CH_3)_2$ | S | O |
| 2-Cl-phenyl | H | tert.-butyl | $-N=C(CH_3)_2$ | S | O |
| 3-Cl-phenyl | H | tert.-butyl | $-N=C(CH_3)_2$ | S | O |
| 2,4-(Cl,Cl)-phenyl | H | tert.-butyl | $-N=C(CH_3)_2$ | S | O |
| 2-CH₃-phenyl | H | tert.-butyl | $-N=C(CH_3)_2$ | S | O |
| 3-CH₃-phenyl | H | tert.-butyl | $-N=C(CH_3)_2$ | S | O |
| 4-CH₃-phenyl | H | tert.-butyl | $-N=C(CH_3)_2$ | S | O |
| 2,4-(CH₃,CH₃)-phenyl | H | tert.-butyl | $-N=C(CH_3)_2$ | S | O |
| 2,4,6-(CH₃,CH₃,CH₃)-phenyl | H | tert.-butyl | $-N=C(CH_3)_2$ | S | O |
| 2-CF₃-phenyl | H | tert.-butyl | $-N=C(CH_3)_2$ | S | O |
| 2-OCH₃-phenyl | H | tert.-butyl | $-N=C(CH_3)_2$ | S | O |
| 2,4-(OCH₃,OCH₃)-phenyl | H | tert.-butyl | $-N=C(CH_3)_2$ | S | O |
| 4-OCF₃-phenyl | H | tert.-butyl | $-N=C(CH_3)_2$ | S | O |
| 4-SCH₃-phenyl | H | tert.-butyl | $-N=C(CH_3)_2$ | S | O |
| 3-SCF₃-phenyl | H | tert.-butyl | $-N=C(CH_3)_2$ | S | O |
| 2,4-(NO₂,NO₂)-phenyl | H | tert.-butyl | $-N=C(CH_3)_2$ | S | O |
| 4-NO₂-phenyl | H | tert.-butyl | $-N=C(CH_3)_2$ | S | O |
| 2-thienyl | H | tert.-butyl | $-N=C(CH_3)_2$ | S | O |
| 3-thienyl | H | tert.-butyl | $-N=C(CH_3)_2$ | S | O |
| 2-furanyl | H | tert.-butyl | $-N=C(CH_3)_2$ | S | O |

TABLE A-1/B-1-continued

|   |   | Ia | | or | | Ib | |   |   |
|---|---|---|---|---|---|---|---|---|---|

| R¹ | R³ | R⁴ | R⁵ | X | Y |
|---|---|---|---|---|---|
| 3-furanyl | H | tert.-butyl | —N=C(CH₃)₂ | S | O |
| 2-tetrahydrofuranyl | H | tert.-butyl | —N=C(CH₃)₂ | S | O |
| 3-tetrahydrofuranyl | H | tert.-butyl | —N=C(CH₃)₂ | S | O |
| 2-pyridyl | H | tert.-butyl | —N=C(CH₃)₂ | S | O |
| 3-pyridyl | H | tert.-butyl | —N=C(CH₃)₂ | S | O |
| 4-pyridyl | H | tert.-butyl | —N=C(CH₃)₂ | S | O |
| 2-tetrahydropyranyl | H | tert.-butyl | —N=C(CH₃)₂ | S | O |
| 3-tetrahydropyranyl | H | tert.-butyl | —N=C(CH₃)₂ | S | O |
| 4-tetrahydropyranyl | H | tert.-butyl | —N=C(CH₃)₂ | S | O |
| H | H | cyclo-propyl | —N=C(CH₃)₂ | S | O |
| F | H | cyclo-propyl | —N=C(CH₃)₂ | S | O |
| Cl | H | cyclo-propyl | —N=C(CH₃)₂ | S | O |
| methyl | H | cyclo-propyl | —N=C(CH₃)₂ | S | O |
| ethyl | H | cyclo-propyl | —N=C(CH₃)₂ | S | O |
| n-propyl | H | cyclo-propyl | —N=C(CH₃)₂ | S | O |
| iso-propyl | H | cyclo-propyl | —N=C(CH₃)₂ | S | O |
| n-butyl | H | cyclo-propyl | —N=C(CH₃)₂ | S | O |
| iso-butyl | H | cyclo-propyl | —N=C(CH₃)₂ | S | O |
| sec.-butyl | H | cyclo-propyl | —N=C(CH₃)₂ | S | O |
| tert.-butyl | H | cyclo-propyl | —N=C(CH₃)₂ | S | O |
| cyclo-propyl | H | cyclo-propyl | —N=C(CH₃)₂ | S | O |
| cyclo-butyl | H | cyclo-propyl | —N=C(CH₃)₂ | S | O |
| cyclo-pentyl | H | cyclo-propyl | —N=C(CH₃)₂ | S | O |
| cyclo-hexyl | H | cyclo-propyl | —N=C(CH₃)₂ | S | O |
| cyclo-heptyl | H | cyclo-propyl | —N=C(CH₃)₂ | S | O |
| cyclo-octyl | H | cyclo-propyl | —N=C(CH₃)₂ | S | O |
| 1-methylcyclopropyl | H | cyclo-propyl | —N=C(CH₃)₂ | S | O |
| trifluoromethyl | H | cyclo-propyl | —N=C(CH₃)₂ | S | O |
| chlorodifluoromethyl | H | cyclo-propyl | —N=C(CH₃)₂ | S | O |
| pentafluoromethyl | H | cyclo-propyl | —N=C(CH₃)₂ | S | O |
| iso-propoxy | H | cyclo-propyl | —N=C(CH₃)₂ | S | O |
| methoxymethyl | H | cyclo-propyl | —N=C(CH₃)₂ | S | O |
| 1-methylmethoxymethyl | H | cyclo-propyl | —N=C(CH₃)₂ | S | O |
| 1-methylmethoxyethyl | H | cyclo-propyl | —N=C(CH₃)₂ | S | O |
| ethoxymethyl | H | cyclo-propyl | —N=C(CH₃)₂ | S | O |
| vinyl | H | cyclo-propyl | —N=C(CH₃)₂ | S | O |
| allyl | H | cyclo-propyl | —N=C(CH₃)₂ | S | O |
| methallyl | H | cyclo-propyl | —N=C(CH₃)₂ | S | O |
| crotyl | H | cyclo-propyl | —N=C(CH₃)₂ | S | O |
| ethynyl | H | cyclo-propyl | —N=C(CH₃)₂ | S | O |
| propargyl | H | cyclo-propyl | —N=C(CH₃)₂ | S | O |
| phenylethynyl | H | cyclo-propyl | —N=C(CH₃)₂ | S | O |
| methoxy | H | cyclo-propyl | —N=C(CH₃)₂ | S | O |
| ethoxy | H | cyclo-propyl | —N=C(CH₃)₂ | S | O |
| trifluoromethoxy | H | cyclo-propyl | —N=C(CH₃)₂ | S | O |
| methylthio | H | cyclo-propyl | —N=C(CH₃)₂ | S | O |
| trifluoromethylthio | H | cyclo-propyl | —N=C(CH₃)₂ | S | O |
| phenoxy | H | cyclo-propyl | —N=C(CH₃)₂ | S | O |
| 4-Cl-phenoxy | H | cyclo-propyl | —N=C(CH₃)₂ | S | O |
| 2,4-(Cl,Cl)-phenoxy | H | cyclo-propyl | —N=C(CH₃)₂ | S | O |
| 4-CF₃-phenoxy | H | cyclo-propyl | —N=C(CH₃)₂ | S | O |
| phenyl | H | cyclo-propyl | —N=C(CH₃)₂ | S | O |
| 2-F-phenylthio | H | cyclo-propyl | —N=C(CH₃)₂ | S | O |
| 3-F-phenyl | H | cyclo-propyl | —N=C(CH₃)₂ | S | O |
| 2,4-(F,F)-phenyl | H | cyclo-propyl | —N=C(CH₃)₂ | S | O |
| 2-Cl-phenyl | H | cyclo-propyl | —N=C(CH₃)₂ | S | O |
| 3-Cl-phenyl | H | cyclo-propyl | —N=C(CH₃)₂ | S | O |
| 2,4-(Cl,Cl)-phenyl | H | cyclo-propyl | —N=C(CH₃)₂ | S | O |
| 2-CH₃-phenyl | H | cyclo-propyl | —N=C(CH₃)₂ | S | O |
| 3-CH₃-phenyl | H | cyclo-propyl | —N=C(CH₃)₂ | S | O |
| 4-CH₃-phenyl | H | cyclo-propyl | —N=C(CH₃)₂ | S | O |
| 2,4-(CH₃,CH₃)-phenyl | H | cyclo-propyl | —N=C(CH₃)₂ | S | O |
| 2,4,6-(CH₃,CH₃,CH₃)-phenyl | H | cyclo-propyl | —N=C(CH₃)₂ | S | O |
| 2-CF₃-phenyl | H | cyclo-propyl | —N=C(CH₃)₂ | S | O |
| 2-OCH₃-phenyl | H | cyclo-propyl | —N=C(CH₃)₂ | S | O |
| 2,4-(OCH₃,OCH₃)-phenyl | H | cyclo-propyl | —N=C(CH₃)₂ | S | O |
| 4-OCF₃-phenyl | H | cyclo-propyl | —N=C(CH₃)₂ | S | O |
| 4-SCH₃-phenyl | H | cyclo-propyl | —N=C(CH₃)₂ | S | O |
| 3-SCF₃-phenyl | H | cyclo-propyl | —N=C(CH₃)₂ | S | O |
| 2,4-(NO₂,NO₂)-phenyl | H | cyclo-propyl | —N=C(CH₃)₂ | S | O |
| 4-NO₂-phenyl | H | cyclo-propyl | —N=C(CH₃)₂ | S | O |

TABLE A-1/B-1-continued

| R¹ | R³ | R⁴ | R⁵ | X | Y |
|---|---|---|---|---|---|
| 2-thienyl | H | cyclo-propyl | —N=C(CH₃)₂ | S | O |
| 3-thienyl | H | cyclo-propyl | —N=C(CH₃)₂ | S | O |
| 2-furanyl | H | cyclo-propyl | —N=C(CH₃)₂ | S | O |
| 3-furanyl | H | cyclo-propyl | —N=C(CH₃)₂ | S | O |
| 2-tetrahydrofuranyl | H | cyclo-propyl | —N=C(CH₃)₂ | S | O |
| 3-tetrahydrofuranyl | H | cyclo-propyl | —N=C(CH₃)₂ | S | O |
| 2-pyridyl | H | cyclo-propyl | —N=C(CH₃)₂ | S | O |
| 3-pyridyl | H | cyclo-propyl | —N=C(CH₃)₂ | S | O |
| 4-pyridyl | H | cyclo-propyl | —N=C(CH₃)₂ | S | O |
| 2-tetrahydropyranyl | H | cyclo-propyl | —N=C(CH₃)₂ | S | O |
| 3-tetrahydropyranyl | H | cyclo-propyl | —N=C(CH₃)₂ | S | O |
| 4-tetrahydropyranyl | H | cyclo-propyl | —N=C(CH₃)₂ | S | O |
| chloro | H | methyl | H | S | O |
| chloro | H | ethyl | H | S | O |
| chloro | H | n-propyl | H | S | O |
| chloro | H | iso-propyl | H | S | O |
| chloro | H | n-butyl | H | S | O |
| chloro | H | iso-butyl | H | S | O |
| methyl | H | sec.-butyl | H | S | O |
| methyl | H | n-pentyl | H | S | O |
| methyl | H | 2-pentyl | H | S | O |
| methyl | H | 3-pentyl | H | S | O |
| methyl | H | n-hexyl | H | S | O |
| methyl | H | 2-hexyl | H | S | O |
| iso-propyl | H | 3-hexyl | H | S | O |
| iso-propyl | H | 2-methyl-2-pentyl | H | S | O |
| iso-propyl | H | cyclo-propylmethyl | H | S | O |
| iso-propyl | H | cyclo-butyl | H | S | O |
| iso-propyl | H | cyclo-pentyl | H | S | O |
| iso-propyl | H | cyclo-hexyl | H | S | O |
| cyclo-propyl | H | 1-methylcyclohexyl | H | S | O |
| cyclo-propyl | H | 3-trifluoromethylcyclohexyl | H | S | O |
| cyclo-propyl | H | allyl | H | S | O |
| cyclo-propyl | H | 1-buten-3-yl | H | S | O |
| cyclo-propyl | H | crotyl | H | S | O |
| cyclo-propyl | H | propargyl | H | S | O |
| allyl | H | 1-butyn-3-yl | H | S | O |
| allyl | H | 3-methyl-1-butyn-3-yl | H | S | O |
| allyl | H | 2-pentyn-4-yl | H | S | O |
| allyl | H | benzyl | H | S | O |
| allyl | H | 2-phenylethyl | H | S | O |
| allyl | H | 2-methylthioethyl | H | S | O |
| ethynyl | H | 2-chloroethyl | H | S | O |
| ethynyl | H | 2-methoxyethyl | H | S | O |
| ethynyl | H | 2-(N,N-dimethylamino)ethyl | H | S | O |
| ethynyl | H | phenyl | H | S | O |
| ethynyl | H | 2-CH₃-phenyl | H | S | O |
| ethynyl | H | 4-CH₃-phenyl | H | S | O |
| methoxy | H | 2,4-(CH₃,CH₃)-phenyl | H | S | O |
| methoxy | H | 2,3,5-(CH₃,CH₃,CH₃)-phenyl | H | S | O |
| methoxy | H | 3-CF₃-phenyl | H | S | O |
| methoxy | H | 3-F-phenyl | H | S | O |
| methoxy | H | 2-Cl-phenyl | H | S | O |
| methoxy | H | 4-Cl-phenyl | H | S | O |
| 4-Cl-phenoxy | H | 2,4-(F,F)-phenyl | H | S | O |
| 4-Cl-phenoxy | H | 2,3,5-(Cl,Cl,Cl)-phenyl | H | S | O |
| 4-Cl-phenoxy | H | 2-CN-phenyl | H | S | O |
| 4-Cl-phenoxy | H | 2-OCH₃-phenyl | H | S | O |
| 4-Cl-phenoxy | H | 2,3-(OCH₃,OCH₃)-phenyl | H | S | O |
| 4-Cl-phenoxy | H | 3,4,5-(OCH₃,OCH₃,OCH₃)-phenyl | H | S | O |
| phentylthio | H | 3-OCF₃-phenyl | H | S | O |
| phentylthio | H | 4-OCF₂CHF₂-phenyl | H | S | O |
| phentylthio | H | 2-SCH₃-phenyl | H | S | O |
| phentylthio | H | 2,4-(SCH₃,SCH₃)-phenyl | H | S | O |
| phentylthio | H | 2-SCF₃-phenyl | H | S | O |
| phentylthio | H | 4-NO₂-phenyl | H | S | O |
| 2,4-(Cl,Cl)-phenyl | H | 2,4-(NO₂,NO₂)-phenyl | H | S | O |
| 2,4-(Cl,Cl)-phenyl | H | 2-CHO-phenyl | H | S | O |
| 2,4-(Cl,Cl)-phenyl | H | 3-COCH₃-phenyl | H | S | O |
| 2,4-(Cl,Cl)-phenyl | H | 3-COCF₃-phenyl | H | S | O |
| 2,4-(Cl,Cl)-phenyl | H | 1-naphthyl | H | S | O |

TABLE A-1/B-1-continued

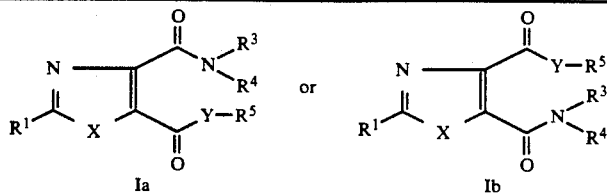

| $R^1$ | $R^3$ | $R^4$ | $R^5$ | X | Y |
|---|---|---|---|---|---|
| 2,4-(Cl,Cl)-phenyl | H | 2-naphthyl | H | S | O |
| 2-thienyl | H | piperidino | H | S | O |
| 2-thienyl | H | 3-tetrahydrofuranyl | H | S | O |
| 2-thienyl | H | 4-tetrahydropyranyl | H | S | O |
| 2-thienyl | H | 2-thiazolyl | H | S | O |
| 2-thienyl | H | 5-$CH_3$-2-thiazolyl | H | S | O |
| 2-thienyl | H | 4-$CH_3$-5-COOH-2-thiazolyl | H | S | O |
| 3-pyridyl | H | methyl | H | S | O |
| 3-pyridyl | H | ethyl | H | S | O |
| 3-pyridyl | H | n-propyl | H | S | O |
| 3-pyridyl | H | iso-propyl | H | S | O |
| 3-pyridyl | H | n-butyl | H | S | O |
| 3-pyridyl | H | iso-butyl | H | S | O |
| iso-propyl | methyl | sec.-butyl | H | S | O |
| iso-propyl | methyl | n-pentyl | H | S | O |
| iso-propyl | methyl | 2-pentyl | H | S | O |
| iso-propyl | methyl | 3-pentyl | H | S | O |
| iso-propyl | methyl | n-hexyl | H | S | O |
| iso-propyl | methyl | 2-hexyl | H | S | O |
| iso-propyl | methyl | 3-hexyl | H | S | O |
| chloro | H | methyl | $-N=C(CH_3)_2$ | S | O |
| chloro | H | ethyl | $-N=C(CH_3)_2$ | S | O |
| chloro | H | n-propyl | $-N=C(CH_3)_2$ | S | O |
| chloro | H | iso-propyl | $-N=C(CH_3)_2$ | S | O |
| chloro | H | n-butyl | $-N=C(CH_3)_2$ | S | O |
| chloro | H | iso-butyl | $-N=C(CH_3)_2$ | S | O |
| methyl | H | sec.-butyl | $-N=C(CH_3)_2$ | S | O |
| methyl | H | n-pentyl | $-N=C(CH_3)_2$ | S | O |
| methyl | H | 2-pentyl | $-N=C(CH_3)_2$ | S | O |
| methyl | H | 3-pentyl | $-N=C(CH_3)_2$ | S | O |
| methyl | H | n-hexyl | $-N=C(CH_3)_2$ | S | O |
| methyl | H | 2-hexyl | $-N=C(CH_3)_2$ | S | O |
| iso-propyl | H | 3-hexyl | $-N=C(CH_3)_2$ | S | O |
| iso-propyl | H | 2-methyl-2-pentyl | $-N=C(CH_3)_2$ | S | O |
| iso-propyl | H | cyclo-propylmethyl | $-N=C(CH_3)_2$ | S | O |
| iso-propyl | H | cyclo-butyl | $-N=C(CH_3)_2$ | S | O |
| iso-propyl | H | cyclo-pentyl | $-N=C(CH_3)_2$ | S | O |
| iso-propyl | H | cyclo-hexyl | $-N=C(CH_3)_2$ | S | O |
| cyclo-propyl | H | 1-methylcyclohexyl | $-N=C(CH_3)_2$ | S | O |
| cyclo-propyl | H | 3-trifluoromethylcyclohexyl | $-N=C(CH_3)_2$ | S | O |
| cyclo-propyl | H | allyl | $-N=C(CH_3)_2$ | S | O |
| cyclo-propyl | H | 1-buten-3-yl | $-N=C(CH_3)_2$ | S | O |
| cyclo-propyl | H | crotyl | $-N=C(CH_3)_2$ | S | O |
| cyclo-propyl | H | propargyl | $-N=C(CH_3)_2$ | S | O |
| allyl | H | 1-butyn-3-yl | $-N=C(CH_3)_2$ | S | O |
| allyl | H | 3-methyl-1-butyn-3-yl | $-N=C(CH_3)_2$ | S | O |
| allyl | H | 2-pentyn-4-yl | $-N=C(CH_3)_2$ | S | O |
| allyl | H | benzyl | $-N=C(CH_3)_2$ | S | O |
| allyl | H | 2-phenylethyl | $-N=C(CH_3)_2$ | S | O |
| allyl | H | 2-methylthioethyl | $-N=C(CH_3)_2$ | S | O |
| ethynyl | H | 2-chloroethyl | $-N=C(CH_3)_2$ | S | O |
| ethynyl | H | 2-methoxyethyl | $-N=C(CH_3)_2$ | S | O |
| ethynyl | H | 2-(n,N-dimethylamino)ethyl | $-N=C(CH_3)_2$ | S | O |
| ethynyl | H | phenyl | $-N=C(CH_3)_2$ | S | O |
| ethynyl | H | 2-$CH_3$-phenyl | $-N=C(CH_3)_2$ | S | O |
| ethynyl | H | 4-$CH_3$-phenyl | $-N=C(CH_3)_2$ | S | O |
| methoxy | H | 2,4-($CH_3$,$CH_3$)-phenyl | $-N=C(CH_3)_2$ | S | O |
| methoxy | H | 2,3,5-($CH_3$,$CH_3$,$CH_3$)-phenyl | $-N=C(CH_3)_2$ | S | O |
| methoxy | H | 3-$CF_3$-phenyl | $-N=C(CH_3)_2$ | S | O |
| methoxy | H | 3-F-phenyl | $-N=C(CH_3)_2$ | S | O |
| methoxy | H | 2-Cl-phenyl | $-N=C(CH_3)_2$ | S | O |
| methoxy | H | 4-Cl-phenyl | $-N=C(CH_3)_2$ | S | O |
| 4-Cl-phenoxy | H | 2,4-(F,F)-phenyl | $-N=C(CH_3)_2$ | S | O |
| 4-Cl-phenoxy | H | 2,3,5-(Cl,Cl,Cl)-phenyl | $-N=C(CH_3)_2$ | S | O |
| 4-Cl-phenoxy | H | 2-CN-phenyl | $-N=C(CH_3)_2$ | S | O |
| 4-Cl-phenoxy | H | 2-$OCH_3$-phenyl | $-N=C(CH_3)_2$ | S | O |
| 4-Cl-phenoxy | H | 2,3-($OCH_3$,$OCH_3$)-phenyl | $-N=C(CH_3)_2$ | S | O |
| 4-Cl-phenoxy | H | 3,4,5-($OCH_3$,$OCH_3$,$OCH_3$)-phenyl | $-N=C(CH_3)_2$ | S | O |
| phenylthio | H | 3-$OCF_3$-phenyl | $-N=C(CH_3)_2$ | S | O |
| phenylthio | H | 4-$OCF_2CHF_2$-phenyl | $-N=C(CH_3)_2$ | S | O |
| phenylthio | H | 2-$SCH_3$-phenyl | $-N=C(CH_3)_2$ | S | O |

TABLE A-1/B-1-continued

| R¹ | R³ | R⁴ | R⁵ | X | Y |
|---|---|---|---|---|---|
| phenylthio | H | 2,4-(SCH₃,SCH₃)-phenyl | $-N=C(CH_3)_2$ | S | O |
| phenylthio | H | 2-SCF₃-phenyl | $-N=C(CH_3)_2$ | S | O |
| phenylthio | H | 4-NO₂-phenyl | $-N=C(CH_3)_2$ | S | O |
| 2,4-(Cl,Cl)-phenyl | H | 2,4-(NO₂,NO₂)-phenyl | $-N=C(CH_3)_2$ | S | O |
| 2,4-(Cl,Cl)-phenyl | H | 2-CHO-phenyl | $-N=C(CH_3)_2$ | S | O |
| 2,4-(Cl,Cl)-phenyl | H | 3-COCH₃-phenyl | $-N=C(CH_3)_2$ | S | O |
| 2,4-(Cl,Cl)-phenyl | H | 3-COCF₃-phenyl | $-N=C(CH_3)_2$ | S | O |
| 2,4-(Cl,Cl)-phenyl | H | 1-naphthyl | $-N=C(CH_3)_2$ | S | O |
| 2,4-(Cl,Cl)-phenyl | H | 2-naphthyl | $-N=C(CH_3)_2$ | S | O |
| 2-thienyl | H | piperidino | $-N=C(CH_3)_2$ | S | O |
| 2-thienyl | H | 3-tetrahydrofuranyl | $-N=C(CH_3)_2$ | S | O |
| 2-thienyl | H | 4-tetrahydropyranyl | $-N=C(CH_3)_2$ | S | O |
| 2-thienyl | H | 2-thiazolyl | $-N=C(CH_3)_2$ | S | O |
| 2-thienyl | H | 5-CH₃-2-thiazolyl | $-N=C(CH_3)_2$ | S | O |
| 2-thienyl | H | 4-CH₃-5-COOH-2-thiazolyl | $-N=C(CH_3)_2$ | S | O |
| 3-pyridyl | H | methyl | $-N=C(CH_3)_2$ | S | O |
| 3-pyridyl | H | ethyl | $-N=C(CH_3)_2$ | S | O |
| 3-pyridyl | H | n-propyl | $-N=C(CH_3)_2$ | S | O |
| 3-pyridyl | H | iso-propyl | $-N=C(CH_3)_2$ | S | O |
| 3-pyridyl | H | n-butyl | $-N=C(CH_3)_2$ | S | O |
| 3-pyridyl | H | iso-butyl | $-N=C(CH_3)_2$ | S | O |
| iso-propyl | methyl | sec.-butyl | $-N=C(CH_3)_2$ | S | O |
| iso-propyl | methyl | n-pentyl | $-N=C(CH_3)_2$ | S | O |
| iso-propyl | methyl | 2-pentyl | $-N=C(CH_3)_2$ | S | O |
| iso-propyl | methyl | 3-pentyl | $-N=C(CH_3)_2$ | S | O |
| iso-propyl | methyl | n-hexyl | $-N=C(CH_3)_2$ | S | O |
| iso-propyl | methyl | 2-hexyl | $-N=C(CH_3)_2$ | S | O |
| iso-propyl | methyl | 3-hexyl | $-N=C(CH_3)_2$ | S | O |
| methyl | H | tert.-butyl | 2,4-(Cl,Cl)-phenyl | S | S |
| methyl | H | tert.-butyl | 2-pyridyl | S | S |
| methyl | H | tert.-butyl | ethyl | S | S |
| methyl | H | tert.-butyl | iso-propyl | S | S |
| methyl | H | tert.-butyl | butyl | S | S |
| methyl | H | tert.-butyl | tert.-butyl | S | S |
| methyl | H | tert.-butyl | phenyl | S | S |
| iso-phenyl | H | tert.-butyl | 4-F-phenyl | S | S |
| iso-phenyl | H | tert.-butyl | 3-CF₃-phenyl | S | S |
| iso-propyl | H | tert.-butyl | 2,4-(Cl,Cl)-phenyl | S | S |
| iso-propyl | H | tert.-butyl | 2-pyridyl | S | S |
| iso-propyl | H | tert.-butyl | methyl | S | S |
| iso-propyl | H | tert.-butyl | ethyl | S | S |
| iso-propyl | H | tert.-butyl | iso-propyl | S | S |
| cyclo-propyl | H | tert.-butyl | butyl | S | S |
| cyclo-propyl | H | tert.-butyl | tert.-butyl | S | S |
| cyclo-propyl | H | tert.-butyl | phenyl | S | S |
| cyclo-propyl | H | tert.-butyl | 4-F-phenyl | S | S |
| cyclo-propyl | H | tert.-butyl | 3-CF₃-phenyl | S | S |
| cyclo-propyl | H | tert.-butyl | 2,4-(Cl,Cl)-phenyl | S | S |
| cyclo-propyl | H | tert.-butyl | 2-pyridyl | S | S |
| allyl | H | tert.-butyl | methyl | S | S |
| allyl | H | tert.-butyl | ethyl | S | S |
| allyl | H | tert.-butyl | iso-propyl | S | S |
| allyl | H | tert.-butyl | butyl | S | S |
| allyl | H | tert.-butyl | tert.-butyl | S | S |
| allyl | H | tert.-butyl | phenyl | S | S |
| methoxy | H | tert.-butyl | methyl | S | S |
| methoxy | H | tert.-butyl | ethyl | S | S |
| methoxy | H | tert.-butyl | iso-propyl | S | S |
| methoxy | H | tert.-butyl | butyl | S | S |
| methoxy | H | tert.-butyl | tert.-butyl | S | S |
| methoxy | H | tert.-butyl | phenyl | S | S |
| methoxy | H | tert.-butyl | 4-F-phenyl | S | S |
| 4-Cl-phenoxy | H | tert.-butyl | 3-CF₃-phenyl | S | S |
| 4-Cl-phenoxy | H | tert.-butyl | 2,4-(Cl,Cl)-phenyl | S | S |
| 4-Cl-phenoxy | H | tert.-butyl | 2-pyridyl | S | S |
| 4-Cl-phenoxy | H | tert.-butyl | methyl | S | S |
| 4-Cl-phenoxy | H | tert.-butyl | ethyl | S | S |
| 4-Cl-phenoxy | H | tert.-butyl | isopropyl | S | S |
| 4-Cl-phenoxy | H | tert.-butyl | butyl | S | S |
| 2,4-(Cl,Cl)-phenyl | H | tert.-butyl | tert.-butyl | S | S |
| 2,4-(Cl,Cl)-phenyl | H | tert.-butyl | phenyl | S | S |

TABLE A-1/B-1-continued

| R¹ | R³ | R⁴ | R⁵ | X | Y |
|---|---|---|---|---|---|
| 2,4-(Cl,Cl)-phenyl | H | tert.-butyl | 4-F-phenyl | S | S |
| 2,4-(Cl,Cl)-phenyl | H | tert.-butyl | 3-CF₃-phenyl | S | S |
| 2,4-(Cl,Cl)-phenyl | H | tert.-butyl | 2,4-(Cl,Cl)-phenyl | S | S |
| 2,4-(Cl,Cl)-phenyl | H | tert.-butyl | 2-pyridyl | S | S |
| 2,4-(Cl,Cl)-phenyl | H | tert.-butyl | ethyl | S | S |
| 2-thienyl | H | tert.-butyl | iso-propyl | S | S |
| 2-thienyl | H | tert.-butyl | butyl | S | S |
| 2-thienyl | H | tert.-butyl | tert.-butyl | S | S |
| 3-pyridyl | H | tert.-butyl | phenyl | S | S |
| 3-pyridyl | H | tert.-butyl | 4-F-phenyl | S | S |
| 3-pyridyl | H | tert.-butyl | 3-CF₃-phenyl | S | S |
| methyl | H | cyclo-propyl | 2,4-(Cl,Cl)-phenyl | S | S |
| methyl | H | cyclo-propyl | 2-pyridyl | S | S |
| methyl | H | cyclo-propyl | ethyl | S | S |
| methyl | H | cyclo-propyl | iso-propyl | S | S |
| methyl | H | cyclo-propyl | butyl | S | S |
| methyl | H | cyclo-propyl | tert.-butyl | S | S |
| methyl | H | cyclo-propyl | phenyl | S | S |
| iso-propyl | H | cyclo-propyl | 4-F-phenyl | S | S |
| iso-propyl | H | cyclo-propyl | 3-CF₃-phenyl | S | S |
| iso-propyl | H | cyclo-propyl | 2,4-(Cl,Cl)-phenyl | S | S |
| iso-propyl | H | cyclo-propyl | 2-pyridyl | S | S |
| iso-propyl | H | cyclo-propyl | methyl | S | S |
| iso-propyl | H | cyclo-propyl | ethyl | S | S |
| iso-propyl | H | cyclo-propyl | iso-propyl | S | S |
| cyclo-propyl | H | cyclo-propyl | butyl | S | S |
| cyclo-propyl | H | cyclo-propyl | tert.-butyl | S | S |
| cyclo-propyl | H | cyclo-propyl | phenyl | S | S |
| cyclo-propyl | H | cyclo-propyl | 4-F-phenyl | S | S |
| cyclo-propyl | H | cyclo-propyl | 3-CF₃-phenyl | S | S |
| cyclo-propyl | H | cyclo-propyl | 2,4-(Cl,Cl)-phenyl | S | S |
| cyclo-propyl | H | cyclo-propyl | 2-pyridyl | S | S |
| allyl | H | cyclo-propyl | methyl | S | S |
| allyl | H | cyclo-propyl | ethyl | S | S |
| allyl | H | cyclo-propyl | iso-propyl | S | S |
| allyl | H | cyclo-propyl | butyl | S | S |
| allyl | H | cyclo-propyl | tert.-butyl | S | S |
| allyl | H | cyclo-propyl | phenyl | S | S |
| methoxy | H | cyclo-propyl | methyl | S | S |
| methoxy | H | cyclo-propyl | ethyl | S | S |
| methoxy | H | cyclo-propyl | iso-propyl | S | S |
| methoxy | H | cyclo-propyl | butyl | S | S |
| methoxy | H | cyclo-propyl | tert.-butyl | S | S |
| methoxy | H | cyclo-propyl | phenyl | S | S |
| methoxy | H | cyclo-propyl | 4-F-phenyl | S | S |
| 4-Cl-phenoxy | H | cyclo-propyl | 3-CF₃-phenyl | S | S |
| 4-Cl-phenoxy | H | cyclo-propyl | 2,4-(Cl,Cl)-phenyl | S | S |
| 4-Cl-phenoxy | H | cyclo-propyl | 2-pyridyl | S | S |
| 4-Cl-phenoxy | H | cyclo-propyl | methyl | S | S |
| 4-Cl-phenoxy | H | cyclo-propyl | ethyl | S | S |
| 4-Cl-phenoxy | H | cyclo-propyl | iso-propyl | S | S |
| 4-Cl-phenoxy | H | cyclo-propyl | butyl | S | S |
| 2,4-(Cl,Cl)-phenyl | H | cyclo-propyl | tert.-butyl | S | S |
| 2,4-(Cl,Cl)-phenyl | H | cyclo-propyl | phenyl | S | S |
| 2,4-(Cl,Cl)-phenyl | H | cyclo-propyl | 4-F-phenyl | S | S |
| 2,4-(Cl,Cl)-phenyl | H | cyclo-propyl | 3-CF₃-phenyl | S | S |
| 2,4-(Cl,Cl)-phenyl | H | cyclo-propyl | 2,4-(Cl,Cl)-phenyl | S | S |
| 2,4-(Cl,Cl)-phenyl | H | cyclo-propyl | 2-pyridyl | S | S |
| 2,4-(Cl,Cl)-phenyl | H | cyclo-propyl | ethyl | S | S |
| 2-thienyl | H | cyclo-propyl | iso-propyl | S | S |
| 2-thienyl | H | cyclo-propyl | butyl | S | S |
| 2-thienyl | H | cyclo-propyl | tert.-butyl | S | S |
| 3-pyridyl | H | cyclo-propyl | phenyl | S | S |
| 3-pyridyl | H | cyclo-propyl | 4-F-phenyl | S | S |
| 3-pyridyl | H | cyclo-propyl | 3-CF₃-phenyl | S | S |
| chloro | H | tert.-butyl | 4-hydroxy-2-butynyl | O | O |
| chloro | H | tert.-butyl | N=C(C₂H₅)₂ | O | O |
| chloro | H | tert.-butyl | N=C(cyclo-C₃H₅)₂ | O | O |
| chloro | H | tert.-butyl | 2-butanimino | O | O |
| chloro | H | tert.-butyl | cyclohexanimino | O | O |
| chloro | H | tert.-butyl | cyclooctanimino | O | O |

TABLE A-1/B-1-continued

| R¹ | R³ | R⁴ | R⁵ | X | Y |
|---|---|---|---|---|---|
| methyl | H | tert.-butyl | $N=CH-C_6H_5$ | O | O |
| methyl | H | tert.-butyl | 2-furyl-methanimino | O | O |
| methyl | H | tert.-butyl | $CH_2CH_2N(CH_3)_2$ | O | O |
| methyl | H | tert.-butyl | $CH_2CH_2N^+(CH_3)_3I^-$ | O | O |
| methyl | H | tert.-butyl | $CH_2CF_3$ | O | O |
| methyl | H | tert.-butyl | $CH_2CH_2Cl$ | O | O |
| methyl | H | tert.-butyl | $CH_2CH_2CN$ | O | O |
| iso-propyl | H | tert.-butyl | $CH_2CCl_3$ | O | O |
| iso-propyl | H | tert.-butyl | $CH_2CH_2Si(CH_3)_3$ | O | O |
| iso-propyl | H | tert.-butyl | $CH_2CH_2O-N=C(CH_3)_2$ | O | O |
| iso-propyl | H | tert.-butyl | $CH_2PO(OC_2H_5)_2$ | O | O |
| iso-propyl | H | tert.-butyl | $CH(CH_3)CH(OCH_3)_2$ | O | O |
| iso-propyl | H | tert.-butyl | $CH_2-CON(C_2H_5)_2$ | O | O |
| iso-propyl | H | tert.-butyl | benzyl | O | O |
| cyclo-propyl | H | tert.-butyl | 2,4-(Cl,Cl)-benzyl | O | O |
| cyclo-propyl | H | tert.-butyl | 3-pyridyl-methyl | O | O |
| cyclo-propyl | H | tert.-butyl | 2-thienyl-methyl | O | O |
| cyclo-propyl | H | tert.-butyl | 2-tetrahydrofuranyl-methyl | O | O |
| cyclo-propyl | H | tert.-butyl | 2-furanyl-methyl | O | O |
| cyclo-propyl | H | tert.-butyl | 2-pyridyl-methyl | O | O |
| cyclo-propyl | H | tert.-butyl | phenyl | O | O |
| allyl | H | tert.-butyl | 4-F-phenyl | O | O |
| allyl | H | tert.-butyl | 4-trifluoromethylphenyl | O | O |
| allyl | H | tert.-butyl | $2-NO_2-4-F$-phenyl | O | O |
| allyl | H | tert.-butyl | $3,5-(CF_3,CF_3)$-phenyl | O | O |
| allyl | H | tert.-butyl | $4-OCH_3$-phenyl | O | O |
| allyl | H | tert.-butyl | $4-OCF_3$-phenyl | O | O |
| allyl | H | tert.-butyl | $4-NHCOCH_3$-phenyl | O | O |
| ethynyl | H | tert.-butyl | 2-tetrahydropyranyl | O | O |
| ethynyl | H | tert.-butyl | 2-tetrahydropyranyl | O | O |
| ethynyl | H | tert.-butyl | 1-benzotriazolyl | O | O |
| ethynyl | H | tert.-butyl | methyl | O | O |
| ethynyl | H | tert.-butyl | ethyl | O | O |
| ethynyl | H | tert.-butyl | n-propyl | O | O |
| ethynyl | H | tert.-butyl | iso-propyl | O | O |
| methoxy | H | tert.-butyl | n-butyl | O | O |
| methoxy | H | tert.-butyl | iso-butyl | O | O |
| methoxy | H | tert.-butyl | sec.-butyl | O | O |
| methoxy | H | tert.-butyl | tert.-butyl | O | O |
| methoxy | H | tert.-butyl | cyclo-hexyl | O | O |
| methoxy | H | tert.-butyl | cyclopropylmethyl | O | O |
| methoxy | H | tert.-butyl | ethoxymethyl | O | O |
| 4-Cl-phenoxy | H | tert.-butyl | 2-methoxy-ethoxy-methyl | O | O |
| 4-Cl-phenoxy | H | tert.-butyl | benzyloxymethyl | O | O |
| 4-Cl-phenoxy | H | tert.-butyl | (4-bromobenzoyl)-methyl | O | O |
| 4-Cl-phenoxy | H | tert.-butyl | (4-methoxybenzoyl)-methyl | O | O |
| 4-Cl-phenoxy | H | tert.-butyl | phthalimidomethyl | O | O |
| 4-Cl-phenoxy | H | tert.-butyl | methylthiomethyl | O | O |
| 4-Cl-phenoxy | H | tert.-butyl | 2-thiomethyl-ethyl | O | O |
| phenylthio | H | tert.-butyl | $CH(C_6H_5)COOCH_3$ | O | O |
| phenylthio | H | tert.-butyl | phenylethyl | O | O |
| phenylthio | H | tert.-butyl | 4-F-phenylethyl | O | O |
| phenylthio | H | tert.-butyl | phthalimido | O | O |
| phenylthio | H | tert.-butyl | tetrahydrophthalimido | O | O |
| phenylthio | H | tert.-butyl | maleiimido | O | O |
| phenylthio | H | tert.-butyl | succinimido | O | O |
| 2,4-(Cl,Cl)-phenyl | H | tert.-butyl | piperidino | O | O |
| 2,4-(Cl,Cl)-phenyl | H | tert.-butyl | $Li^+$ | O | O |
| 2,4-(Cl,Cl)-phenyl | H | tert.-butyl | $Na^+$ | O | O |
| 2,4-(Cl,Cl)-phenyl | H | tert.-butyl | $K^+$ | O | O |
| 2,4-(Cl,Cl)-phenyl | H | tert.-butyl | $NH_4^+$ | O | O |
| 2,4-(Cl,Cl)-phenyl | H | tert.-butyl | diisopropylammonium | O | O |
| 2,4-(Cl,Cl)-phenyl | H | tert.-butyl | 2-hydroxy-ethyl-ammonium | O | O |
| 2-thienyl | H | tert.-butyl | allyl | O | O |
| 2-thienyl | H | tert.-butyl | methallyl | O | O |
| 2-thienyl | H | tert.-butyl | 2-chloroallyl | O | O |
| 2-thienyl | H | tert.-butyl | propargyl | O | O |
| 2-thienyl | H | tert.-butyl | 3-iodopropargyl | O | O |
| chloro | H | cyclo-propyl | 4-hydroxy-2-butynyl | O | O |
| chloro | H | cyclo-propyl | $N=C(C_2H_5)_2$ | O | O |
| chloro | H | cyclo-propyl | $N=C(cyclo-C_3H_5)_2$ | O | O |

TABLE A-1/B-1-continued

Ia or Ib

| R¹ | R³ | R⁴ | R⁵ | X | Y |
|---|---|---|---|---|---|
| chloro | H | cyclo-propyl | 2-butanimino | O | O |
| chloro | H | cyclo-propyl | cyclohexanimino | O | O |
| chloro | H | cyclo-propyl | cyclooctanimino | O | O |
| methyl | H | cyclo-propyl | N=CH—C$_6$H$_5$ | O | O |
| methyl | H | cyclo-propyl | 2-furyl-methanimino | O | O |
| methyl | H | cyclo-propyl | CH$_2$CH$_2$N(CH$_3$)$_2$ | O | O |
| methyl | H | cyclo-propyl | CH$_2$CH$_2$N$^+$(CH$_3$)$_3$I$^-$ | O | O |
| methyl | H | cyclo-propyl | CH$_2$CF$_3$ | O | O |
| methyl | H | cyclo-propyl | CH$_2$CH$_2$Cl | O | O |
| methyl | H | cyclo-propyl | CH$_2$CH$_2$CN | O | O |
| iso-propyl | H | cyclo-propyl | CH$_2$CCl$_3$ | O | O |
| iso-propyl | H | cyclo-propyl | CH$_2$CH$_2$Si(CH$_3$)$_3$ | O | O |
| iso-propyl | H | cyclo-propyl | CH$_2$CH$_2$O—N=C(CH$_3$)$_2$ | O | O |
| iso-propyl | H | cyclo-propyl | CH$_2$PO(OC$_2$H$_5$)$_2$ | O | O |
| iso-propyl | H | cyclo-propyl | CH(CH$_3$)CH(OCH$_3$)$_2$ | O | O |
| iso-propyl | H | cyclo-propyl | CH$_2$—CON(C$_2$H$_5$)$_2$ | O | O |
| iso-propyl | H | cyclo-propyl | benzyl | O | O |
| cyclo-propyl | H | cyclo-propyl | 2,4-(Cl,Cl)-benzyl | O | O |
| cyclo-propyl | H | cyclo-propyl | 3-pyridyl-methyl | O | O |
| cyclo-propyl | H | cyclo-propyl | 2-thienyl-methyl | O | O |
| cyclo-propyl | H | cyclo-propyl | 2-tetrahydrofuranyl-methyl | O | O |
| cyclo-propyl | H | cyclo-propyl | 2-furanyl-methyl | O | O |
| cyclo-propyl | H | cyclo-propyl | 2-pyridyl-methyl | O | O |
| cyclo-propyl | H | cyclo-propyl | phenyl | O | O |
| allyl | H | cyclo-propyl | 4-F-phenyl | O | O |
| allyl | H | cyclo-propyl | 4-trifluoromethylphenyl | O | O |
| allyl | H | cyclo-propyl | 2-NO$_2$-4-F-phenyl | O | O |
| allyl | H | cyclo-propyl | 3,5-(CF$_3$,CF$_3$)-phenyl | O | O |
| allyl | H | cyclo-propyl | 4-OCH$_3$-phenyl | O | O |
| allyl | H | cyclo-propyl | 4-OCF$_3$-phenyl | O | O |
| allyl | H | cyclo-propyl | 4-NHCOCH$_3$-phenyl | O | O |
| ethynyl | H | cyclo-propyl | 2-tetrahydropyranyl | O | O |
| ethynyl | H | cyclo-propyl | 2-tetrahydropyranyl | O | O |
| ethynyl | H | cyclo-propyl | 1-benzotriazolyl | O | O |
| ethynyl | H | cyclo-propyl | methyl | O | O |
| ethynyl | H | cyclo-propyl | ethyl | O | O |
| ethynyl | H | cyclo-propyl | n-propyl | O | O |
| ethynyl | H | cyclo-propyl | iso-propyl | O | O |
| methoxy | H | cyclo-propyl | n-butyl | O | O |
| methoxy | H | cyclo-propyl | iso-butyl | O | O |
| methoxy | H | cyclo-propyl | sec.-butyl | O | O |
| methoxy | H | cyclo-propyl | tert.-butyl | O | O |
| methoxy | H | cyclo-propyl | cyclo-hexyl | O | O |
| methoxy | H | cyclo-propyl | cyclopropylmethyl | O | O |
| methoxy | H | cyclo-propyl | ethoxymethyl | O | O |
| 4-Cl-phenoxy | H | cyclo-propyl | 2-methoxy-ethoxy-methyl | O | O |
| 4-Cl-phenoxy | H | cyclo-propyl | benzyloxymethyl | O | O |
| 4-Cl-phenoxy | H | cyclo-propyl | (4-bromobenzoyl)-methyl | O | O |
| 4-Cl-phenoxy | H | cyclo-propyl | (4-methoxybenzoyl)-methyl | O | O |
| 4-Cl-phenoxy | H | cyclo-propyl | phthalimidomethyl | O | O |
| 4-Cl-phenoxy | H | cyclo-propyl | methylthiomethyl | O | O |
| 4-Cl-phenoxy | H | cyclo-propyl | 2-thiomethyl-ethyl | O | O |
| phenylthio | H | cyclo-propyl | CH(C$_6$H$_5$)COOCH$_3$ | O | O |
| phenylthio | H | cyclo-propyl | phenylethyl | O | O |
| phenylthio | H | cyclo-propyl | 4-F-phenylethyl | O | O |
| phenylthio | H | cyclo-propyl | phthalimido | O | O |
| phenylthio | H | cyclo-propyl | tetrahydrophthalimido | O | O |
| phenylthio | H | cyclo-propyl | maleiimido | O | O |
| phenylthio | H | cyclo-propyl | succinimido | O | O |
| 2,4-(Cl,Cl)-phenyl | H | cyclo-propyl | piperidino | O | O |
| 2,4-(Cl,Cl)-phenyl | H | cyclo-propyl | Li$^+$ | O | O |
| 2,4-(Cl,Cl)-phenyl | H | cyclo-propyl | Na$^+$ | O | O |
| 2,4-(Cl,Cl)-phenyl | H | cyclo-propyl | K$^+$ | O | O |
| 2,4-(Cl,Cl)-phenyl | H | cyclo-propyl | NH$_4$$^+$ | O | O |
| 2,4-(Cl,Cl)-phenyl | H | cyclo-propyl | diisopropylammonium | O | O |
| 2,4-(Cl,Cl)-phenyl | H | cyclo-propyl | 2-hydroxyethyl-ammonium | O | O |
| 2-thienyl | H | cyclo-propyl | allyl | O | O |
| 2-thienyl | H | cyclo-propyl | methallyl | O | O |
| 2-thienyl | H | cyclo-propyl | 2-chloroallyl | O | O |
| 2-thienyl | H | cyclo-propyl | propargyl | O | O |
| 2-thienyl | H | cyclo-propyl | 3-iodopropargyl | O | O |

TABLE A-1/B-1-continued $$\text{Ia} \quad \text{or} \quad \text{Ib}$$

| R¹ | R³ | R⁴ | R⁵ | X | Y |
|---|---|---|---|---|---|
| H | H | tert.-butyl | —N=C(CH₃)₂ | O | O |
| F | H | tert.-butyl | —N=C(CH₃)₂ | O | O |
| Cl | H | tert.-butyl | —N=C(CH₃)₂ | O | O |
| methyl | H | tert.-butyl | —N=C(CH₃)₂ | O | O |
| ethyl | H | tert.-butyl | —N=C(CH₃)₂ | O | O |
| n-propyl | H | tert.-butyl | —N=C(CH₃)₂ | O | O |
| iso-propyl | H | tert.-butyl | —N=C(CH₃)₂ | O | O |
| n-butyl | H | tert.-butyl | —N=C(CH₃)₂ | O | O |
| iso-butyl | H | tert.-butyl | —N=C(CH₃)₂ | O | O |
| sec.-butyl | H | tert.-butyl | —N=C(CH₃)₂ | O | O |
| tert.-butyl | H | tert.-butyl | —N=C(CH₃)₂ | O | O |
| cyclo-propyl | H | tert.-butyl | —N=C(CH₃)₂ | O | O |
| cyclo-butyl | H | tert.-butyl | —N=C(CH₃)₂ | O | O |
| cyclo-pentyl | H | tert.-butyl | —N=C(CH₃)₂ | O | O |
| cyclo-hexyl | H | tert.-butyl | —N=C(CH₃)₂ | O | O |
| cyclo-heptyl | H | tert.-butyl | —N=C(CH₃)₂ | O | O |
| cyclo-octyl | H | tert.-butyl | —N=C(CH₃)₂ | O | O |
| 1-methylcyclopropyl | H | tert.-butyl | —N=C(CH₃)₂ | O | O |
| trifluoromethyl | H | tert.-butyl | —N=C(CH₃)₂ | O | O |
| chlorodifluoromethyl | H | tert.-butyl | —N=C(CH₃)₂ | O | O |
| pentafluoromethyl | H | tert.-butyl | —N=C(CH₃)₂ | O | O |
| iso-propoxy | H | tert.-butyl | —N=C(CH₃)₂ | O | O |
| methoxymethyl | H | tert.-butyl | —N=C(CH₃)₂ | O | O |
| 1-methylmethoxymethyl | H | tert.-butyl | —N=C(CH₃)₂ | O | O |
| 1-methylmethoxyethyl | H | tert.-butyl | —N=C(CH₃)₂ | O | O |
| ethoxymethyl | H | tert.-butyl | —N=C(CH₃)₂ | O | O |
| vinyl | H | tert.-butyl | —N=C(CH₃)₂ | O | O |
| allyl | H | tert.-butyl | —N=C(CH₃)₂ | O | O |
| methallyl | H | tert.-butyl | —N=C(CH₃)₂ | O | O |
| crotyl | H | tert.-butyl | —N=C(CH₃)₂ | O | O |
| ethynyl | H | tert.-butyl | —N=C(CH₃)₂ | O | O |
| propargyl | H | tert.-butyl | —N=C(CH₃)₂ | O | O |
| phenylethynyl | H | tert.-butyl | —N=C(CH₃)₂ | O | O |
| methoxy | H | tert.-butyl | —N=C(CH₃)₂ | O | O |
| ethoxy | H | tert.-butyl | —N=C(CH₃)₂ | O | O |
| trifluoromethoxy | H | tert.-butyl | —N=C(CH₃)₂ | O | O |
| methylthio | H | tert.-butyl | —N=C(CH₃)₂ | O | O |
| trifluoromethylthio | H | tert.-butyl | —N=C(CH₃)₂ | O | O |
| phenoxy | H | tert.-butyl | —N=C(CH₃)₂ | O | O |
| 4-Cl-phenoxy | H | tert.-butyl | —N=C(CH₃)₂ | O | O |
| 2,4-(Cl,Cl)-phenoxy | H | tert.-butyl | —N=C(CH₃)₂ | O | O |
| 4-CF₃-phenoxy | H | tert.-butyl | —N=C(CH₃)₂ | O | O |
| phenyl | H | tert.-butyl | —N=C(CH₃)₂ | O | O |
| 2-F-phenylthio | H | tert.-butyl | —N=C(CH₃)₂ | O | O |
| 3-F-phenyl | H | tert.-butyl | —N=C(CH₃)₂ | O | O |
| 2,4-(F,F)-phenyl | H | tert.-butyl | —N=C(CH₃)₂ | O | O |
| 2-Cl-phenyl | H | tert.-butyl | —N=C(CH₃)₂ | O | O |
| 3-Cl-phenyl | H | tert.-butyl | —N=C(CH₃)₂ | O | O |
| 2,4-(Cl,Cl)-phenyl | H | tert.-butyl | —N=C(CH₃)₂ | O | O |
| 2-CH₃-phenyl | H | tert.-butyl | —N=C(CH₃)₂ | O | O |
| 3-CH₃-phenyl | H | tert.-butyl | —N=C(CH₃)₂ | O | O |
| 4-CH₃-phenyl | H | tert.-butyl | —N=C(CH₃)₂ | O | O |
| 2,4-(CH₃,CH₃)-phenyl | H | tert.-butyl | —N=C(CH₃)₂ | O | O |
| 2,4,6-(CH₃,CH₃,CH₃)-phenyl | H | tert.-butyl | —N=C(CH₃)₂ | O | O |
| 2-CF₃-phenyl | H | tert.-butyl | —N=C(CH₃)₂ | O | O |
| 2-OCH₃-phenyl | H | tert.-butyl | —N=C(CH₃)₂ | O | O |
| 2,4-(OCH₃,OCH₃)-phenyl | H | tert.-butyl | —N=C(CH₃)₂ | O | O |
| 4-OCF₃-phenyl | H | tert.-butyl | —N=C(CH₃)₂ | O | O |
| 4-SCH₃-phenyl | H | tert.-butyl | —N=C(CH₃)₂ | O | O |
| 3-SCF₃-phenyl | H | tert.-butyl | —N=C(CH₃)₂ | O | O |
| 2,4-(NO₂,NO₂)-phenyl | H | tert.-butyl | —N=C(CH₃)₂ | O | O |
| 4-NO₂-phenyl | H | tert.-butyl | —N=C(CH₃)₂ | O | O |
| 2-thienyl | H | tert.-butyl | —N=C(CH₃)₂ | O | O |
| 3-thienyl | H | tert.-butyl | —N=C(CH₃)₂ | O | O |
| 2-furanyl | H | tert.-butyl | —N=C(CH₃)₂ | O | O |
| 3-furanyl | H | tert.-butyl | —N=C(CH₃)₂ | O | O |
| 2-tetrahydrofuranyl | H | tert.-butyl | —N=C(CH₃)₂ | O | O |
| 3-tetrahydrofuranyl | H | tert.-butyl | —N=C(CH₃)₂ | O | O |
| 2-pyridyl | H | tert.-butyl | —N=C(CH₃)₂ | O | O |
| 3-pyridyl | H | tert.-butyl | —N=C(CH₃)₂ | O | O |
| 4-pyridyl | H | tert.-butyl | —N=C(CH₃)₂ | O | O |

TABLE A-1/B-1-continued

| R$^1$ | R$^3$ | R$^4$ | R$^5$ | X | Y |
|---|---|---|---|---|---|
| 2-tetrahydropyranyl | H | tert.-butyl | $-N=C(CH_3)_2$ | O | O |
| 3-tetrahydropyranyl | H | tert.-butyl | $-N=C(CH_3)_2$ | O | O |
| 4-tetrahydropyranyl | H | tert.-butyl | $-N=C(CH_3)_2$ | O | O |
| H | H | cyclo-propyl | $-N=C(CH_3)_2$ | O | O |
| F | H | cyclo-propyl | $-N=C(CH_3)_2$ | O | O |
| Cl | H | cyclo-propyl | $-N=C(CH_3)_2$ | O | O |
| methyl | H | cyclo-propyl | $-N=C(CH_3)_2$ | O | O |
| ethyl | H | cyclo-propyl | $-N=C(CH_3)_2$ | O | O |
| n-propyl | H | cyclo-propyl | $-N=C(CH_3)_2$ | O | O |
| iso-propyl | H | cyclo-propyl | $-N=C(CH_3)_2$ | O | O |
| n-butyl | H | cyclo-propyl | $-N=C(CH_3)_2$ | O | O |
| iso-butyl | H | cyclo-propyl | $-N=C(CH_3)_2$ | O | O |
| sec.-butyl | H | cyclo-propyl | $-N=C(CH_3)_2$ | O | O |
| tert.-butyl | H | cyclo-propyl | $-N=C(CH_3)_2$ | O | O |
| cyclo-propyl | H | cyclo-propyl | $-N=C(CH_3)_2$ | O | O |
| cyclo-butyl | H | cyclo-propyl | $-N=C(CH_3)_2$ | O | O |
| cyclo-pentyl | H | cyclo-propyl | $-N=C(CH_3)_2$ | O | O |
| cyclo-hexyl | H | cyclo-propyl | $-N=C(CH_3)_2$ | O | O |
| cyclo-heptyl | H | cyclo-propyl | $-N=C(CH_3)_2$ | O | O |
| cyclo-octyl | H | cyclo-propyl | $-N=C(CH_3)_2$ | O | O |
| 1-methylcyclopropyl | H | cyclo-propyl | $-N=C(CH_3)_2$ | O | O |
| trifluoromethyl | H | cyclo-propyl | $-N=C(CH_3)_2$ | O | O |
| chlorodifluoromethyl | H | cyclo-propyl | $-N=C(CH_3)_2$ | O | O |
| pentafluoromethyl | H | cyclo-propyl | $-N=C(CH_3)_2$ | O | O |
| iso-propoxy | H | cyclo-propyl | $-N=C(CH_3)_2$ | O | O |
| methoxymethyl | H | cyclo-propyl | $-N=C(CH_3)_2$ | O | O |
| 1-methylmethoxymethyl | H | cyclo-propyl | $-N=C(CH_3)_2$ | O | O |
| 1-methylmethoxyethyl | H | cyclo-propyl | $-N=C(CH_3)_2$ | O | O |
| ethoxymethyl | H | cyclo-propyl | $-N=C(CH_3)_2$ | O | O |
| vinyl | H | cyclo-propyl | $-N=C(CH_3)_2$ | O | O |
| allyl | H | cyclo-propyl | $-N=C(CH_3)_2$ | O | O |
| methallyl | H | cyclo-propyl | $-N=C(CH_3)_2$ | O | O |
| crotyl | H | cyclo-propyl | $-N=C(CH_3)_2$ | O | O |
| ethynyl | H | cyclo-propyl | $-N=C(CH_3)_2$ | O | O |
| propargyl | H | cyclo-propyl | $-N=C(CH_3)_2$ | O | O |
| phenylethynyl | H | cyclo-propyl | $-N=C(CH_3)_2$ | O | O |
| methoxy | H | cyclo-propyl | $-N=C(CH_3)_2$ | O | O |
| ethoxy | H | cyclo-propyl | $-N=C(CH_3)_2$ | O | O |
| trifluoromethoxy | H | cyclo-propyl | $-N=C(CH_3)_2$ | O | O |
| methylthio | H | cyclo-propyl | $-N=C(CH_3)_2$ | O | O |
| trifluoromethylthio | H | cyclo-propyl | $-N=C(CH_3)_2$ | O | O |
| phenoxy | H | cyclo-propyl | $-N=C(CH_3)_2$ | O | O |
| 4-Cl-phenoxy | H | cyclo-propyl | $-N=C(CH_3)_2$ | O | O |
| 2,4-(Cl,Cl)-phenoxy | H | cyclo-propyl | $-N=C(CH_3)_2$ | O | O |
| 4-CF$_3$-phenoxy | H | cyclo-propyl | $-N=C(CH_3)_2$ | O | O |
| phenyl | H | cyclo-propyl | $-N=C(CH_3)_2$ | O | O |
| 2-F-phenylthio | H | cyclo-propyl | $-N=C(CH_3)_2$ | O | O |
| 3-F-phenyl | H | cyclo-propyl | $-N=C(CH_3)_2$ | O | O |
| 2,4-(F,F)-phenyl | H | cyclo-propyl | $-N=C(CH_3)_2$ | O | O |
| 2-Cl-phenyl | H | cyclo-propyl | $-N=C(CH_3)_2$ | O | O |
| 3-Cl-phenyl | H | cyclo-propyl | $-N=C(CH_3)_2$ | O | O |
| 2,4-(Cl,Cl)-phenyl | H | cyclo-propyl | $-N=C(CH_3)_2$ | O | O |
| 2-CH$_3$-phenyl | H | cyclo-propyl | $-N=C(CH_3)_2$ | O | O |
| 3-CH$_3$-phenyl | H | cyclo-propyl | $-N=C(CH_3)_2$ | O | O |
| 4-CH$_3$-phenyl | H | cyclo-propyl | $-N=C(CH_3)_2$ | O | O |
| 2,4-(CH$_3$,CH$_3$)-phenyl | H | cyclo-propyl | $-N=C(CH_3)_2$ | O | O |
| 2,4,6-(CH$_3$,CH$_3$,CH$_3$)-phenyl | H | cyclo-propyl | $-N=C(CH_3)_2$ | O | O |
| 2-CF$_3$-phenyl | H | cyclo-propyl | $-N=C(CH_3)_2$ | O | O |
| 2-OCH$_3$-phenyl | H | cyclo-propyl | $-N=C(CH_3)_2$ | O | O |
| 2,4-(OCH$_3$,OCH$_3$)-phenyl | H | cyclo-propyl | $-N=C(CH_3)_2$ | O | O |
| 4-OCF$_3$-phenyl | H | cyclo-propyl | $-N=C(CH_3)_2$ | O | O |
| 4-SCH$_3$-phenyl | H | cyclo-propyl | $-N=C(CH_3)_2$ | O | O |
| 3-SCF$_3$-phenyl | H | cyclo-propyl | $-N=C(CH_3)_2$ | O | O |
| 2,4-(NO$_2$,NO$_2$)-phenyl | H | cyclo-propyl | $-N=C(CH_3)_2$ | O | O |
| 4-NO$_2$-phenyl | H | cyclo-propyl | $-N=C(CH_3)_2$ | O | O |
| 2-thienyl | H | cyclo-propyl | $-N=C(CH_3)_2$ | O | O |
| 3-thienyl | H | cyclo-propyl | $-N=C(CH_3)_2$ | O | O |
| 2-furanyl | H | cyclo-propyl | $-N=C(CH_3)_2$ | O | O |
| 3-furanyl | H | cyclo-propyl | $-N=C(CH_3)_2$ | O | O |
| 2-tetrahydrofuranyl | H | cyclo-propyl | $-N=C(CH_3)_2$ | O | O |
| 3-tetrahydrofuranyl | H | cyclo-propyl | $-N=C(CH_3)_2$ | O | O |

TABLE A-1/B-1-continued

| R¹ | R³ | R⁴ | R⁵ | X | Y |
|---|---|---|---|---|---|
| 2-pyridyl | H | cyclo-propyl | —N=C(CH₃)₂ | O | O |
| 3-pyridyl | H | cyclo-propyl | —N=C(CH₃)₂ | O | O |
| 4-pyridyl | H | cyclo-propyl | —N=C(CH₃)₂ | O | O |
| 2-tetrahydropyranyl | H | cyclo-propyl | —N=C(CH₃)₂ | O | O |
| 3-tetrahydropyranyl | H | cyclo-propyl | —N=C(CH₃)₂ | O | O |
| 4-tetrahydropyranyl | H | cyclo-propyl | —N=C(CH₃)₂ | O | O |
| chloro | H | methyl | H | O | O |
| chloro | H | ethyl | H | O | O |
| chloro | H | n-propyl | H | O | O |
| chloro | H | iso-propyl | H | O | O |
| chloro | H | n-butyl | H | O | O |
| chloro | H | iso-butyl | H | O | O |
| methyl | H | sec.-butyl | H | O | O |
| methyl | H | n-pentyl | H | O | O |
| methyl | H | 2-pentyl | H | O | O |
| methyl | H | 3-pentyl | H | O | O |
| methyl | H | n-hexyl | H | O | O |
| methyl | H | 2-hexyl | H | O | O |
| iso-propyl | H | 3-hexyl | H | O | O |
| iso-propyl | H | 2-methyl-2-pentyl | H | O | O |
| iso-propyl | H | cyclo-propylmethyl | H | O | O |
| iso-propyl | H | cyclo-butyl | H | O | O |
| iso-propyl | H | cyclo-pentyl | H | O | O |
| iso-propyl | H | cyclo-hexyl | H | O | O |
| cyclo-propyl | H | 1-methylcyclohexyl | H | O | O |
| cyclo-propyl | H | 3-trifluoromethylcyclohexyl | H | O | O |
| cyclo-propyl | H | allyl | H | O | O |
| cyclo-propyl | H | 1-buten-3-yl | H | O | O |
| cyclo-propyl | H | crotyl | H | O | O |
| cyclo-propyl | H | propargyl | H | O | O |
| allyl | H | 1-butyn-3-yl | H | O | O |
| allyl | H | 3-methyl-1-butyn-3-yl | H | O | O |
| allyl | H | 2-pentyn-4-yl | H | O | O |
| allyl | H | benzyl | H | O | O |
| allyl | H | 2-phenylethyl | H | O | O |
| allyl | H | 2-methylthioethyl | H | O | O |
| ethynyl | H | 2-chloroethyl | H | O | O |
| ethynyl | H | 2-methoxyethyl | H | O | O |
| ethynyl | H | 2-(N,N-dimethylamino)ethyl | H | O | O |
| ethynyl | H | phenyl | H | O | O |
| ethynyl | H | 2-CH₃-phenyl | H | O | O |
| ethynyl | H | 4-CH₃-phenyl | H | O | O |
| methoxy | H | 2,4-(CH₃,CH₃)-phenyl | H | O | O |
| methoxy | H | 2,3,5-(CH₃,CH₃,CH₃)-phenyl | H | O | O |
| methoxy | H | 3-CF₃-phenyl | H | O | O |
| methoxy | H | 3-F-phenyl | H | O | O |
| methoxy | H | 2-Cl-phenyl | H | O | O |
| methoxy | H | 4-Cl-phenyl | H | O | O |
| 4-Cl-phenoxy | H | 2,4-(F,F)-phenyl | H | O | O |
| 4-Cl-phenoxy | H | 2,3,5-(Cl,Cl,Cl)-phenyl | H | O | O |
| 4-Cl-phenoxy | H | 2-CN-phenyl | H | O | O |
| 4-Cl-phenoxy | H | 2-OCH₃-phenyl | H | O | O |
| 4-Cl-phenoxy | H | 2,3-(OCH₃,OCH₃)-phenyl | H | O | O |
| 4-Cl-phenoxy | H | 3,4,5-(OCH₃,OCH₃,OCH₃)-phenyl | H | O | O |
| phenylthio | H | 3-OCF₃-phenyl | H | O | O |
| phenylthio | H | 4-OCF₂CHF₂-phenyl | H | O | O |
| phenylthio | H | 2-SCH₃-phenyl | H | O | O |
| phenylthio | H | 2,4-(SCH₃,SCH₃)-phenyl | H | O | O |
| phenylthio | H | 2-SCF₃-phenyl | H | O | O |
| phenylthio | H | 4-NO₂-phenyl | H | O | O |
| 2,4-(Cl,Cl)-phenyl | H | 2,4-(NO₂,NO₂)-phenyl | H | O | O |
| 2,4-(Cl,Cl)-phenyl | H | 2-CHO-phenyl | H | O | O |
| 2,4-(Cl,Cl)-phenyl | H | 3-COCH₃-phenyl | H | O | O |
| 2,4-(Cl,Cl)-phenyl | H | 3-COCF₃-phenyl | H | O | O |
| 2,4-(Cl,Cl)-phenyl | H | 1-naphthyl | H | O | O |
| 2,4-(Cl,Cl)-phenyl | H | 2-naphthyl | H | O | O |
| 2-thienyl | H | piperidimo | H | O | O |
| 2-thienyl | H | 3-tetrahydrofuranyl | H | O | O |
| 2-thienyl | H | 4-tetrahydrofuranyl | H | O | O |
| 2-thienyl | H | 2-thiazolyl | H | O | O |
| 2-thienyl | H | 5-CH₃-2-thiazolyl | H | O | O |

TABLE A-1/B-1-continued

| R¹ | R³ | R⁴ | R⁵ | X | Y |
|---|---|---|---|---|---|
| 2-thienyl | H | 4-CH₃-5-COOH-2-thiazolyl | H | O | O |
| 3-pyridyl | H | methyl | H | O | O |
| 3-pyridyl | H | ethyl | H | O | O |
| 3-pyridyl | H | n-propyl | H | O | O |
| 3-pyridyl | H | iso-propyl | H | O | O |
| 3-pyridyl | H | n-butyl | H | O | O |
| 3-pyridyl | H | iso-butyl | H | O | O |
| iso-propyl | methyl | sec.-butyl | H | O | O |
| iso-propyl | methyl | n-pentyl | H | O | O |
| iso-propyl | methyl | 2-pentyl | H | O | O |
| iso-propyl | methyl | 3-pentyl | H | O | O |
| iso-propyl | methyl | n-hexyl | H | O | O |
| iso-propyl | methyl | 2-hexyl | H | O | O |
| iso-propyl | methyl | 3-hexyl | H | O | O |
| chloro | H | methyl | —N=C(CH₃)₂ | O | O |
| chloro | H | ethyl | —N=C(CH₃)₂ | O | O |
| chloro | H | n-propyl | —N=C(CH₃)₂ | O | O |
| chloro | H | iso-propyl | —N=C(CH₃)₂ | O | O |
| chloro | H | n-butyl | —N=C(CH₃)₂ | O | O |
| chloro | H | iso-butyl | —N=C(CH₃)₂ | O | O |
| methyl | H | sec.-butyl | —N=C(CH₃)₂ | O | O |
| methyl | H | n-pentyl | —N=C(CH₃)₂ | O | O |
| methyl | H | 2-pentyl | —N=C(CH₃)₂ | O | O |
| methyl | H | 3-pentyl | —N=C(CH₃)₂ | O | O |
| methyl | H | n-hexyl | —N=C(CH₃)₂ | O | O |
| methyl | H | 2-hexyl | —N=C(CH₃)₂ | O | O |
| iso-propyl | H | 3-hexyl | —N=C(CH₃)₂ | O | O |
| iso-propyl | H | 2-methyl-2-pentyl | —N=C(CH₃)₂ | O | O |
| iso-propyl | H | cyclo-propylmethyl | —N=C(CH₃)₂ | O | O |
| iso-propyl | H | cyclo-butyl | —N=C(CH₃)₂ | O | O |
| iso-propyl | H | cyclo-pentyl | —N=C(CH₃)₂ | O | O |
| iso-propyl | H | cyclo-hexyl | —N=C(CH₃)₂ | O | O |
| cyclo-propyl | H | 1-methylcyclohexyl | —N=C(CH₃)₂ | O | O |
| cyclo-propyl | H | 3-trifluoromethylcyclohexyl | —N=C(CH₃)₂ | O | O |
| cyclo-propyl | H | allyl | —N=C(CH₃)₂ | O | O |
| cyclo-propyl | H | 1-buten-3-yl | —N=C(CH₃)₂ | O | O |
| cyclo-propyl | H | crotyl | —N=C(CH₃)₂ | O | O |
| cyclo-propyl | H | propargyl | —N=C(CH₃)₂ | O | O |
| allyl | H | 1-butyn-3-yl | —N=C(CH₃)₂ | O | O |
| allyl | H | 3-methyl-1-butyn-3-yl | —N=C(CH₃)₂ | O | O |
| allyl | H | 2-pentyn-4-yl | —N=C(CH₃)₂ | O | O |
| allyl | H | benzyl | —N=C(CH₃)₂ | O | O |
| allyl | H | 2-phenylethyl | —N=C(CH₃)₂ | O | O |
| allyl | H | 2-methylthioethyl | —N=C(CH₃)₂ | O | O |
| ethynyl | H | 2-chloroethyl | —N=C(CH₃)₂ | O | O |
| ethynyl | H | 2-methoxyethyl | —N=C(CH₃)₂ | O | O |
| ethynyl | H | 2-(N,N-dimethylamino)-ethyl | —N=C(CH₃)₂ | O | O |
| ethynyl | H | phenyl | —N=C(CH₃)₂ | O | O |
| ethynyl | H | 2-CH₃-phenyl | —N=C(CH₃)₂ | O | O |
| ethynyl | H | 4-CH₃-phenyl | —N=C(CH₃)₂ | O | O |
| methoxy | H | 2,4-(CH₃,CH₃)-phenyl | —N=C(CH₃)₂ | O | O |
| methoxy | H | 2,3,5-(CH₃,CH₃,CH₃)-phenyl | —N=C(CH₃)₂ | O | O |
| methoxy | H | 3-CF₃-phenyl | —N=C(CH₃)₂ | O | O |
| methoxy | H | 3-F-phenyl | —N=C(CH₃)₂ | O | O |
| methoxy | H | 2-Cl-phenyl | —N=C(CH₃)₂ | O | O |
| methoxy | H | 4-Cl-phenyl | —N=C(CH₃)₂ | O | O |
| 4-Cl-phenoxy | H | 2,4-(F,F)-phenyl | —N=C(CH₃)₂ | O | O |
| 4-Cl-phenoxy | H | 2,3,5-(Cl,Cl,Cl)-phenyl | —N=C(CH₃)₂ | O | O |
| 4-Cl-phenoxy | H | 2-CN-phenyl | —N=C(CH₃)₂ | O | O |
| 4-Cl-phenoxy | H | 2-OCH₃-phenyl | —N=C(CH₃)₂ | O | O |
| 4-Cl-phenoxy | H | 2,3-(OCH₃,OCH₃)-phenyl | —N=C(CH₃)₂ | O | O |
| 4-Cl-phenoxy | H | 3,4,5-(OCH₃,OCH₃,OCH₃)-phenyl | —N=C(CH₃)₂ | O | O |
| phenylthio | H | 3-OCF₃-phenyl | —N=C(CH₃)₂ | O | O |
| phenylthio | H | 4-OCF₂CHF₂-phenyl | —N=C(CH₃)₂ | O | O |
| phenylthio | H | 2-SCH₃-phenyl | —N=C(CH₃)₂ | O | O |
| phenylthio | H | 2,4-(SCH₃,SCH₃)-phenyl | —N=C(CH₃)₂ | O | O |
| phenylthio | H | 2-SCF₃-phenyl | —N=C(CH₃)₂ | O | O |
| phenylthio | H | 4-NO₂-phenyl | —N=C(CH₃)₂ | O | O |
| 2,4-(Cl,Cl)-phenyl | H | 2,4-(NO₂,NO₂)-phenyl | —N=C(CH₃)₂ | O | O |
| 2,4-(Cl,Cl)-phenyl | H | 2-CHO-phenyl | —N=C(CH₃)₂ | O | O |
| 2,4-(Cl,Cl)-phenyl | H | 3-COCH₃-phenyl | —N=C(CH₃)₂ | O | O |

TABLE A-1/B-1-continued structures Ia and Ib shown

| R¹ | R³ | R⁴ | R⁵ | X | Y |
|---|---|---|---|---|---|
| 2,4-(Cl,Cl)-phenyl | H | 3-COCF₃-phenyl | —N=C(CH₃)₂ | O | O |
| 2,4-(Cl,Cl)-phenyl | H | 1-naphthyl | —N=C(CH₃)₂ | O | O |
| 2,4-(Cl,Cl)-phenyl | H | 2-naphthyl | —N=C(CH₃)₂ | O | O |
| 2-thienyl | H | piperidino | —N=C(CH₃)₂ | O | O |
| 2-thienyl | H | 3-tetrahydrofuranyl | —N=C(CH₃)₂ | O | O |
| 2-thienyl | H | 4-tetrahydropyranyl | —N=C(CH₃)₂ | O | O |
| 2-thienyl | H | 2-thiazolyl | —N=C(CH₃)₂ | O | O |
| 2-thienyl | H | 5-CH₃-2-thiazolyl | —N=C(CH₃)₂ | O | O |
| 2-thienyl | H | 4-CH₃-5-COOH-2-thiazolyl | —N=C(CH₃)₂ | O | O |
| 3-pyridyl | H | methyl | —N=C(CH₃)₂ | O | O |
| 3-pyridyl | H | ethyl | —N=C(CH₃)₂ | O | O |
| 3-pyridyl | H | n-propyl | —N=C(CH₃)₂ | O | O |
| 3-pyridyl | H | iso-propyl | —N=C(CH₃)₂ | O | O |
| 3-pyridyl | H | n-butyl | —N=C(CH₃)₂ | O | O |
| 3-pyridyl | H | iso-butyl | —N=C(CH₃)₂ | O | O |
| iso-propyl | methyl | sec.-butyl | —N=C(CH₃)₂ | O | O |
| iso-propyl | methyl | n-pentyl | —N=C(CH₃)₂ | O | O |
| iso-propyl | methyl | 2-pentyl | —N=C(CH₃)₂ | O | O |
| iso-propyl | methyl | 3-pentyl | —N=C(CH₃)₂ | O | O |
| iso-propyl | methyl | n-hexyl | —N=C(CH₃)₂ | O | O |
| iso-propyl | methyl | 2-hexyl | —N=C(CH₃)₂ | O | O |
| iso-propyl | methyl | 3-hexyl | —N=C(CH₃)₂ | O | O |
| methyl | H | tert.-butyl | 2,4-(Cl,Cl)-phenyl | O | S |
| methyl | H | tert.-butyl | 2-pyridyl | O | S |
| methyl | H | tert.-butyl | ethyl | O | S |
| methyl | H | tert.-butyl | iso-propyl | O | S |
| methyl | H | tert.-butyl | butyl | O | S |
| methyl | H | tert.-butyl | tert.-butyl | O | S |
| methyl | H | tert.-butyl | phenyl | O | S |
| iso-propyl | H | tert.-butyl | 4-F-phenyl | O | S |
| iso-propyl | H | tert.-butyl | 3-CF₃-phenyl | O | S |
| iso-propyl | H | tert.-butyl | 2,4-(Cl,Cl)-phenyl | O | S |
| iso-propyl | H | tert.-butyl | 2-pyridyl | O | S |
| iso-propyl | H | tert.-butyl | methyl | O | S |
| iso-propyl | H | tert.-butyl | ethyl | O | S |
| iso-propyl | H | tert.-butyl | iso-propyl | O | S |
| cyclo-propyl | H | tert.-butyl | butyl | O | S |
| cyclo-propyl | H | tert.-butyl | tert.-butyl | O | S |
| cyclo-propyl | H | tert.-butyl | phenyl | O | S |
| cyclo-propyl | H | tert.-butyl | 4-F-phenyl | O | S |
| cyclo-propyl | H | tert.-butyl | 3-CF₃-phenyl | O | S |
| cyclo-propyl | H | tert.-butyl | 2,4-(Cl,Cl)-phenyl | O | S |
| cyclo-propyl | H | tert.-butyl | 2-pyridyl | O | S |
| allyl | H | tert.-butyl | methyl | O | S |
| allyl | H | tert.-butyl | ethyl | O | S |
| allyl | H | tert.-butyl | iso-propyl | O | S |
| allyl | H | tert.-butyl | butyl | O | S |
| allyl | H | tert.-butyl | tert.-butyl | O | S |
| allyl | H | tert.-butyl | phenyl | O | S |
| methoxy | H | tert.-butyl | methyl | O | S |
| methoxy | H | tert.-butyl | ethyl | O | S |
| methoxy | H | tert.-butyl | iso-propyl | O | S |
| methoxy | H | tert.-butyl | butyl | O | S |
| methoxy | H | tert.-butyl | tert.-butyl | O | S |
| methoxy | H | tert.-butyl | phenyl | O | S |
| methoxy | H | tert.-butyl | 4-F-phenyl | O | S |
| 4-Cl-phenoxy | H | tert.-butyl | 3-CF₃-phenyl | O | S |
| 4-Cl-phenoxy | H | tert.-butyl | 2,4-(Cl,Cl)-phenyl | O | S |
| 4-Cl-phenoxy | H | tert.-butyl | 2-pyridyl | O | S |
| 4-Cl-phenoxy | H | tert.-butyl | methyl | O | S |
| 4-Cl-phenoxy | H | tert.-butyl | ethyl | O | S |
| 4-Cl-phenoxy | H | tert.-butyl | iso-propyl | O | S |
| 4-Cl-phenoxy | H | tert.-butyl | butyl | O | S |
| 2,4-(Cl,Cl)-phenyl | H | tert.-butyl | tert.-butyl | O | S |
| 2,4-(Cl,Cl)-phenyl | H | tert.-butyl | phenyl | O | S |
| 2,4-(Cl,Cl)-phenyl | H | tert.-butyl | 4-F-phenyl | O | S |
| 2,4-(Cl,Cl)-phenyl | H | tert.-butyl | 3-CF₃-phenyl | O | S |
| 2,4-(Cl,Cl)-phenyl | H | tert.-butyl | 2,4-(Cl,Cl)-phenyl | O | S |
| 2,4-(Cl,Cl)-phenyl | H | tert.-butyl | 2-pyridyl | O | S |
| 2,4-(Cl,Cl)-phenyl | H | tert.-butyl | ethyl | O | S |
| 2-thienyl | H | tert.-butyl | iso-propyl | O | S |

TABLE A-1/B-1-continued $$\text{Ia} \quad \text{or} \quad \text{Ib}$$

| R¹ | R³ | R⁴ | R⁵ | X | Y |
|---|---|---|---|---|---|
| 2-thienyl | H | tert.-butyl | butyl | O | S |
| 2-thienyl | H | tert.-butyl | tert.-butyl | O | S |
| 3-pyridyl | H | tert.-butyl | phenyl | O | S |
| 3-pyridyl | H | tert.-butyl | 4-F-phenyl | O | S |
| 3-pyridyl | H | tert.-butyl | 3-CF₃-phenyl | O | S |
| methyl | H | cyclo-propyl | 2,4-(Cl,Cl)-phenyl | O | S |
| methyl | H | cyclo-propyl | 2-pyridyl | O | S |
| methyl | H | cyclo-propyl | ethyl | O | S |
| methyl | H | cyclo-propyl | iso-propyl | O | S |
| methyl | H | cyclo-propyl | butyl | O | S |
| methyl | H | cyclo-propyl | tert.-butyl | O | S |
| methyl | H | cyclo-propyl | phenyl | O | S |
| iso-propyl | H | cyclo-propyl | 4-F-phenyl | O | S |
| iso-propyl | H | cyclo-propyl | 3-CF₃-phenyl | O | S |
| iso-propyl | H | cyclo-propyl | 2,4-(Cl,Cl)-phenyl | O | S |
| iso-propyl | H | cyclo-propyl | 2-pyridyl | O | S |
| iso-propyl | H | cyclo-propyl | methyl | O | S |
| iso-propyl | H | cyclo-propyl | ethyl | O | S |
| iso-propyl | H | cyclo-propyl | iso-propyl | O | S |
| iso-propyl | H | cyclo-propyl | butyl | O | S |
| cyclo-propyl | H | cyclo-propyl | tert.-butyl | O | S |
| cyclo-propyl | H | cyclo-propyl | phenyl | O | S |
| cyclo-propyl | H | cyclo-propyl | 4-F-phenyl | O | S |
| cyclo-propyl | H | cyclo-propyl | 3-CF₃-phenyl | O | S |
| cyclo-propyl | H | cyclo-propyl | 2,4-(Cl,Cl)-phenyl | O | S |
| cyclo-propyl | H | cyclo-propyl | 2-pyridyl | O | S |
| allyl | H | cyclo-propyl | methyl | O | S |
| allyl | H | cyclo-propyl | ethyl | O | S |
| allyl | H | cyclo-propyl | iso-propyl | O | S |
| allyl | H | cyclo-propyl | butyl | O | S |
| allyl | H | cyclo-propyl | tert.-butyl | O | S |
| allyl | H | cyclo-propyl | phenyl | O | S |
| methoxy | H | cyclo-propyl | methyl | O | S |
| methoxy | H | cyclo-propyl | ethyl | O | S |
| methoxy | H | cyclo-propyl | iso-propyl | O | S |
| methoxy | H | cyclo-propyl | butyl | O | S |
| methoxy | H | cyclo-propyl | tert.-butyl | O | S |
| methoxy | H | cyclo-propyl | phenyl | O | S |
| methoxy | H | cyclo-propyl | 4-F-phenyl | O | S |
| 4-Cl-phenoxy | H | cyclo-propyl | 3-CF₃-phenyl | O | S |
| 4-Cl-phenoxy | H | cyclo-propyl | 2,4-(Cl,Cl)-phenyl | O | S |
| 4-Cl-phenoxy | H | cyclo-propyl | 2-pyridyl | O | S |
| 4-Cl-phenoxy | H | cyclo-propyl | methyl | O | S |
| 4-Cl-phenoxy | H | cyclo-propyl | ethyl | O | S |
| 4-Cl-phenoxy | H | cyclo-propyl | iso-propyl | O | S |
| 4-Cl-phenoxy | H | cyclo-propyl | butyl | O | S |
| 2,4-(Cl,Cl)-phenyl | H | cyclo-propyl | tert.-butyl | O | S |
| 2,4-(Cl,Cl)-phenyl | H | cyclo-propyl | phenyl | O | S |
| 2,4-(Cl,Cl)-phenyl | H | cyclo-propyl | 4-F-phenyl | O | S |
| 2,4-(Cl,Cl)-phenyl | H | cyclo-propyl | 3-CF₃-phenyl | O | S |
| 2,4-(Cl,Cl)-phenyl | H | cyclo-propyl | 2,4-(Cl,Cl)-phenyl | O | S |
| 2,4-(Cl,Cl)-phenyl | H | cyclo-propyl | 2-pyridyl | O | S |
| 2,4-(Cl,Cl)-phenyl | H | cyclo-propyl | ethyl | O | S |
| 2-thienyl | H | cyclo-propyl | iso-propyl | O | S |
| 2-thienyl | H | cyclo-propyl | butyl | O | S |
| 2-thienyl | H | cyclo-propyl | tert.-butyl | O | S |
| 3-pyridyl | H | cyclo-propyl | phenyl | O | S |
| 3-pyridyl | H | cyclo-propyl | 4-F-phenyl | O | S |
| 3-pyridyl | H | cyclo-propyl | 3-CF₃-phenyl | O | S |

The oxazole- and thiazolecarboxamides Ia' and Ib', or herbicidal agents containing them, may be applied for instance in the form of directly sprayable solutions, powders, suspensions (including high-percentage aqueous, oily or other suspension), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as a fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and bibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.1 to 95, and preferably 0.5 to 90, % by weight of active ingredient. The active ingredients are used in a purity of 90 to 100, and preferably from 95 to 100, % (according to the NMR spectrum).

Compounds Ia and Ib according to the invention may be formulated for instance as follows:

I. 90 parts by weight of compound no. 1.003 is mixed with 10 parts by weight of N-methyl-alpha-pyrrolidone. A mixture is obtained which is suitable for application in the form of very fine drops.

II. 20 parts by weight of compound no. 1.010 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.004 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into 100,000 parts by weight of water, an aqueous dispersion is obtained containing 0.02% by weight of the active ingredient.

IV. 20 parts by weight of compound no. 1.011 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water, an aqueous dispersion is obtained containing 0.02% by weight of the active ingredient.

V. 20 parts by weight of compound no. 1.011 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.003 is intimately mixed with 97 parts by weight of particulate kaolin. A dust is obtained containing 3% by weight of the active ingredient.

VII. 30 parts by weight of compound no. 1.004 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.010 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the objective to be achieved, the time of the year, the plants to be combated and their growth stages, and range from 0.001 to 5, and preferably from 0.01 to 2, kg/ha.

In view of the number of application methods possible, the compounds according to the invention, or agents containing them, may be used in a large number of crops for eliminating unwanted plant growth.

To increase the spectrum of action and to achieve synergistic effects, the oxazole- and thiazolecarboxamides Ia and Ib may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acids, (hetero)-aryloxyphenoxypropionic acids and salts, esters, amides thereof, etc.

It may also be useful to apply compounds Ia and Ib, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used, after appropriate modification of the starting materials, to obtain further compounds. The compounds thus obtained are given in the following tables with their physical data.

1. METHODS OF MANUFACTURING THE INTERMEDIATES

Example 1.1

4(5)-Ethoxycarbonyl-2-methyloxazole-5(4)-carboxylic acid

At $-10°$ C. and under a nitrogen blanket, a solution of 6.0 (0.15 mol) of sodium hydroxide in 150 ml of water was dripped over a period of 4 hours into 33.8 g (0.15 mol) of 2-methyloxazole-4,5-dicarboxylate in 300 ml of ethanol, and the mixture was stirred at $-10°$ C. for 2 hours. The solution was evaporated down, the residue was taken up in 300 ml of water, the pH was adjusted to 8 to 9 with hydrochloric acid and the solution was extracted twice, each time with 300 ml of diethyl ether. The mixture was then acidified to a pH of 2 with concentrated hydrochloric acid and the aqueous phase was extracted four times, each time with 250 ml of dichloromethane. The combined organic phases were dried over magnesium sulfate and the solvent was removed under reduced pressure. There was obtained 26.4 g (88%) of 4(5)-ethoxycarbonyl-2-methyloxazole-5(4)-carboxylic acid as a white solid (isomer ratio: 3:1 ($^1$H-NMR, HPLC). Fractional crystallization from cyclohexane/ethyl acetate (2:1) or column chromatography using silica gel (toluene, THF, glacial acetic acid (7:3:1)) gave the pure isomer of 4-ethoxycarbonyl-2-methyloxazole-5-carboxylic acid. $^1$H-NMR (250 MHz, D$_6$-DMSO); main isomer: $\delta=1.28$ (t; 3H), 2.52 (s; 3H), 4.30 (q; 2H), 14.00 (broad s; 1H).

Example 1.2

4-Ethoxycarbonyl-2-methylthiothiazole-5-carboxylic acid

At room temperature, a solution of 1.10 g (27.5 mmol) of sodium hydroxide in 10 ml of water was added over a period of one hour to a solution of 7.00 g (25 mmol) of diethyl 2-methylthiothiazole-4,5-dicarboxylate in 100 ml of ethanol/water (2:1). The mixture was stirred for one hour, the solvent mixture was then removed under reduced pressure, the residue was taken up in 100 ml of water, the solution was extracted once with 50 ml of diethyl ether, and the aqueous phase was acidified with concentrated hydrochloric acid. The precipitated product was filtered off and dried.

Yield: 4.50 g (73%). Melting point: 104° C.

The carboxylic acids given in the following table were obtained in accordance with the above example:

| Example | R$^1$ | R$^5$ | X | Physical data |
|---|---|---|---|---|
| 1.9(b) | phenyl | CH$_3$ | S | mp.: 127–137 |
| 1.4(a) | n-butylthio | C$_2$H$_5$ | S | 0.95(t; 3H), 1.40(t; 3H), 1.50 (sext; 2H), 1.80(quint; 2H), 3.40(t; 2H), 4.35(q; 2H) |
| 1.5(b) | n-butylthio | C$_2$H$_5$ | S | 0.95(t; 3H), 1.35(t; 3H), 1.50 (sect; 2H), 1.80(quint; 2H), 3.30(t; 2H), 4.45(q; 2H) |
| 2.6(b) | iso-propylthio | C$_2$H$_5$ | S | 1.50(d; 6H), 1.45(t; 3H), 3.90 (hept; 1H), 4.55(q; 2H), 12.50 (s; 1H) |
| 1.7(a) | iso-propylthio | C$_2$H$_5$ | S | 1.45(t; 3H), 1.50(d; 6H), 4.05 (hept; 1H), 4.50(q; 2H), 12.50 (s; 1H) |
| 1.8(a) | methylthio | CH$_3$ | S | 2.80(s; 3H), 4.05(s; 3H) |

Example 1.9

Diethyl 2-methylthiothiazole-4,5-dicarboxylate

At 0° C., a solution of 2.1 g (0.03 mol) of sodium methylthiolate in 10 ml of ethanol was dripped into a solution of 9.2 g (0.03 mol) of diethyl 2-chlorothiazole-4,5-dicarboxylate in 30 ml of ethanol. The mixture was allowed to heat up to 25° C. and was then stirred for two hours. The solvent was then removed under reduced pressure, the residue was taken up in 100 ml of diethyl ether and the solution washed with 50 ml of 5% strength sodium hydroxide solution and with 50 ml of water. Drying over sodium sulfate and evaporating down gave 7.2 g (87%) of the product as a colorless oil.

$^1$H-NMR (CDCl$_3$, 250 MHz, TMS as internal standard): 1.35 (t, I=7.0 Hz, 3H), 1.45 (t, I=7.0 Hz; 3H), 2.75 (s, 3H), 4.30 (q, I=7.0 Hz; 2H), 4.50 (q, I=7.0 Hz; 2H).

2. PROCESS FOR MANUFACTURING COMPOUNDS VIa AND VIb

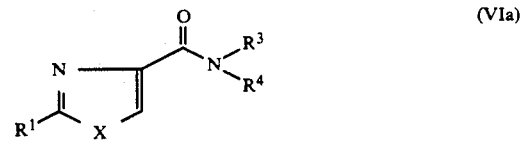
(VIa)

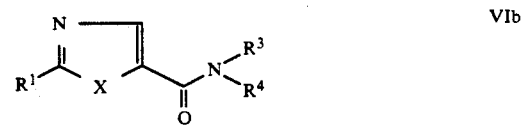
VIb

Example 2.1

2-Methoxythiazole-4-carboxylic acid-tert.-butylamide

At 25° C., 8.90 g of a 30% strength solution (49 mmol) of sodium methanolate in methanol was added to a solution of 12.00 (46 mmol) of 2-bromothiazole-4-carboxylic acid-tert.-butylamide in 150 ml of methanol. The mixture was boiled under reflux for four hours, the clear solution was evaporated down, the residue was taken up to 300 ml of diethyl ether and filtered, and the solvent was removed under reduced pressure. There was obtained 9.60 g (98%) of the product as a yellow oil.

¹H-NMR (CDCl₃, 250 MHz, TMS as internal standard): 1.45 (s; 9H), 4.10 (s; 3H), 7.00 (s, broad, 1H), 7.48 (s; 1H).

Example 2.2

2-Isopropyloxazole-4-carboxylic acid-cyclopropylamide

At room temperature, 47.6 g (0.40 mol) of thionyl chloride was dripped into a solution of 31.0 g (0.20 mol) of 2-isopropyloxazole-4-carboxylic acid in 200 ml of toluene and 2 ml of dimethylformamide, and the mixture was stirred for one hour at 80° C. The solvents were stripped off under reduced pressure, the residue was dissolved in 300 ml of dichloromethane, and 24.0 g (0.42 mol) of cyclopropylamine in 20 ml of dichloromethane was dripped in at 0° to 10° C. The mixture was stirred for 12 hours at room temperature, 150 ml of water was added, the phases were separated, the organic phase was washed once with saturated sodium bicarbonate solution and dried over magnesium sulfate, and the solvent was removed under reduced pressure. There was obtained 37.2 g (96%) of 2-isopropyl-oxazole-4-carboxylic acid-cyclopropylamide.

¹H-NMR (CDCl₃, 250 MHz): $\Delta$=0.62 (m; 2H), 0.88 (m; 2H), 1.34 (d; 6H), 2.86 (m; 1H), 3.09 (m; 1H), 6.93 (broad s; 1H; NH), 8.09 (s; 1H).

The amides listed in the following table were obtained in accordance with the above examples or analogously to the cited literature:

| No. | R¹ | R³ | R⁴ | X | Phys. data [mp. (°C.); NMR (δ in ppm)] |
|---|---|---|---|---|---|
| 2.3(a) | phenylthio | H | tert.-butyl | S | 1.50(s; 9H), 7.00(s; 1H), 7.45(m; 3H), 7.65(m; 2H), 7.85(s; 1H) |
| 2.4(a) | bromo | H | tert.-butyl | S | 64–67 |
| 2.5(a) | phenyl | H | 4-Cl-phenyl | S | 223 |
| 2.6(a) | bromo | H | cyclo-propyl | S | 83–88 |
| 2.7(a) | methoxy | H | cyclo-propyl | S | 62–65 |
| 2.8(a) | methyl | H | tert.-butyl | S | 1.48(s; 9H), 2.72(s; 3H), 7.25(s; 1H, NH), 7.91(s; 1H) |
| 2.9(a) | phenyl | H | tert.-butyl | S | 1.50(s; 9H), 7.40(s; 1H, NH), 7.40–7.90 (m; 5H), 8.03(s; 1H) |
| 2.10(b) | methoxy | H | tert.-butyl | S | 126–129 |
| 2.11(a) | methyl | H | tert.-butyl | O | 60–63 |
| 2.12(a) | cyclo-propyl | H | tert.-butyl | O | 72–74 |
| 2.13(a) | ethyl | H | tert.-butyl | O | 1.35(t; 3H), 1.48(s; 9H), 2.80(q; 2H), 6.78 (s; 1H, NH), 8.01(s; 1H) |
| 2.14(a) | ethyl | H | cyclo-propyl | O | 50–55 |
| 2.15(a) | ethyl | H | 3-CF₃-phenyl | O | 40–43 |
| 2.16(a) | iso-propyl | H | tert.-butyl | O | 1.36(d; 6H), 1.48(s; 9H), 3.06(m; 1H), 6.78 (s; 1H, NH), 8.00(s; 1H) |
| 2.17(a) | iso-propyl | H | cyclo-propyl | O | 0.58–0.96(m; 4H), 1.34(d; 6H), 2.86(m; 1H), 3.08(m; 1H), (s; 1H, NH), 8.09 (s; 1H) |
| 2.18(a) | iso-propyl | H | iso-propyl | O | 38–41 |
| 2.19(a) | cyclo-propyl | H | iso-propyl | O | 57–60 |
| 2.20(a) | cyclo-propyl | H | cyclo-propyl | O | 80–83 |
| 2.21(a) | cyclo-propyl | H | 4-Cl-phenyl | O | 147–150 |
| 2.22(a) | phenyl | H | tert.-butyl | O | 90–93 |
| 2.23(a) | phenyl | H | iso-propyl | O | 68–74 |
| 2.24(a) | phenyl | H | cyclo-propyl | O | 90–94 |
| 2.25(a) | phenyl | H | 3-CF₃-phenyl | O | 127–129 |
| 2.26(a) | methyl | H | cyclo-propyl | S | 109–114 |
| 2.27(a) | p-F-benzyl | H | tert.-butyl | S | 63–64 |
| 2.28(a) | 2,6-Cl,Cl-benzyl | H | cyanomethyl | S | 82–85 |
| 2.29(a) | tert.-butyl | H | tert.-butyl | S | 85–86 |
| 2.30(a) | 2-pyridyl | H | tert.-butyl | S | 93 |
| 2.31(a) | 3-CF₃-benzyl | H | tert.-butyl | S | 97–99 |
| 2.32(a) | 2-phenyl-ethyl | H | cyano-methyl | S | 100 |
| 2.33(a) | 4-Cl-phenoxy-methyl | H | tert.-butyl | S | 102 |
| 2.34(a) | 2,6-Cl,Cl-benzyl | H | tert.-butyl | S | 105–106 |
| 2.35(a) | benzyl | H | tert.-butyl | S | 1.48(s; 9H), 4.30(s; 3H), 7.15–7.42(m; 6H), 7.90(s; 1H) |
| 2.36(a) | 2-methoxy-ethyl | H | tert.-butyl | S | 1.48(s; 9H), 3.25(t; 2H), 3.4(s; 3H), 3.75 (t; 2H), 7.25(s; 1H), 7.95(s; 1H) |
| 2.37(a) | 2,4-Cl,Cl-benzyl | H | tert.-butyl | S | 1.48(s; 9H), 4.40(s; 2H), 7.13–7.48(m; 4H), 7.92(s; 1H) |
| 2.38(a) | 2-phenyl-ethyl | H | tert.-butyl | S | 1.48(s; 9H), 3.10(t; 2H), 3.30(t; 2H), 7.10–7.50)m; 6H), 7.90(s; 1H) |
| 2.39(a) | methyl-thiomethyl | H | tert.-butyl | S | 1.48(s; 9H), 2.16(s; 3H), 3.95(s; 2H), 7.20 (s; 1H), 8.00(s; 1H) |
| 2.40(a) | tert.-butyl | H | tert.-butyl | S | 1.50(s; 9H), 3.86(s; 9H), 7.20(s; 1H), 7.45 (s; 1H) |
| 2.41(a) | methoxymethyl | H | tert.-butyl | S | 1.49(s; 9H), 3.52(s; 3H), 4.7(s; 2H), 7.10 (s; 1H), 8.04(s; 1H) |
| 2.42(a) | 1-phenyl-ethyl | H | tert.butyl | S | 1.48(s; 9H), 1.76(d; 2H), 4.43(1; 1H) 7.15–7.43(m; 6H), 7.93(s; 1H) |
| 2.43(a) | cyclo-hexyl | H | cyclo-propyl | O | 88–91 |
| 2.44(a) | cyclo-hexyl | H | tert.-butyl | O | 46–50 |
| 2.45(a) | n-propyl | H | tert.-butyl | O | 1.00(t; 3H), 1.44(s; 9H), 1.81(m; 2H), 2.74 |

-continued

| No. | $R^1$ | $R^3$ | $R^4$ | X | Phys. data [mp. (°C.); NMR ($\delta$ in ppm)] |
|---|---|---|---|---|---|
| | | | | | (t; 2H), 6.75(broad s; 1H), NH), 8.05 (s; 1H) |
| 2.46(a) | n-propyl | H | cyclo-propyl | O | 54–57 |
| 2.47(a) | n-propyl | H | 2,4-(CH$_3$)$_2$-phenyl | O | 44–47 |
| 2.48(a) | 4-Cl-phenyl | H | cyclo-propyl | O | 164–166 |
| 2.49(a) | 4-Cl-phenyl | H | tert.-butyl | O | 131–133 |
| 2.50(a) | 4-Cl-phenyl | H | iso-propyl | O | 101–105 |
| 2.51(a) | 4-Cl-phenyl | H | 4-Cl-phenyl | O | 165–168 |
| 2.52(a) | methoxymethyl | H | tert.-butyl | O | 1.46(s; 9H), 3.50(s; 3H), 4.50(s; 2H), 6.80 (broad s; 1H, NH), 8.12(s; 1H) |
| 2.53(a) | tert.-butyl | H | tert.-butyl | O | 83–87 |
| 2.54(a) | tert.-butyl | H | cyclo-propyl | O | 78–80 |
| 2.55(a) | tert.-butyl | H | CH(cyclo-propyl)$_2$CH$_3$ | O | 132–134 |
| 2.56(a) | methoxymethyl | H | cyclo-propyl | O | 0.60–0.90(m; 4H), 2.88(m; 1H), 3.44(s; 3H), 4.53(s; 2H), 6.94(broad s; 1H, NH), 8.21 (s; 1H) |

3. METHODS OF MANUFACTURING COMPOUNDS Ia AND Ib

Example 1

4-Cyclopropylaminocarbonyl-2-isopropyloxazole-5-carboxylic acid

At −70° C. and under a nitrogen blanket, 0.12 mol of n-butyllithium (80.0 ml of a 1.5 molar solution in hexane) was dripped into a solution of 10.4 g (0.054 mol) of 2-isopropyloxazole-4-carboxylic acid-cyclopropylamide in 250 ml of tetrahydrofuran, and the mixture was stirred for 30 minutes at this temperature. The reaction mixture was then poured onto 500 g of solid CO$_2$ and allowed to stand overnight. The residue remaining after evaporating down was taken up in 200 ml of water and 30 ml of 2N NaOH, the solution was extracted twice, each time with 100 ml of diethyl ether, the aqueous phase was acidified to a pH of 2 with concentrated hydrochloric acid and the solution extracted three times, each time with 200 ml of ethyl acetate. Drying over magnesium sulfate and removal of the solvent under reduced pressure gave 10.4 g (81%) of 4-cyclopropylaminocarbonyl-2-isopropyloxazole-5-carboxylic acid as a white powder of m.p. 109°–112° C. (active ingredient no. 3.007).

Example 2

4-tert-Butylaminocarbonyl-2-methoxythiazole-5-carboxylic acid

At −70° C., 65 ml of a 1.5 molar solution (97 mmol) of n-butyllithium in n-hexane was dripped into a solution of 8.00 g (37 mmol) of 2-methoxythiazole-4-carboxylic acid-tert-butylamide in 150 ml of tetrahydrofuran, and the mixture was stirred for 30 minutes at this temperature. The reaction mixture was then poured onto 500 g of solid carbon dioxide and allowed to warm up to room temperature over a period of 14 hours. The solvent was removed under reduced pressure, the residue was taken up in a mixture of 150 ml of water and 16 ml of 2N NaOH and filtered, the filtrate was acidified with concentrated hydrochloric acid and the precipitated carboxylic acid was filtered off.

There was obtained 7.80 g (82%) of 4-tert-butylaminocarbonyl-2-methoxythiazole-5-carboxylic acid as a white powder of m.p. 120°–122° C. (active ingredient no. 1.003).

Example 3

5-tert-Butylaminocarbonyl-2-methoxythiazole-4-carboxylic acid

At −70° C. and under a nitrogen blanket, 56 mmol of n-butyllithium (37.3 ml of a 1.5 molar solution in hexane) was dripped into a solution of 5.4 g (25.2 mmol) of 2-methoxythiazole-4-carboxylic acid-tert-butylamide in 150 ml of tetrahydrofuran, and the mixture was stirred for 30 minutes at this temperature. The reaction mixture was then poured onto 500 g of solid CO$_2$ and allowed to stand overnight. After concentration the residue was taken up in 150 ml of water and 10 ml of 2N NaOH, the solution was extracted twice, each time with 50 ml of diethyl ether, and the aqueous phase was acidified to a pH of 2 with concentrated hydrochloric acid and extracted three times, each time with 100 ml of ethyl acetate. Drying over magnesium sulfate and removal of the solvent under reduced pressure gave 3.9 g (60%) of 5-tert-butylaminocarbonyl-2-methoxythiazole-4-carboxylic acid as a white powder of m.p. 105°–110° C. (active ingredient no. 2.001).

Example 4 a) 4-Ethoxycarbonyl-2-methyloxazole-5-carboxylic chloride

At 0° C., 40 ml of thionyl chloride and 1 ml of dimethylformamide were dripped into 12.2 g (61.3 mmol) of 4-ethoxycarbonyl-2-methyloxazole-5-carboxylic acid, and the mixture was refluxed for one hour. The excess thionyl chloride was stripped off under reduced pressure and the residue was distilled under an oil pump vacuum.

There was obtained 10.9 g (82%) of 4-ethoxycarbonyl-2-methyloxazole-5-carboxylic chloride as a yellow oil of m.p. 103°–105° C./0.1 mm. $^1$H-NMR (250 MHz, CDCl$_3$): $\delta$ 1.42 (t; 3H), 2.66 (s; 3H), 4.66 (q; 2H).

b) 4-Ethoxycarbonyl-2-methyloxazole-5-carboxylic acid-tert-butylamide

At 0° C., a solution of 11.0 g (150 mmol) of tert-butylamine in 200 ml of dichloromethane was dripped into 10.9 g (50.3 mmol) of 4-ethoxycarbonyl-2-methyloxazole-5-carboxylic chloride, and the mixture was stirred at this temperature for 12 hours. The reaction mixture was taken up in 200 ml of water, the phases were separated, the organic phase was washed once with saturated sodium bicarbonate solution and once with saturated sodium chloride solution and dried over magnesium sulfate, and the solvent was stripped off under reduced pressure in a rotary evaporator.

There was obtained 11.9 g (93%) of the title compound as a white solid of m.p. 152°–155° C. (active ingredient no. 4.001).

Example 5

5-Tert-Butylaminocarbonyl-2-methyloxazole-4-carboxylic acid

At 0° C. and under a nitrogen blanket, a solution of 1.2 g (30.0 mmol) of sodium hydroxide in 50 ml of water was dripped into 7.4 g (29.1 mmol) of 4-ethoxycarbonyl-2-methyloxazole-5-carboxylic acid-tert-butylamide in 150 ml of ethanol and 50 ml of THF. The mixture was stirred for 2 hours at 20° C., the solvents were stripped off under reduced pressure in a rotary evaporator, the residue was taken up in 300 ml of water, the pH adjusted to 9, and the aqueous phase was extracted three times, each time with 100 ml of diethyl ether. Acidification was then effected to a pH of 2 with 6N HCl and extraction carried out four times, each time with 150 ml of dichloromethane. The organic phase was dried over sodium sulfate and the solvent stripped off under reduced pressure.

There was obtained 6.1 g (93%) of the title compound as a white solid of m.p. 186°–188° C. (active ingredient no. 4.002).

Example 6 a) 4-Ethoxycarbonyl-2-methylthiothiazole-5-carboxylic chloride 3.40 g (13.7 mmol) of 4-ethoxycarbonyl-2-methylthiothiazole-5-carboxylic acid was dissolved in 500 ml of thionyl chloride, and the mixture refluxed until no more gas involved. Excess thionyl chloride was removed under reduced pressure, leaving 3.55 g (98%) of the acyl chloride as a colorless oil.

$^1$H-NMR (CDCl$_3$, 250 MHz, TMS as internal standard): 1.50 (t, I=7.0 Hz; 3H), 2.75 (s; 3H), 4.60 (q, I=7.0 Hz; 2H).

b) 4-Ethoxycarbonyl-2-methylthiothiazole-5-carboxylic acid-tert-butylamide 3.50 g (13.2 mmol) of 4-ethoxycarbonyl-2-methylthiothiazole-5-carboxylic acid chloride was dissolved in 20 ml of dichloromethane and dripped, at 0° C., into a solution of 3.20 g (44 mmol) of tert-butylamine in 50 ml of dichloromethane. The mixture was allowed to warm up to room temperature and was then stirred for 14 hours. 100 ml of 10% strength hydrochloric acid was added and the organic phase was separated, washed with 50 ml of water and dried over sodium sulfate. The solvent was removed under reduced pressure, leaving 4.00 g (100%) of product as a yellow crystalline slurry.

$^1$H-NMR (CDCl$_3$, 250 MHz, TMS as internal standard): 1.45 (t, I=7.0 Hz; 3H), 1.45 (s; 9H), 2.75 (s; 3H), 4.50 (q; I=7.0 Hz; 2H), 9.90 (s broad; 1H). (Active ingredient no. 2.007).

Example 7

5-Tert-Butylaminocarbonyl-2-methylthiothiazole-4-carboxylic acid 0.82 g (14.6 mmol) of potassium hydroxide in 10 ml of water was added to a solution of 4.00 g (13.2 mmol) of 4-ethoxycarbonyl-2-methylthiothiazole-5-carboxylic acid-tert-butylamide in 50 ml of water/ethanol (2:1), and the mixture was refluxed for 2 hours. The solvent mixture was then removed under reduced pressure and the residue was taken up in 50 ml of water and acidified with concentrated hydrochloric acid. The precipitated product was filtered off and dried.

Yield: 3.40 g (94%); m.p. 100° C. (active ingredient no. 2.005).

Example 8

4-tert-Butylaminocarbonyl-2-methoxythiazole-5-carboxylic acid acetoxime ester

At room temperature, 4.4 g (43.6 mmol) of 4-methylmorpholine and 1.5 g (12.3 mmol) of 4-dimethylaminopyridine were dripped into a solution of 3.1 g (12.0 mmol) of 4-tert-butylaminocarbonyl-2-methoxythiazole-5-carboxylic acid and 1.2 g (16.4 mmol) of acetoxime in 100 ml of dichloromethane, and the mixture was stirred for 5 minutes. Subsequently, 10.1 g of a 50% strength solution of propanephosphonic anhydride in dichloromethane (=15.9 mmol) was added and the mixture was refluxed for 7 hours. After concentration, the residue was taken up in 100 ml of ethyl acetate and the solution was extracted twice with saturated sodium bicarbonate solution, and once with 5% strength citric acid solution, once with saturated sodium carbonate solution and once with saturated sodium chloride solution. The organic phase was dried over magnesium sulfate and the solvent was stripped off under reduced pressure.

There was obtained 3.1 g (82%) of 4-tert-butylaminocarbonyl-2-methoxythiazole-5-carboxylic acid-acetoxime ester as a white powder of m.p. 128°–131° C. (active ingredient no. 1.011).

Example 9

5-tert-Butylaminocarbonyl-2-methyloxazole-4-carboxylic acid acetoxime ester

At room temperature, 3.46 g (16.8 mmol) of dicyclohexylcarbodiimide in 20 ml of tetrahydrofuran was dripped into a solution of 3.80 g (16.8 mmol) of 5-tert-butylaminocarbonyl-2-methyloxazole-4-carboxylic acid and 1.23 g (16.8 mmol) of acetoxime in 40 ml of tetrahydrofuran. The mixture was stirred for 14 hours, the precipitate was filtered off, the solvent was stripped off under reduced pressure and the residue was chromatographed using silica gel (cyclohexane/ethyl acetate (1:1)). There was obtained 2.7 g (57%) of 5-tert-butylaminocarbonyl-2-methyloxazole-4-carboxylic acid acetoxime ester as a white solid of m.p. 107°–111° C. (active ingredient no. 4.003).

The active ingredients listed in the tables below were prepared analogously to the above compounds:

TABLE 1

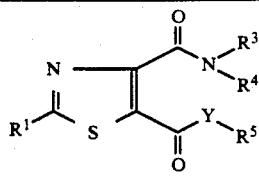

| Example No. | $R^1$ | $R^3$ | $R^4$ | $R^5$ | Y | Phys. data [mp. (°C.); NMR (δ in ppm)] |
|---|---|---|---|---|---|---|
| 1.001 | methyl | H | tert.-butyl | H | O | 141–144 |
| 1.002 | methyl | H | cyclo-propyl | H | O | 138–142 |
| 1.003 | methoxy | H | tert.-butyl | H | O | 120–122 |
| 1.004 | methoxy | H | cyclo-propyl | H | O | 146–148 |
| 1.005 | phenyl | H | tert.-butyl | H | O | 194–195 |
| 1.006 | phenylthio | H | tert.-butyl | H | O | 1.50(s; 9H), 7.55(m; 3H), 7.75(m, 2H), 7.90(s; 1H), 16.60(s; 1H) |
| 1.007 | 4-Cl-phenylthio | H | tert.-butyl | H | O | 1.50(s; 9H), 7.50(d; 2H), 7.65(d, 2H), 8.85(s; 1H), 16.50(s; 1H) |
| 1.008 | methylthio | H | tert.-butyl | H | O | 137 |
| 1.009 | methyl | H | tert.-butyl | —N═C(CH₃)₂ | O | 101–107 |
| 1.010 | methoxy | H | cyclo-propyl | —N═C(CH₃)₂ | O | 128–131 |
| 1.011 | methoxy | H | tert.-butyl | —N═C(CH₃)₂ | O | 128–131 |
| 1.012 | methyl | H | cyclo-propyl | —N═C(CH₃)₂ | O | 0.66(m; 2H), 0.89(m; 2H), 2.10(s, 3H), 2.12(s; 3H), 2.77(s; 3H), 2.94(m; 1H), 8.23(s; 1H) |
| 1.013 | phenyl | H | tert.-butyl | —N═C(CH₃)₂ | O | 143–146 |
| 1.014 | n-butyl-S— | H | tert.-butyl | H | O | 71 |
| 1.015 | iso-propyl-S— | H | tert.-butyl | H | O | 97 |
| 1.016 | 4-F-benzyl | H | tert.-butyl | H | O | 93 |
| 1.017 | 2-phenyl-ethyl | H | tert.-butyl | H | O | 94 |
| 1.018 | methoxy-methyl | H | tert.-butyl | H | O | 100 |
| 1.019 | 2,4-Cl,Cl-benzyl | H | tert.-butyl | H | O | 100–102 |
| 1.020 | 3-CF₃-benzyl | H | tert.-butyl | H | O | 109–110 |
| 1.021 | benzyl | H | tert.-butyl | H | O | 128 |
| 1.022 | tert.-butyl | H | tert.-butyl | H | O | 132 |
| 1.023 | cyclo-propyl | H | tert.-butyl | H | O | 142 |
| 1.024 | 4-Cl-phenoxy-methyl | H | tert.-butyl | H | O | 148–150 |
| 1.025 | iso-propyl | H | tert.-butyl | H | O | 150–153 |
| 1.026 | 4-phenoxy-phenyl | H | tert.-butyl | H | O | 158–161 |
| 1.027 | 3,4,5-trimethoxy-benzyl | H | tert.-butyl | H | O | 162–164 |
| 1.028 | 2-pyridyl | H | tert.-butyl | H | O | 201 |
| 1.029 | 4-F-benzyl | H | tert.-butyl | Na | O | 199 |
| 1.030 | H | H | tert.-butyl | H | O | 147 |
| 1.031 | 1-phenyl-ethyl | H | tert.-butyl | H | O | 1.51(s; 9H), 1.78(d; 2H), 4.40(q; 1H), 7.16–7.45(m; 5H), 8.00(s; 1H), 16-80(s; 1H) |
| 1.032 | 2,6-Cl,Cl-benzyl | H | tert.-butyl | H | O | 1.50(s; 9H), 4.61(s; 2H), 7.25–7.45(m; 3H), 7.95(s; 1H), 16-70(s; 1H) |

TABLE 2

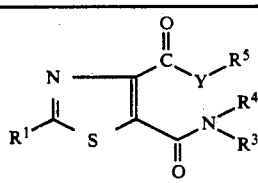

| Example No. | $R^1$ | $R^3$ | $R^4$ | $R^5$ | Y | Phys. data [mp. (°C.); NMR (δ in ppm)] |
|---|---|---|---|---|---|---|
| 2.001 | methoxy | H | tert.-butyl | H | O | 105–110 |
| 2.002 | phenyl | H | tert.-butyl | H | O | 120 |
| 2.003 | phenyl | H | 4-Cl-phenyl | methyl | O | 136 |
| 2.004 | phenyl | H | 4-Cl-phenyl | H | O | 167 |
| 2.005 | methylthio | H | tert.-butyl | H | O | 100 |
| 2.006 | 4-Cl-phenylthio | H | tert.-butyl | H | O | 75–77 |
| 2.007 | SCH₃ | H | tert.-butyl | ethyl | O | 1.45(t, 3H); 2.75(s, 3H); 4.5(q, 2H), 9.9(s, 1H) |
| 2.008 | n-butyl-S— | H | tert.-butyl | H | O | 81 |
| 2.009 | iso-propyl-S— | H | tert.-butyl | H | O | 1.45(s, 9H); 1.50(d, 6H); 3.80("sept.", 1H); 10.0(s, 1H) |
| 2.010 | cyclo-propyl | H | tert.-butyl | H | O | 84 |
| 2.011 | iso-propyl | H | tert.-butyl | H | O | 105–106 |
| 2.012 | 3,4,5-trimethoxy-benzyl | H | tert.-butyl | H | O | 115 |
| 2.013 | methoxy-methyl | H | tert.-butyl | H | O | 120–121 |

TABLE 2-continued

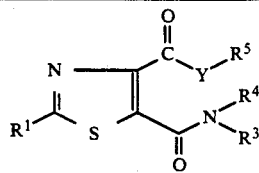

| Example No. | R¹ | R³ | R⁴ | R⁵ | Y | Phys. data [mp. (°C.); NMR (δ in ppm)] |
|---|---|---|---|---|---|---|
| 2.014 | tert.-butyl | H | tert.-butyl | H | O | 143 |
| 2.015 | benzyl | H | tert.-butyl | ethyl | O | 152-156 |
| 2.016 | cyclo-propyl | H | tert.-butyl | ethyl | O | 0.95-1.08(m,; 2H), 1.15-128(m; 2H), 1.45(t; 3H), 1.45(s; 9H), 2.28-2.42(m; 1H), 4.45(q; 2H), 9.92(s; 1H) |
| 2.017 | methoxy-methyl | H | tert.-butyl | H | O | 1.45(s; 9H), 3.55(s; 3H), 4.75(s; 2H), 9.18-9.65(s; 1H), 9.98(s; 1H), |
| 2.018 | methoxy-methyl | H | tert.-butyl | ethyl | O | 1.42(t; 3H), 1.45(s; 9H), 3.50(s; 3H), 4.50(q; 2H), 4.75(s; 2H), 9.95(s; 1H) |
| 2.019 | 4-F-benzyl | H | tert.-butyl | H | O | 1.45(s; 9H), 4.30(s; 2H), 6.95-7.15(m; 2H), 7.20-7.35(m; 2H), 9.95(s; 1H) |

TABLE 3

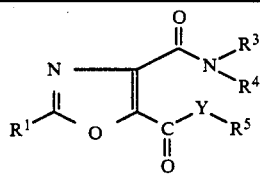

| Example No. | R¹ | R³ | R⁴ | R⁵ | Y | Phys. data [mp. (°C.); NMR (δ in ppm)] |
|---|---|---|---|---|---|---|
| 3.001 | methyl | H | tert.-butyl | H | O | 152-157 |
| 3.002 | ethyl | H | tert.-butyl | H | O | 130-131 |
| 3.003 | ethyl | H | cyclo-propyl | H | O | 135-138 |
| 3.004 | ethyl | H | 3-CF₃-propyl | H | O | 169-172 |
| 3.005 | cyclo-propyl | H | tert.-butyl | H | O | 117 |
| 3.006 | iso-propyl | H | tert.-butyl | H | O | 151-153 |
| 3.007 | iso-propyl | H | cyclo-propyl | H | O | 109-112 |
| 3.008 | iso-propyl | H | iso-propyl | H | O | 64-70 |
| 3.009 | ethyl | H | tert.-butyl | —N=C(CH₃)₂ | O | 107-109 |
| 3.010 | ethyl | H | cyclo-propyl | —N=C(CH₃)₂ | O | 87-90 |
| 3.011 | ethyl | H | 3-CF₃-phenyl | —N=C(CH₃)₂ | O | 118-120 |
| 3.012 | iso-propyl | H | tert.-butyl | —N=C(CH₃)₂ | O | 121-125 |
| 3.013 | iso-propyl | H | cyclo-propyl | —N=C(CH₃)₂ | O | 62-65 |
| 3.014 | iso-propyl | H | iso-propyl | —N=C(CH₃)₂ | O | 76-79 |
| 3.015 | cyclo-propyl | H | tert.-butyl | —N=C(CH₃)₂ | O | 101-104 |
| 3.016 | cyclo-propyl | H | iso-propyl | H | O | 148-151 |
| 3.017 | cyclo-propyl | H | iso-propyl | —N=C(CH₃)₂ | O | 103-106 |
| 3.018 | cyclo-propyl | H | cyclo-propyl | H | O | 126-129 |
| 3.019 | cyclo-propyl | H | cyclo-propyl | —N=C(CH₃)₂ | O | 108-110 |
| 3.020 | cyclo-propyl | H | 4-Cl-phenyl | H | O | 213-215 |
| 3.021 | ethyl | H | iso-propyl | H | O | 103-106 |
| 3.022 | ethyl | H | iso-propyl | —N=C(CH₃)₂ | O | 93-95 |
| 3.023 | ethyl | H | tert.-butyl | —N=C(cyclo-propyl)₂ | O | 107-110 |
| 3.024 | iso-propyl | H | tert.-butyl | CH₂—C≡CH | O | 1.42(d; 6H), 1.44(s; 9H), 2.61(t; 1H), 3.18(m; 1H), 5.00(d; 2H), 8.46(bs; 1H, NH) |
| 3.025 | phenyl | H | tert.-butyl | H | O | 203-206 |
| 3.026 | phenyl | H | iso-propyl | H | O | 144-146 |
| 3.027 | phenyl | H | cyclo-propyl | H | O | 217-218 |
| 3.028 | iso-propyl | H | tert.-butyl | 4-CH₃O-phenyl | O | 137-139 |
| 3.029 | cyclo-propyl | H | 4-Cl-phenyl | —N=C(CH₃)₂ | O | 126-128 |
| 3.030 | phenyl | H | tert.-butyl | —N=C(CH₃)₂ | O | 149-154 |
| 3.031 | phenyl | H | cyclo-propyl | —N=C(CH₃)₂ | O | 160-164 |
| 3.032 | cyclo-hexyl | H | tert.-butyl | —N=C(CH₃)₂ | O | 121-125 |
| 3.033 | cyclo-hexyl | H | cyclo-propyl | H | O | 117-119 |
| 3.034 | cyclo-hexyl | H | cyclo-propyl | —N=C(CH₃)₂ | O | 119-122 |
| 3.035 | phenyl | H | iso-propyl | —N=C(CH₃)₂ | O | 137-139 |
| 3.036 | n-propyl | H | tert.-butyl | H | O | 108-110 |
| 3.037 | n-propyl | H | tert.-butyl | —N=C(CH₃)₂ | O | 69-72 |
| 3.038 | n-propyl | H | cyclo-propyl | H | O | 120-123 |
| 3.039 | n-propyl | H | 2,4-(CH₃)₂-phenyl | H | O | 142-145 |
| 3.040 | methoxymethyl | H | tert.-butyl | H | O | 104-109 |
| 3.041 | tert.-butyl | H | tert.-butyl | H | O | 176-178 |

TABLE 3-continued

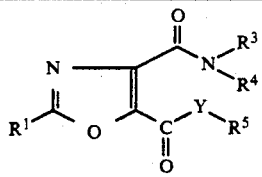

| Example No. | $R^1$ | $R^3$ | $R^4$ | $R^5$ | Y | Phys. data [mp. (°C.); NMR (δ in ppm)] |
|---|---|---|---|---|---|---|
| 3.042 | tert.-butyl | H | cyclo-propyl | H | O | 132–134 |
| 3.043 | tert.-butyl | H | —CH—CH$_3$<br>\|<br>cyclo-propyl | H | O | 114–118 |
| 3.044 | tert.-butyl | H | tert.-butyl | —N=C(CH$_3$)$_2$ | O | 125–128 |
| 3.045 | tert.-butyl | H | cyclo-propyl | —N=C(CH$_3$)$_2$ | O | 123–126 |
| 3.046 | tert.-butyl | H | —CH—CH$_3$<br>\|<br>cyclo-propyl | —N=C(CH$_3$)$_2$ | O | 124–127 |

TABLE 4

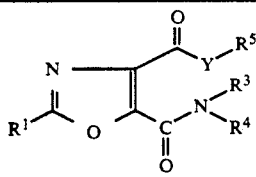

| Example No. | $R^1$ | $R^3$ | $R^4$ | $R^5$ | Y | Phys. data [mp. (°C.); NMR (δ in ppm)] |
|---|---|---|---|---|---|---|
| 4.001 | methyl | H | tert.-butyl | ethyl | O | 152–155 |
| 4.002 | methyl | H | tert.-butyl | H | O | 186–188 |
| 4.003 | methyl | H | tert.-butyl | —N=C(CH$_3$)$_2$ | O | 107–111 |
| 4.004 | phenyl | H | tert.-butyl | ethyl | O | 155–166 |
| 4.005 | phenyl | H | tert.-butyl | H | O | 230–232 |

USE EXAMPLES

The herbicidal action of the oxazole- and thiazolecarboxamides of the formulae Ia' and Ib' is demonstrated in greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the active ingredients, suspended or emulsified in water, were applied to the surface of the soil immediately after the seeds had been sown. The vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for post-emergence treatment was 1.0 kg/ha.

The pots were set up in the greenhouse, heat-loving species at 20° to 35° C., and species from moderate climates at 10° to 25° C. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were Cssia tora, Chenopodium album, Chrysanthemum coronarium, Ipomoea spp., Triticum aestivum and Veronica spp.

Active ingredients nos. 1.001, 1.003, 1.004, 1.009, 1.010, 1.011, 3.002, 3.005 and 3.024, applied postemergence at a rate of 1.0 kg/ha, provide excellent control of unwanted broadleaved plants. Compounds nos. 1.001, 1.003 and 1.009 are also tolerated by wheat. Compound no. 3.005 is excellently tolerated by Indian corn.

We claim:

1. Process for combatting unwanted plant growth which comprises treating the unwanted plants and/or the area to be kept free from unwanted plant growth with a herbicidally effective amount of a thiazolecarboxamide of the formula IA

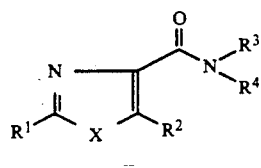

where

X is sulfur;

$R^1$ is hydrogen; halogen; C$_1$–C$_6$-alkyl which can carry from one to five halogen atoms and/or one or two of the following: C$_3$–C$_6$-cycloalkyl, C$_1$–C$_4$- alkoxy, $C_1$-$C_4$-haloalkoxy, $C_1$-$C_4$-alkylthio, $C_1$-$C_4$-haloalkylthio or cyano; benzyl which can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro; $C_3$-$C_8$ cycloalkyl which can carry from one to three of the following: $C_1$-$C_4$-alkyl or halogen; $C_2$-$C_6$-alkenyl which can carry from one to three of the following: halogen, $C_1$-$C_3$-alkoxy and/or one phenyl which in turn can carry form one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro; $C_2$-$C_6$-alkynyl which can carry from one to three of the following: halogen, $C_1$-$C_3$-alkoxy and/or one phenyl which in turn can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro; $C_1$-$C_4$-alkoxy; $C_1$-$C_4$-alkylthio; $C_1$-$C_4$-haloalkoxy; $C_1$-$C_4$-haloalkylthio; phenoxy or phenylthio, which can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro; a 5- to 6-membered heterocyclic radical containing one or two hetero atoms selected from the group consisting of oxygen, sulfur and nitrogen, it being possible for the ring to carry one or two of the following: $C_1$-$C_3$-alkyl, halogen, $C_1$-$C_3$-alkoxy or $C_1$-$C_3$-alkoxycarbonyl; phenyl which can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro and cyano;

$R^2$ is formyl, 4,5-dihydro-2-oxazolyl or —$COYR^5$;

Y is oxygen or sulfur;

$R^5$ is hydrogen; $C_1$-$C_6$-alkyl which can carry from one to give halogen atoms or hydroxyl groups and/or one of the following: $C_1$-$C_4$-alkoxy, $C_2$-$C_4$-alkoxy-$C_1$-$C_4$-alkoxy, cyano, trimethylsilyl, $C_1$-$C_3$-alkylthio, $C_1$-$C_3$-alkylamino, di-$C_1$-$C_3$-alkylamino, $C_3$-$C_7$-cycloalkylamino, $C_1$-$C_3$-alkylsulfinyl, $C_1$-$C_3$-alkylsulfonyl, carboxyl, $C_1$-$C_3$-alkoxycarbonyl, di-$C_1$-$C_3$-alkylaminocarbonyl, di-$C_1$-$C_3$-alkoxyphosphoryl, alkaneiminoxy, thienyl, furyl, tetrahydrofuryl, phthalimido, pyridyl, benzyloxy or benzoyl, it being possible for the cyclic radicals in turn to carry from one to three of the following: $C_1$-$C_3$-alkyl, $C_1$-$C_3$-alkoxy or halogen; benzyl which can carry from one to three of the following: $C_1$-$C_3$-alkyl, $C_1$-$C_3$-alkoxy, $C_1$-$C_3$-haloalkyl, halogen, nitro and cyano; $C_3$-$C_8$-cycloalkyl; phenyl, which can carry from one to three of the following: $C_1$-$C_4$-alkyl, $C_1$-$C_4$-alkoxy, $C_1$-$C_4$-haloalkyl, $C_1$-$C_4$-haloalkoxy, $C_1$-$C_4$-alkoxycarbonyl, halogen, nitro and cyano; $C_3$-$C_8$-alkenyl, $C_5$-$C_6$-cycloalkenyl or $C_3$-$C_8$-alkynyl, it being possible for these radicals to carry one of the following: hydroxyl, $C_1$-$C_4$-alkoxy, halogen or a phenyl ring which in turn can carry from one to three of the following: $C_1$-$C_4$-alkyl, $C_1$-$C_4$-alkoxy, $C_1$-$C_4$-haloalkyl, halogen, nitro and cyano; a 5- to 6-membered heterocyclic radical containing one or two hetero atoms selected from the group consisting of oxygen, sulfur and nitrogen or a benzotriazolyl radical; phthalimido; tetrahydrophthalimido; succinimido; maleimido; one equivalent of a cation from the group consisting of the alkali metals or alkaline earth metals, manganese, copper, iron, ammonium and substituted ammonium;

—$N\!=\!CR^6R^7$;

$R^6$ and $R^7$ are hydrogen; $C_1$-$C_4$-alkyl; $C_3$-$C_8$-cycloalkyl; phenyl or furyl, or together form a methylene chain —$(CH_2)_m$— with m=4 to 7;

$R^3$ is hydrogen; $C_1$-$C_4$-alkyl which can carry from one to three of the following: hydroxyl, halogen, $C_1$-$C_4$-alkoxy, $C_1$-$C_4$-alkylthio or di-$C_1$-$C_3$-alkylamino; $C_3$-$C_8$-cycloalkyl which can carry from one to three of the following: $C_1$-$C_4$-alkyl, halogen and $C_1$-$C_4$-haloalkyl;

$R^4$ is hydroxyl; $C_1$-$C_4$-alkoxy; $C_1$-$C_8$-alkyl which can carry from one to three of the following: $C_1$-$C_4$-alkoxy, $C_1$-$C_4$-haloalkoxy, $C_1$-$C_4$-alkylthio, $C_1$-$C_4$-haloalkylthio, di-$C_1$-$C_4$-alkylamino, halogen, $C_3$-$C_8$-cycloalkyl or phenyl which in turn can carry from one to three of the following: halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio or $C_1$-$C_4$-haloalkylthio; $C_3$-$C_8$-cycloalkyl which can carry from one to three of the following: $C_1$-$C_6$-alkyl, $C_1$-$C_6$-haloalkyl, $C_1$-$C_4$-alkoxy, $C_1$-$C_4$-haloalkoxy, halogen, nitro or cyano; $C_3$-$C_6$-alkenyl or $C_3$-$C_6$-alkynyl, which can be substituted from once to three times by halogen and/or once by phenyl which in turn can carry from one to three of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, cyano or nitro; a 5- to 6-membered heterocyclic radical which contains one or two hetero atoms selected from the group consisting of oxygen, sulfur or nitrogen, and which can carry from one to three of the following: $C_1$-$C_4$-alkyl or halogen; phenyl which can carry from one to four of the following: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, halogen, nitro, cyano, formyl, $C_1$-$C_4$-alkanoyl, $C_1$-$C_4$-haloalkanoyl or $C_1$-$C_4$-alkoxycarbonyl; naphthyl which can be substituted from once to three times by $C_1$-$C_4$-alkyl or halogen, or $R^3$ and $R^4$ together form —$(CH_2)_n$—$Y_p$—$(CH_2)_q$— when n and q are each 1, 2 or 3, p is 0 or 1 and Y is oxygen, sulfur or N-methyl, or —$(CH_2)_3$—$CO$—, and the environmentally compatible salts thereof.

2. A process for combatting unwanted plant growth, wherein the unwanted plants and/or the area to be kept free from unwanted plant growth are treated with a herbicidally effective amount of a compound of the formula Ia

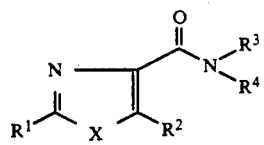

Ia wherein X is sulfur,
$R^1$ is alkyl of 1–6 carbons or methoxy, $R^2$ is $COYR^5$, $R^3$ is H, $R^4$ is cyclopropyl or t-butyl, $R^5$ is H, —$N\!=\!C(CH_3)_2$ or $CH_2$—$C\!\equiv\!CH$ and Y is oxygen.

3. A process as defined in claim 2, wherein $R^1$ of the compound of the formula Ia is ethyl, $R^4$ is t-butyl and $R^5$ is H.

* * * * *

UNITED STATES PATENT AND TRADEMARK OFFICE
CERTIFICATE OF CORRECTION

PATENT NO. : 5,256,633
DATED : Oct. 26, 1993
INVENTOR(S) : DITRICH et al.

It is certified that error appears in the above-identified patent and that said Letters Patent is hereby corrected as shown below:

ON THE TITLE PAGE

Insert the following below the filing date:

--[30] Foreign Application Priority Data
  Sep. 26, 1989 [DE] Fed. Rep. of Germany 3932052--.

IN THE CLAIMS

Claim 1, column 75, line 38, "give" should read --five--.

Claim 1, column 75, line 45, "di-$C_1$-$C_3$-alkoxyphosporyl" should read --di-$C_1$-$C_3$-alkoxyphosphoryl--.

UNITED STATES PATENT AND TRADEMARK OFFICE
CERTIFICATE OF CORRECTION

PATENT NO. : 5,256,633
DATED : Oct. 26, 1993
INVENTOR(S) : DITRICH et al.

It is certified that error appears in the above-identified patent and that said Letters Patent is hereby corrected as shown below:

IN THE ABSTRACT (On the title page, item [57]):

At the line numbers indicated below (line number 1 being the first line after formula Ib), insert the following:

line 2, "oxygen" should read --X oxygen--;
line 3, "hydrogen" should read --$R^1$ hydrogen--;
line 8, "formyl" should read --$R^2$ formyl--;
line 9, "oxygen" should read --Y oxygen--;
line 10, "hydrogen" should read --$R^5$ hydrogen--;
line 19, "hydrogen" should read --$R^3$ hydrogen--.

Signed and Sealed this

Seventeenth Day of May, 1994

BRUCE LEHMAN

Attest:

Attesting Officer        Commissioner of Patents and Trademarks